(12) United States Patent
Wieland et al.

(10) Patent No.: US 7,811,076 B2
(45) Date of Patent: Oct. 12, 2010

(54) ALKALINE PROTEASE AND WASHING AND CLEANING PRODUCTS CONTAINING SAID NOVEL ALKALINE PROTEASE

(75) Inventors: Susanne Wieland, Dormagen-Zons (DE); Karl-Heinz Maurer, Erkrath (DE); Beatrix Kottwitz, Erkrath (DE); Frank Niehaus, Heppenheim (DE); Patrick Lorenz, Lorsch (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 1053 days.

(21) Appl. No.: 11/473,708

(22) Filed: Jun. 22, 2006

(65) Prior Publication Data

US 2007/0010417 A1    Jan. 11, 2007

Related U.S. Application Data

(63) Continuation of application No. PCT/EP2004/014333, filed on Dec. 16, 2004.

(30) Foreign Application Priority Data

Dec. 23, 2003    (DE) ................ 103 60 805

(51) Int. Cl.
*C12N 9/48* (2006.01)
(52) U.S. Cl. ..................................... 425/212
(58) Field of Classification Search ............... None
See application file for complete search history.

(56) References Cited

U.S. PATENT DOCUMENTS

| | | | |
|---|---|---|---|
| 3,893,929 A | 7/1975 | Basadur |
| 3,985,923 A | 10/1976 | Basadur |
| 4,116,885 A | 9/1978 | Derstadt |
| 4,664,839 A | 5/1987 | Rieck |
| 4,820,439 A | 4/1989 | Rieck |
| 5,230,891 A | 7/1993 | Nakayama |
| 5,344,770 A | 9/1994 | Hitomi |
| 5,352,604 A | 10/1994 | Wilson |
| 5,453,372 A | 9/1995 | Vetter |
| 5,614,161 A | 3/1997 | Wilkens |
| 5,705,169 A | 1/1998 | Stein |
| 5,730,960 A | 3/1998 | Stein |
| 5,783,545 A | 7/1998 | Paatz |
| 6,075,001 A | 6/2000 | Wilde |
| 6,087,315 A | 7/2000 | Rasmussen |
| 6,110,884 A | 8/2000 | Rasmussen |
| 6,187,055 B1 | 2/2001 | Kottwitz |
| 6,193,960 B1 | 2/2001 | Metzger |
| 6,228,827 B1 | 5/2001 | Penninger |
| 6,379,394 B1 | 4/2002 | Chilou |
| 6,407,247 B1 | 6/2002 | Habeck |
| 6,509,021 B1 | 1/2003 | Weiss |
| 6,541,233 B1 | 4/2003 | Hillen |
| 6,991,922 B2 | 1/2006 | Dupret |
| 2003/0113895 A1 | 6/2003 | Estell |
| 2004/0005695 A1 | 1/2004 | Miksch |
| 2004/0235125 A1 | 11/2004 | Kottwitz |
| 2004/0259222 A1 | 12/2004 | Breves |
| 2005/0003419 A1 | 1/2005 | Breves |
| 2005/0003504 A1 | 1/2005 | Weber |
| 2005/0003985 A1 | 1/2005 | Kottwitz |
| 2005/0009167 A1 | 1/2005 | Weber |
| 2005/0043198 A1 | 2/2005 | Weber |
| 2005/0049165 A1 | 3/2005 | Kottwitz |
| 2005/0113273 A1 | 5/2005 | Weber |

FOREIGN PATENT DOCUMENTS

| | | |
|---|---|---|
| CA | 2306376 | 10/2000 |
| CA | 2326758 | 5/2001 |
| DE | 1617141 | 4/1972 |
| DE | 2200911 | 1/1973 |
| DE | 2253063 | 5/1973 |
| DE | 2857292 | 2/1980 |
| DE | 3324258 | 1/1984 |
| DE | 4013142 | 10/1991 |
| DE | 4443177 | 6/1996 |
| DE | 19601063 | 9/1996 |
| DE | 19616693 | 11/1997 |
| DE | 19616767 | 11/1997 |
| DE | 19616769 | 11/1997 |
| DE | 19616770 | 11/1997 |
| DE | 19709284 | 9/1998 |
| DE | 19712033 | 9/1998 |
| DE | 19857543 | 6/2000 |
| DE | 19918267 | 10/2000 |
| DE | 10138753 | 3/2003 |
| EP | 0066944 | 12/1982 |
| EP | 0164514 | 12/1985 |
| EP | 0185427 | 6/1986 |
| EP | 0199404 | 10/1986 |
| EP | 0241984 | 10/1987 |
| EP | 0241985 | 10/1987 |
| EP | 0251446 | 1/1988 |
| EP | 0253567 | 1/1988 |
| EP | 0272033 | 6/1988 |
| EP | 0274907 | 7/1988 |
| EP | 0283075 | 9/1988 |
| EP | 0357280 | 3/1990 |

(Continued)

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug 2003;36(3):307-40. Review.*

(Continued)

*Primary Examiner*—Sheridan Swope
(74) *Attorney, Agent, or Firm*—David P. LeCroy

(57) ABSTRACT

An alkaline protease, the DNA thereof having been taken from a bottom sample, alkaline proteases that are at least 40% identical, and nucleic acids with an identity at least 50% homologous with the associated nucleic acids. The invention also relates to the fragment of said protease comprising the amino acid positions 108 to 325, in addition to the gene fragment coding therefor, and alkaline proteases that are at least 60% identical or nucleic acids that are at least 70% identical. Furthermore, the invention defines technical possibilities of use for said proteases, especially use thereof in washing and cleaning products.

10 Claims, 12 Drawing Sheets

FOREIGN PATENT DOCUMENTS

| | | |
|---|---|---|
| EP | 0472042 | 2/1992 |
| EP | 0493398 | 7/1992 |
| EP | 0525239 | 2/1993 |
| EP | 0693471 | 1/1996 |
| EP | 0694521 | 1/1996 |
| EP | 0728749 | 8/1996 |
| EP | 0736084 | 10/1996 |
| EP | 0747471 | 12/1996 |
| EP | 0755944 | 1/1997 |
| EP | 0818450 | 1/1998 |
| EP | 1288282 | 3/2003 |
| GB | 1154730 | 6/1969 |
| GB | 1243784 | 8/1971 |
| GB | 1377092 | 12/1974 |
| GB | 2123848 | 2/1984 |
| GB | 2165856 | 4/1986 |
| WO | WO 88/07581 | 10/1988 |
| WO | WO 88/08028 | 10/1988 |
| WO | WO 88/08033 | 10/1988 |
| WO | WO 89/09819 | 10/1989 |
| WO | WO 91/06637 | 5/1991 |
| WO | WO 91/02792 | 3/1992 |
| WO | WO 92/21760 | 12/1992 |
| WO | WO 93/07276 | 4/1993 |
| WO | WO 93/18140 | 9/1993 |
| WO | WO 94/27970 | 12/1994 |
| WO | WO 94/28102 | 12/1994 |
| WO | WO 94/28103 | 12/1994 |
| WO | WO 94/29426 | 12/1994 |
| WO | WO 95/00626 | 1/1995 |
| WO | WO 95/07770 | 3/1995 |
| WO | WO 95/10591 | 4/1995 |
| WO | WO 95/14075 | 5/1995 |
| WO | WO 95/14759 | 6/1995 |
| WO | WO 95/17498 | 6/1995 |
| WO | WO 95/23221 | 8/1995 |
| WO | WO 95/26398 | 10/1995 |
| WO | WO 95/32232 | 11/1995 |
| WO | WO 96/02653 | 2/1996 |
| WO | WO 96/25489 | 8/1996 |
| WO | WO 96/29397 | 9/1996 |
| WO | WO 96/34092 | 10/1996 |
| WO | WO 97/07770 | 3/1997 |
| WO | WO 97/09446 | 3/1997 |
| WO | WO 97/14804 | 4/1997 |
| WO | WO 97/18287 | 5/1997 |
| WO | WO 97/24177 | 7/1997 |
| WO | WO 97/25399 | 7/1997 |
| WO | WO 97/31085 | 8/1997 |
| WO | WO 98/12307 | 3/1998 |
| WO | WO 99/06573 | 2/1999 |
| WO | WO 99/49057 | 9/1999 |
| WO | WO 99/57154 | 11/1999 |
| WO | WO 99/57254 | 11/1999 |
| WO | WO 00/01826 | 1/2000 |
| WO | WO 00/01831 | 1/2000 |
| WO | WO 00/09679 | 2/2000 |
| WO | WO 00/24882 | 5/2000 |
| WO | WO 00/60042 | 10/2000 |
| WO | WO 01/07575 | 2/2001 |
| WO | WO 01/38471 | 5/2001 |
| WO | WO 01/68821 | 9/2001 |
| WO | WO 01/81597 | 11/2001 |
| WO | WO 02/36727 | 5/2002 |
| WO | WO 02/44350 | 6/2002 |
| WO | WO 03/002711 | 1/2003 |
| WO | WO 03/038082 | 5/2003 |
| WO | WO 03/054177 | 7/2003 |
| WO | WO 03/054184 | 7/2003 |
| WO | WO 03/054185 | 7/2003 |
| WO | WO 03/055974 | 7/2003 |
| WO | WO 03/056017 | 7/2003 |

OTHER PUBLICATIONS

Santosa, D.A., "Rapid extraction and purification of environmental DNA for Molecular Cloning . . . ," Molecular Biotechnology, 17:59-64, (2001).
Gupta, R., et al., "Bacterial alkaline proteases: molecular approaches and industrial applications," Appl. Microbiol. Biotechnol., 59:15-32, (2002).
Lorenz, P., et al., "Metagenome—a challenging source of enzyme discovery," J. Molec. Catalysis, B: Enzymatic, 19-20, 13-19, (2002).
Bott, R., et al., eds., "Subtilases: Subtilisin-like serine proteases," Subtilisin Enzymes, Plenum Press, NY, 75-93 (1996).
Horikoshi, K., et al., "Alkalophilic Microorganisms," Japan Scientific Societies Press, Tokyo, Springer-Verlag, 11-26 (1982).
Zhao, H., et al., "Molecular evolution by staggered extension process (StEP) in vitro recombination," Nature Biotech., 16:258-261 (1998).
Shao, Z., et al., "Random-priming in vitro recombination: an effective tool for directed evolution," Nuc. Acids Res., 26:681-683, (1998).
Stemmer, W., "Rapid evolution of a protein in vitro by DNA shuffling," Nature, 370:389-391, (1994).
Coco, W.M., et al., "DNA shuffling method for generating highly recombined genes and evolved enzymes," Nature Biotech., 19:354-359, (2001).
Vasantha, N., et al., "Genes for alkaline protease and neutral protease from Bacillus . . . ," J. Bacteriology, 159:811-819, (1984).
Wells, J.A., et al., "Cloning, sequencing, and secretion of Bacillus amyloiquefaciens subtilisin in Bacillus subtilis," Nuc. Acids Res., 11:7911-7925, (1983).
Smith, E.L., et al., "Subtilisin Carlsberg," J. Biol. Chem., 243:2184-2191, (1968).
Jacobs, M., et al., "Cloning, sequencing and expression of subtilisin Carlsberg from Bacillus licheniformis," Nuc. Acids Res., 13:8913-8926, (1985).
Nedkov, P., et al., "Determination of the complete amino-acid sequence of subtilisin DY and its comparison with the primary . . . ," Biol. Chem. Hoppe-Seyler, 366:421-430, (1985).
Goddette, D.W., et al., "The crystal structure of the Bacillus lentus alkaline protease . . . ," J. Mol. Biol., 228:580-595, (1992).
Meloun, B., et al., "Complete primary structure of thermitase from Thermoactinomyces vulgaris and its structural features . . . ," FEBS 2463, 183:195-200, (1985).
Jany, K-D., et al., "Proteinase K from Tritirachium album limber," Biol. Bhem., Hoppe-Seyler, 366:485-492, (1985).
Lexikon der Biochemie, Spektrum Akademischer Verlag GmbH, Berlin, 266-271, 226-229 (1999).
Lipman, D.J., et al., "Rapid and sensitive protein similarity searches," Science, 227:1435-1441, (1985).
Altschul, S.F., et al., "Gapped BLAST and PSI-BLAST: a new generation of protein database search programs," Nuc. Acids Res., 25:3389-3402, (1997).
Van Raay, H.G., et al., "Zur bestimmung der proteolytischen Aktivitat in Enzymkonzentraten . . . ," Tenside, 7:125-132, (1970).
Wallhausser, K.H., "Praxis der Sterilisation Desinfektion—Konservierung," Georg Thieme Verlag Stuttgart, NY, 465-652 (1995).
Finkel, P., "Formulierung kosmetischer Sonnenschutzmittel," SOFW-Journal, 122:543-548, (1996).
Breier, R., et al., "Rein enzymatische Antifilzausrutung von Wolle nach dem Lanazym-Verfahren," Mellian Textilberichte, 4:298-302 (2000).
Lundstrom, A., et al., "Stratum corneum chymotryptic enzyme: a proteinase which may be generally present . . . ," Acta Derm Venereol (Stockh), 71:471-474, (1991).
Zhou, J., et al., "DNA recovery from soils of diverse composition," Applied and Environmental Microbiology, 62:316-322, (1996).
Kaiser, R.J., et al., "Specific-primer-directed DNA sequencing using automated fluorescence detection," Nuc. Acids Res., 17:6087-6102, (1989).
Uhlig, H., "Industrial Enzymes and their Applications," John Wiley & Sons, Inc., NY, 1998.

\* cited by examiner

Figure 1

```
           1                                                            50
HP23   MTSTRTLATS LMS..LTTAA LFALCSAGQA TAAPASPDTK DVAGVSSAAV
BLAP   ...AQSVPWG ISRVQAPAAH NRGLTGSGVK VAVLDTGIST HPDLNIRGGA
 SB2   MVSKKSVKRG LITGLIGISI YSLGMHPAQA APSPHTPVSS DPSYKAETSV 51                                                           100
HP23   TDTSG.ADYW TPERMRSAIP ADVLAKKAVE RQ.KSNPAVL PEQAKGPETK
BLAP   SFVPGEPSTQ DGNGHGTHVA GTIAALNNSI GVLGVAPSAE LYAVKVLGAD
 SB2   TYDPN.IKSD QYGLYSKAFT GTGKVNETKE KAEKKSPAKA PYSIKS....

101                                                           150
HP23   IQGSAPQVQA KANASETPVS HIGKVFFTLG GTNYVCSANS VVSTNRNTVS
BLAP   GRGAISSIAQ GLEWAGNNGM HVANLSLGSP .......SPS ATLEQAVNSA
 SB2   .VIGSDDRTR VTNTTAYPYR AIVHISSSIG .......SCT GWMIGPKTVA 151                                                           200
HP23   TAGHCLNEGP .GAFATKFTF VPAYLNGSAP YGKWTAKALY APTQWSSSGS
BLAP   TSRGVLVVAA SGNSGASSIS YPARYANAMA VGATDQNNNR ASFSQYGAGL
 SB2   TAGHCIYDTS SGSFAGTATV SPGRNGTSYP YGSVKSTRYF IPSGWRS.GN 201                                                           250
HP23   MEYDTGFAVM SQLNGRNLAD VVGASGVSFN AARGLAYKAF GYPAASPFNG
BLAP   DIVAPGVNVQ STYPGSTYAS LNGTSMATPH VAGAAALVKQ KNPSWSNVQI
 SB2   TNYDYGAIEL SEPIG.NTVG YFGYS.YTTS SLVGTTVTIS GYPGDKTAG.

251                                                           300
HP23   ESLKSCSGTA TNDPYNPQFN SQGIPCNMTG GSSGGPWFIG TSSSGYQNSV
BLAP   RNHLKNTATS LGSTNLYGS. ......GLVN AEAATR.... ..........
 SB2   TQWQHSGPIA ISETYKLQY. ....AMDTYG GQSGSPVFEQ SSSR.....T 301                                          343
HP23   NSYGYGSKST TMYGPYWGS. .......... VIQQAYNTAS SAS
BLAP   .......... .......... .......... .......... ...
 SB2      NCSGPCSLAV   HTNGVYGGSS    YNRGTRITKE    VFDNLTNWKN    SAQ
```

Figure 2

```
            1                                                          50
HP23    MTSTRTLATS  LMSLTTAALF  ALCSAGQATA  APASPDTKDV  AGVSSAAVTD
Nest.   ..........  ..........  ..........  ..........  ..........
  SB2   MVSKKSVKRG  LITGLIGISI  YSLGMHPAQA  APSPHTPVSS  DPSYKAETSV
 BLAP   ..........  ..........  .......AQS  VPWGISRVQA  PAAHNRGLTG 51                                                        100
HP23    TSGADYWTPE  RMRSAIPADV  LAKKAVERQK  SNPAVLPEQA  KGPETKIQGS
Nest.   ..........  ..........  ..........  ..........  ..........
  SB2   TYDPNIKSDQ  YGLYSKAFTG  TGKVNETKEK  AE........  ....KKSPAK
 BLAP   SGVKVAVLDT  GISTHPDLNI  RGGASFVPGE  PS........  ..........

101                                                       150
HP23    APQVQAKANA  SETPVSHIGK  VFFTLGGTNY  VCSANSVVS.  ...TNRNTVST
Nest.   .........Q  NPADSPHIGK  VFFSTNQGDF  VCSANIVAS.  ...ANQSTVAT
  SB2   APYSIKSVIG  SDDRTRVTNT  TAYPYRAIVH  ISSSIGSCTG  WMIGPKTVAT
 BLAP   .......TQD  GNGHGTHVAG  TIAALNNSIG  VLGVAPSAEL  YAVKVLGADG 151                                                       200
HP23    AGHCLNEGPG  .AFATKFTFV  PAYLNGSAPY  GKWTAKALYA  PTQWSSSGSM
Nest.   AGHCLHDGNG  GQFARNFVFA  PAYDYGESEH  GVWAAEELVT  SAEWANRGDF
  SB2   AGHCIYDTSS  GSFAGTATVS  PGRNGTSYPY  GSVKSTRYFI  PSGWRS.GNT
 BLAP   RGAISSIAQG  LEWAGNNGMH  VANLSLGSPS  PSATLEQAVN  SATSRG....

201                                                       250
HP23    EYDTGFAVMS  QLNGRNLADV  VG.ASGVSFN  AARGLAYKAF  GYPAASPFNG
Nest.   EHDYAFAVLE  TKGGTTVQQQ  VGTASPIAFN  QPRGQYYSAY  GYPAAAPFNG
  SB2   NYDYGAIELS  EPIG.NTVGY  FG..YSYTTS  SLVGTTVTIS  GYPGDKTAGT
 BLAP   ......VLVV  AASGNSGASS  ISYPARYANA  MAVGATDQNN  NRASFSQYGA 251                                                       300
HP23    ESLKSCSGTA  TNDPYNPQFN  SQGIPCNMTG  GSSGGPWFIG  TSS.....SG
Nest.   QELHSCHGTA  TNDPMG..SS  TQGIPCNMTG  GSSGGPWFLG  QGT.....GG
  SB2   QWQHSGPIAI  S...ETYK..  LQYAMDTYG.  GQSGSPVFEQ  SSSRTNCSGP
 BLAP   GLDIVAPGVN  VQSTYPG...  ..STYASLNG  TSMATPHVAG  AAALVKQKNP 301                                             338
HP23    YQNSVNSYGY  GSKSTTMYGP  YWGSVIQQAY  NTASSAS.
Nest.   AQNSVNSYGY  TFLPDVMFGP  YFGSGAQQNY  NYAST...
  SB2   CSLAVHTNGV  YGGSSYNRGT  RITKEVFDNL  TNWKNSAQ
 BLAP   SWSNVQIRNH  LKNTATSLGS  TNLYGSGLVN  AEAATR..
```

Figure 3 / Part 1

```
          1                                                           50
HP23      ..........  ..........  ..........  ..........  ..........
BLAP      ..........  ..........  ..........  ..........  ..........
  SB2     TCGACGGCTT  CCCGTGCGCC  TCCGGGATCG  CTGTGATAAT  TGACAACCAC 51                                                         100
HP23      ..........  ..........  ..........  ..........  ..........
BLAP      ..........  ..........  ..........  ..........  ..........
  SB2     ATTCATCTTT  TCTTTTCCAA  ACCGTTCTGC  AACCGCCTTG  CCTATACCTT 101                                                        150
HP23      ..........  ..........  ..........  ..........  ..........
BLAP      ..........  ..........  ..........  ..........  ..........
  SB2     TTGAAGAGCC  GGTCACAATT  GCTGTTTTTC  CTTTTAAATC  ACTATACAAC 151                                                        200
HP23      ..........  ..........  ..........  ..........  ..........
BLAP      ..........  ..........  ..........  ..........  ..........
  SB2     CTAAACACCC  CTCAATTTCT  TTTCTCCATG  TACATTACCC  GGTATCAATA 201                                                        250
HP23      ..........  ..........  ..........  ..........  ..........
BLAP      ..........  ..........  ..........  ..........  ..........
  SB2     TATGATCAAA  CAAAATGTTA  ATACACACCT  TTAGTATGAT  CTTTTTTAAA 251                                                        300
HP23      ...ATG..AC  ATCAACCAGG  ACTCTGGCCA  CAAGCCTCAT  GAGCCTCACC
BLAP      ..........  ..........  ..........  ..........  ..........
  SB2     CATATGGAAA  ATTCAGAATT  ATTTTGTTAA  TATCTAACTT  GTACTT.ACA 301                                                        350
HP23      ACCGCAGCAC  TGTTCGCCCT  CTGCTCTGCC  GGGCAGGC.G  ACGGCAGCCC
BLAP      ..........  ..........  ..........  ..........  ..........
  SB2     ACAAAATAA.  .GGAAGTGAT  ATGATTTGGT  TAGTAAAAAG  AGTGTTAAAC 351                                                        400
HP23      CCGC....AT  CGCCGGACAC  GAAGGACGTT  GCCGGCGTCA  GCAGCGCGGC
BLAP      ..........  ..........  .........G  CGCAATCAGT  GCCATGGGGA
  SB2     GAGGTTTGAT  CACAGGTCTC  ATTGGTATTT  ..CTATTTAT  TCTTTAGGTA
```

Figure 3 / Part 2

```
           401                                                             450
    HP23   CGTCACCGAC ACCAGCGGCG CCGACTACTG G.ACGCCGGA ACGCATGCGT
    BLAP   ATTAGCCGTG TGCAA..GCC CCGGCTGCCC ATAACCGTGG ATTGACAGGT
     SB2   TGCACCCGGC CCAAGCCGCG CCATCGCCTC ATACTCCTGT TT.CAAGCGA
           451                                                             500
    HP23   TCGGCCATCC CG.GCGGACG TCCTGGCCAA GAAGGCCGTG GAACGGCAGA
    BLAP   TCTGGTGTAA AAGTTGCTGT CCTCGATACA GGTATTTCCA CTCATCCAGA
     SB2   TCCTTCATAC AAAGCGGAAA CATCGGTTAC TTATGACCCA AACATTAAGA 501                                                             550
    HP23   A.GTCCAACC CGGCAGTCCT CCCGGAGCAG .....GCCAA GGGCCCGGAG
    BLAP   CTTAAATATT CGTGGTGGCG CTAGCTTTGT .....ACCAG GGGAACCATC
     SB2   GCGATCAATA CGGCTTGTAT TCAAAGCGT TTACAGGCAC CGGCAAAGTG 551                                                             600
    HP23   ACCAAAATCC AGGGCT..CC GCACCCCAGG TC.CAGGCCA AGGCCAACGC
    BLAP   CACTCAAGAT GGGAAT..GG GCATGGCACG CATGTGGCCG .GGACGATTG
     SB2   AATGAAACAA AGGAAAAAGC GGAAAAAAAG TCACCCGCCA AGCTCCTTA 601                                                             650
    HP23   CAGCGAAACC CCGGTG.... ..TCCCAC.A TCGG.CAAGG .TGTTCTTCA
    BLAP   CTGCTTTAAA CAATTC.... .....GATTG GCGTTCTTGG CGTAGCGCCT
     SB2   CAGCATTAAA TCGGTGATTG GTTCTGATGA TCGGACAAGG GTCACCAACA 651                                                             700
    HP23   CCCTCGG... .CGGCACCAA C......TAC GTCTGCTCGG CAAACTCGGT
    BLAP   AGTGCGGAA. .CTATACGCT G......TTA AAGTTTTAGG AGCCGACGGT
     SB2   CAACCGCATA TCCGTACAGA GCGATCGTTC ATATTCAAG CAGCATCGGT 701                                                             750
    HP23   GG.TGTCC.. ........AC CAACCGGAAC ACCGTCTCCA CCGCCGGCCA
    BLAP   AGAGGTGCA. ........AT CAGCTCGATT GCC....CAA GGGTTGGAAT
     SB2   TCATGCACCG GATGGATGAT CGGTCCGAAA ACCGTCGCAA CAGCCGGACA 751                                                             800
    HP23   CTGCCTCAAT GAAGGCCC.. .CGGAGCCTT CGCCACCAAG TTCACGTTCG
    BLAP   GGGCAGGGAA CAATGGCA.. ..TGCACGTT ....GCTAAT TTGAGTTTAG
     SB2   CTGCATCTAT GACACATCAA GCGGTTCATT TGCCGGTACA GCCACT...G
```

Figure 3 / Part 3

```
         801                                                    850
HP23     TTCCCGCCTA CCTGAACGGC TCCGCACCCT ACGGAAAGTG GACTGCCAAG
BLAP     GAAGCCCTTC GCCAAGTGCC AC.....ACT TGAGCAA..G ..CTGTTAA.
 SB2     TTTCGCCGGG ACGGAACGGG AC...AAGCT ATCCTTACGG CTCAGTTAAA 851                                                    900
HP23     GCGCTGTACG CCCCCACCCA GTGGAGCTCG TCAGGCAG.. .CATGGAATA
BLAP     TAGCGCGACT TCTAGAGGCG TTCTTGTTGT AGCGGCAT.. .CTGGGAATT
 SB2     TCGACGCGCT ACTTTATTCC GTCAGGATGG AGAAGCGGAA ACACCAATTA 901                                                    950
HP23     CGACACGGGC TTCGCCGTCA TGAGCCAGCT CAACGGCCGC AACCTGGCCG
BLAP     C.A....GGT GCAAGCTCAA TCAGCTATCC GGCCCGTTAT GCAACGCAA
 SB2     CGATTACGGC GCAATCGAAC TAAGCGAACC GATCGGCAAT A..CTGTCGG 951                                                   1000
HP23     ACGTCGTCGG GGCCTCCGGG GTCAGCTTCA ACGCCGCCCG CGGCCTGGCC
BLAP     TGGCAGTCGG AGCTACTGAC CAAAACAACA AC......CG CGCCAGCTTT
 SB2     ATA.CTTCGG ATACTC.GTA CACTACTTCA TCACTTGTTG GGACAACTGT 1001                                                   1050
HP23     TACAAGGCCT TCGGCTACCC GGCCGCCTCA CCGTTCAACG GCGAATCGCT
BLAP     TCACAGTATG GCGCAGGGCT TGACATTGTC GCACCAGGGG TAAACGTGCA
 SB2     TACCAT..CA GCGGCTACCC AGGCGATAAA ACAGCAGGCA CACAATGGCA 1051                                                   1100
HP23     GAAGAGCTGC TCCGGCACCG CCACCAACGA TCCCTACAAC CCGCAGTTCA
BLAP     GAGCACATAC CCAGG...TT CAACGTATGC CAGCTTAAA. ...CGGTACA
 SB2     GCATT.CAGG ACCG..ATTG CCATCTCCGA AACGTATAAA TTGCAGTAC.

1101                                                   1150
HP23     ACAGCCAAGG CATCCCCTGC AACATGACCG GCGGCTCCTC GGG...CGGA
BLAP     ...TCGATGG CTACTCCT.C ATGTTGCA.. ..GGTGCAGC AGC.......
 SB2     ...GCAATGG ACACGTACGG AGGACAAA.. GCGGTTCACC GGTATTCGAA 1151                                                   1200
HP23     CCGTGGTTCA TCGGCACCAG CTCCAGCGGT ...TACCAGA ACTCGGTCAA
BLAP     .CCTTGTTAA ACAAAAGAAC CCATCTTGGT CCAATGTACA AATCCGCAAC
 SB2     CAAAGCAGCT CCAGAACGAA CTGCAGCGGT CCGTGCTCGC TTGCCGTACA
```

Figure 3 / Part 4

```
        1201                                                           1250
HP23    CAGCTACGGC ...TACGGCA GCAAGTCC.A CCACA.ATGT ACGGCCCGTA
BLAP    CATCTAAAGA ..ATACGGCA ACGAG.CTTA GGAAGCACGA ACTTGTATGG
 SB2    CACAAATGGA GTATACGGCG GCTCCTCGTA CAACAGAGGC ACCCGGATTA 1251                                                           1300
HP23    CT.....GGG GTTC....AG TGATCCAGCA GGCGTACAAC ACCGCATCCT
BLAP    AA...GCGGA CTTG.....T CAATGCAGAA GCGG..CAAC A.CGC.....
 SB2    CAAAAGAGGT GTTCGACAAT TGACCAACT GGA..AAAAC AGCGCACAAT 1301                                                           1350
HP23    CGGCCTCTTA G......... .......... .......... ..........
BLAP    .......... .......... .......... .......... ..........
 SB2    AATACACGAA GACAGCCCGC TTCCTTTTGG AACGGGCTGT CACATCTAAC 1351                                                           1400
HP23    .......... .......... .......... .......... ..........
BLAP    .......... .......... .......... .......... ..........
 SB2    GGCCGTATAC TTAATTTCCT TTAAGCCTGT ACTTTTTGCC ATCTATTGAT 1401                                                           1450
HP23    .......... .......... .......... .......... ..........
BLAP    .......... .......... .......... .......... ..........
 SB2    ATCGTGAAAT TTGAAGGACC GCTGATCGGC AAATAATAGA CAAGCTGAAA 1451                1477
HP23    .......... .......... .......
BLAP    .......... .......... .......
 SB2    CTCCGCTTCC TCACCAGGTT TGAATGG
```

Figure 4 / Part 1

```
              1                                                    50
HP23          ..........  ..........  ..........  ..........  ..........
Nest.         ..........  ..........  ..........  ..........  ..........
  SB2         TCGACGGCTT  CCCGTGCGCC  TCCGGGATCG  CTGTGATAAT  TGACAACCAC
BLAP          ..........  ..........  ..........  ..........  ..........

51                                                   100
HP23          ..........  ..........  ..........  ..........  ..........
Nest.         ..........  ..........  ..........  ..........  ..........
  SB2         ATTCATCTTT  TCTTTTCCAA  ACCGTTCTGC  AACCGCCTTG  CCTATACCTT
BLAP          ..........  ..........  ..........  ..........  ..........

101                                                  150
HP23          ..........  ..........  ..........  ..........  ..........
Nest.         ..........  ..........  ..........  ..........  ..........
  SB2         TTGAAGAGCC  GGTCACAATT  GCTGTTTTTC  CTTTTAAATC  ACTATACAAC
BLAP          ..........  ..........  ..........  ..........  ..........

151                                                  200
HP23          ..........  ..........  ..........  ..........  ..........
Nest.         ..........  ..........  ..........  ..........  ..........
  SB2         CTAAACACCC  CTCAATTTCT  TTTCTCCATG  TACATTACCC  GGTATCAATA
BLAP          ..........  ..........  ..........  ..........  ..........

201                                                  250
HP23          ..........  ..........  ..........  ..........  ..........
Nest.         ..........  ..........  ..........  ..........  ..........
  SB2         TATGATCAAA  CAAAATGTTA  ATACACACCT  TTAGTATGAT  CTTTTTTAAA
BLAP          ..........  ..........  ..........  ..........  ..........

251                                                  300
HP23          .....ATGAC  ATCAACCAGG  ACTCTGGCCA  CAAGCCTCAT  GAGCCTC..A
Nest.         ..........  ..........  ..........  ..........  ..........
  SB2         CATATGGAAA  ATTCAGAATT  ATTTGTTAA   TATCTAACTT  GTACTTACAA
BLAP          ..........  ..........  ..........  ..........  ..........

301                                                  350
HP23          CCACCGCAGC  ACTGTTCGCC  CTCTGCTCTG  CCGGGCAGGC  GACGGCAGCC
Nest.         ..........  ..........  ..........  ..........  ..........
  SB2         CAAAATAAGG  AAGTGATATG  ATTTGGTTAG  TAAAAGAGT   GTTAAACGAG
BLAP          ..........  ..........  ..........  ..........  ..........
```

Figure 4 / Part 2

```
            351                                                    400
HP23    CCCGCATCGC CGGACACGAA GGACGTTGCC GGCGTCAGCA GCGCGGCCGT
Nest.   .......... .......... .......... .......... ..........
  SB2   GTTTGATCAC AGGTCTCATT GGTATTT..C TATTTATTCT TTAGGTATGC
 BLAP   .......... .......... .......... .......... ..........

401                                                    450
HP23    CACCGACACC AGCGGCGCCG ACTACTGGAC GCCGGAACGC ATGCGTTCGG
Nest.   .......... .......... .......... .......... ..........
  SB2   ACCCGGCCCA AGCCGCGCCA TCGCCTCATA CTCCTGTTTC AAGCGATCCT
 BLAP   .......... .......... .......... .......... ..........

451                                                    500
HP23    CCATCCCG.G CGGACGTCCT GGCCAAGAAG GCCGTGGAAC GGCAGAA.GT
Nest.   .......... .......... .......... .......... ..........
  SB2   TCATACAAAG CGGAAACATC GGTTACTTAT GACCCAAACA TTAAGAGCGA
 BLAP   .......... .......... .......... .GCGCAATCA GTGCCAT.GG 501                                                    550
HP23    CCAACCCGGC AGTCCTCCCG GAGCAGGCCA AGGGCCCGGA GACCAAAATC
Nest.   .......... .......... .......... .......... ..........
  SB2   TCAATACGGC TTGTATTCAA AAGCGTTTAC AGGCACCGGC AAAGTGAATG
 BLAP   GGAATTAGCC GTGTGCAAGC CCCGGCTGCC CATAACCGTG GATTGACAGG 551                                                    600
HP23    CAGGGCT... .....CCGCA CCCCAGGTCC AGGCCAAGGC CA.ACGCCAG
Nest.   .......... .......... .......... .........C AG.AATCCGG
  SB2   AAACAAAGGA AAAAGCGGAA AAAAAGTCAC CCGCCAAAGC TC.CTTACAG
 BLAP   TTCTGGTGTA AAAGTTGCTG TCCTCGATAC AGGTATTTCC ACTCATCCAG 601                                                    650
HP23    CGAAACCCCG GTG......T CCCAC.ATCG G.CAAGG.TG TTCTTCACCC
Nest.   CGGACTCCCC G......... C..AC.ATAG G.CAAGG.TC TTCTTCTCCA
  SB2   CATTAAATCG GTGATTGGTT CTGATGATCG GACAAGGGTC ACCAACACAA
 BLAP   ACTTAAATAT TCGTGGTGGC GCTAGCTTTG TACCAGGGGA ACCATCCACT 651                                                    700
HP23    TCGGC..... ...GGCACCA AC..TACGTC TGCTCGGCAA ACTCGGTG..
Nest.   CCAAC..... ...CAGGGCG AC..TTCGTC TGCTCCGCCA ACATCGTG..
  SB2   CCGCATATCC GTACAGAGCG ATCGTTCATA TTTCAAGCAG CATCGGTTCA
 BLAP   CAAGATGGGA ATGGGCATGG CA..CGCATG TGGCCGGGAC GATTGCTGCT
```

Figure 4 / Part 3

```
         701                                                      750
HP23   ......GTGT CCACCAAC.. .CGGAACACC GTCTCCACCG CCGGCCACTG
Nest.  ......GCCT CGGCGAAC.. .CAGTCCACG GTGGCCACCG CGGGGCACTG
  SB2  TGCACCGGAT GGATGATCGG TCCGAAAACC GTCGCAACAG CCGGACACTG
 BLAP  TTAAACAATT CGATTGGCGT TCTTGGCGTA GCGCCTAGTG CGGAACTATA 751                                                      800
HP23   CCTCAATGAA GGCCCCGGAG CC...TTCGC CAC...CAA.. .GTTCACGTT
Nest.  CCTGCACGAC GGAAACGGCG GCCAGTTCGC ACG...CAA.. .CTTCGTCTT
  SB2  CATCTATGAC ACATCAAGCG GTTCATTTGC CGGTACAG... .CCACTGTTT
 BLAP  CGCTGTTAAA GTTTTAGGAG CCGACGGTAG AGGTGCAATC AGCTCGATTG 801                                                      850
HP23   CGTTCCCGCC TACCTGAACG GCTCCGCACC CTACGGAAAG TGGACTGCCA
Nest.  CGCCCCTGCC TACGACTACG GCGAGTCCGA GCACGGCGTG TGGGCCGCAG
  SB2  CGCCGGGACG GAACGGGACA AGCTATCC.. TTACGGC.TC AGTTAAATCG
 BLAP  CCCAAGGGTT GGAATGGGCA GGGAACAATG GCATGCACGT TGCTAATTTG 851                                                      900
HP23   AGGCGCTGTA CGCCCCCACC CAGTGGAGCT CGTCAGGCAG CATGGAATAC
Nest.  AAGAGCTGGT GACCTCCGCC GAGTGGGCGA ACCGCGGCGA CTTCGAGCAT
  SB2  ACGCGCTACT TTATTCCGTC AGGATGGAGA A..GCGGAAA CACCAATTAC
 BLAP  AGTTTAGGAA GCCCTTCGCC AAGTGCCACA CTTGAGCAAG CTGTTAATAG 901                                                      950
HP23   GACACGGGCT T.CGCCGTCA TGAGCC.AGC TCAACGGCCG CA..ACCTGG
Nest.  GACTACGCCT T.CGCGGTCC T...CG.AGA CCAAGGGCGG CACCACCGTG
  SB2  GATTACGGCG C.AATCGAAC TAAGCG.AAC CGATCGGCAA TAC.....TG
 BLAP  CGCGACTTCT AGAGGCGTTC TTGTTGTAGC GGCATCTGGG AATTCAGGTG 951                                                     1000
HP23   CCGACGTCGT CGGGGCCTCC GGGG....TC AGCTTCAACG CCGCCCGCGG
Nest.  CAGCAGCAGG TGGGACGGC GTCGCCGATC GCCTTCAACC AGCCGCGCGG
  SB2  TCGGATACTT CGGATACTCG TACA.....C TACTTCATCA CTTGTTGGGA
 BLAP  CAAGCTCAAT CAGCTATCCG GCCC.....G TTATGCGAAC GCAATGGCAG 1001                                                     1050
HP23   CCTGGCCTAC AA.GGCCTTC GGCTACCCGG CCGCCTCACC GTTAACGGC
Nest.  CCAGTACTAC AG.CGCCTAC GGCTACCCGG CCGCCGCGCC CTTCAACGGC
  SB2  CAACTGTTAC ...CATCAGC GGCTACCCAG GCGATAAAAC AGCAGGCACA
 BLAP  TCGGAGCTAC TGACCAAAAC AACAACCGCG CCAGCTTTTC ACAGTATGGC
```

Figure 4 / Part 4

```
         1051                                                    1100
   HP23  GAATCGCTGA AGAGCTGCTC CGGCACCGCC ACCAACGATC CCTACAACCC
  Nest.  CAGGAGCTCC ACAGCTGCCA CGGCACCGCC ACGAACGACC ....CGATGG
    SB2  CAATGGCAGC ATT.CAGGAC CG..ATTGCC ATCTCCGAAA CGTATAAATT
   BLAP  GCAGGGCTTG ACA.TTGT.. CG.......C ACCAGGGGTA .....AACGT 1101                                                    1150
   HP23  GCAGTTCAAC AGCCAAGGCA TCCCCTGCAA CATGACCG.G CGGCTCCTCG
  Nest.  GCAG..CAGC ACTCAGGGCA TCCCGTGCAA CATGACCG.G CGGCTCCTCC
    SB2  GCAG.....T ACGCAATGGA .CACGTACGG .AGGACAAAG CGGTTCACCG
   BLAP  GCAGAGCACA TACCCAGGTT CAACGTATGC CAGCTTAA.A CGGTACATCG 1151                                                    1200
   HP23  GG...CGGAC CGTGGTTCAT CGGCACCAGC TCCAGCGGTT A....CCAGA
  Nest.  GG...CGGCC CCTGGTTCCT CGGTCAGGGG ACCGGCGGTG C....CCAGA
    SB2  GTATTCGAAC AAAGCAGCTC CAGAACGAAC TGCAGCGGTC CGTG.CTCGC
   BLAP  ATGG.CTACT CCTCATGTTG CAGGTGCAGC AGCCCTTGTT AAACAAAAGA 1201                                                    1250
   HP23  ACTCGGTCAA CAGCTACGGC ...TACGGCA GCAAGTCCAC CACAATGTAC
  Nest.  ACTCTGTGAA CTCCTACGGG ...TACACCT TCCTGCCGGA CGTGATGTTC
    SB2  TTGCCGTACA CACAAATGGA GTATACGGCG GCTCCTCGTA CAACA.GAGG
   BLAP  ACCCATCTTG GTCCAATGTA ...CAAATCC GCAACCATCT AAAGAATACG 1251                                                    1300
   HP23  GGCCCGTACT GGGGTTCAGT GATCCAGCA. ...GGCGTAC ......AACA
  Nest.  GGGCCGTACT TCGGCTCCGG GGCACAGCA. ...GAACTAC ......AACT
    SB2  CACCCGGATT ACAAAGAGG TGTTCGACAA TTTGACCAAC TGGAAAAACA
   BLAP  GCAACGAGCT TAGGAAGCAC GAACTTGTAT GGAAGCGGAC T....TGTCA 1301                                                    1350
   HP23  CCGCATCCTC GGCCTCTTAG .......... .......... ..........
  Nest.  ACGCCTCCAC A......... .......... .......... ..........
    SB2  GCGCACAATA ATACACGAAG ACAGCCCGCT TCCTTTTGGA ACGGGCTGTC
   BLAP  ATGCAGAAGC GGCAACACGC .......... .......... ..........

1351                                                    1400
   HP23  .......... .......... .......... .......... ..........
  Nest.  .......... .......... .......... .......... ..........
    SB2  ACATCTAACG GCCGTATACT TAATTTCCTT TAAGCCTGTA CTTTTTGCCA
   BLAP  .......... .......... .......... .......... ..........
```

Figure 4 / Part 5

```
       1401                                                    1450
HP23   ..........  ..........  ..........  ..........  ..........
Nest.  ..........  ..........  ..........  ..........  ..........
  SB2  TCTATTGATA  TCGTGAAATT  TGAAGGACCG  CTGATCGGCA  AATAATAGAC
BLAP   ..........  ..........  ..........  ..........  ..........

1451                              1486
HP23   ..........  ..........  ..........  ......
Nest.  ..........  ..........  ..........  ......
  SB2  AAGCTGAAAC  TCCGCTTCCT  CACCAGGTTT  GAATGG
BLAP   ..........  ..........  ..........  ......
```

ALKALINE PROTEASE AND WASHING AND CLEANING PRODUCTS CONTAINING SAID NOVEL ALKALINE PROTEASE

CROSS REFERENCE TO RELATED APPLICATIONS

This application is a §365 (c) continuation application of PCT/EP2004/014333 filed 16 Dec. 2004, which in turn claims priority to DE Application 103 60 805.2 filed 23 Dec. 2003, each of the foregoing applications is incorporated herein by reference.

FIELD OF THE INVENTION

The present Application relates to a novel alkaline protease encoded by DNA obtained from a soil sample, to orthologs and homologs thereof, proteases encoded by the same and to industrial applications for such proteases, especially their utilization in washing and cleaning products.

BACKGROUND OF THE INVENTION

Proteases are among the most technologically significant of all enzymes. Among them, proteases of the subtilisin type (subtilases, subtilopeptidases, EC 3.4.21.62), which comprise catalytically active amino acids, also referred to as serine proteases, are particularly important. Acting as non-specific endopeptidases, they hydrolyze any acid-amide bonds that are located inside peptides or proteins. Their optimum pH is usually in the distinctly alkaline range. An overview of this family of proteases can be found in "Subtilases: Subtilisin-like Proteases," by R. Siezen, pp. 75-95 in "Subtilisin enzymes," edited by R. Bolt and C. Betzel, New York, 1996. Subtilases are formed naturally by microorganisms. Among these, the subtilisins formed and secreted by *Bacillus* species comprise a very significant group within the subtilases.

Proteases, along with other enzymes, are well-established active ingredients present in washing and cleaning products which cause the breakdown of protein-containing stains on the material being cleaned. Ideally, synergistic effects occur between the enzymes and the other constituents of the relevant products. Among the washing and cleaning product proteases, subtilases occupy a prominent position because of their favorable enzymatic properties such as stability or optimum pH. In addition, they are also suitable for a large number of other industrial application possibilities, for example as constituents of cosmetics or in organic chemical synthesis.

The conventional procedure for obtaining new enzymes is to take microorganism-containing samples from natural habitats and culture them in conditions considered to be suitable, (e.g., in an alkaline environment). This yields enriched microorganism cultures that, with a certain probability, also contain enzymes (including alkaline proteases) that are active under the relevant conditions. The microorganisms having the highest-performance enzymes are then selected and purified, (e.g., by plating out onto protein-containing agar plates and measuring the zone of lysis formed). Once isolated, the relevant protease gene is then cloned.

A procedure of this kind is described, for example, in the textbook "Alkalophilic Microorganisms. A New Microbial World," by K. Horikbshi and T. Akiba (1982), Japan Scientific Societies Press, Springer-Verlag, New York, Heidelberg, Berlin, ISBN 0-387-10924-2, Chapter 2, pp. 9-26. WO 00/24882 A1 also, discloses a method for producing a gene bank that comprises nucleic acids isolated from microorganism-containing samples from different habitats, (e.g., from the rumen), which are cultured under the conditions of interest and thereby enriched. Nucleic acids of interest are then isolated therefrom and cloned.

Alkaline proteases formed naturally, preferably microbially, have already been used in washing and cleaning products. According to Application WO 93/07276 A1, for example, the protease 164-A1 of Chemgen Corp., Gaithersburg, Md., USA, and Vista Chemical Company, Austin, Tex., USA, obtainable from *Bacillus* spec. 164-A1, is suitable for use in washing and cleaning products. Other examples are the alkaline protease from *Bacillus* sp. PD138, NCIMB 40338 of Novozymes A/S, Bagsvaerd, Denmark, (WO 93/18140 A1), the proteinase K-16 of Kao Corp., Tokyo, Japan deriving from *Bacillus* sp. ferm. BP-3376 (U.S. Pat. No. 5,344,770) and, according to WO 96/25489 A1, (Procter & Gamble, Cincinnati, Ohio, USA), the protease from the psychrophilic organism *Flavobacterium balustinum*.

Natural proteases are optimized for use in washing and cleaning products, by way of known mutagenesis methods. These include point mutagenesis, deletion, insertion, or fusion with other proteins or protein parts, or alternative modifications. The strategy of introducing deliberate point mutations into a known molecule in order to improve the washing performance of subtilisins is also referred to as "rational protein design." A similar performance improvement strategy consists of modifying the surface charges and/or the isoelectric point of the molecules, and thereby modifying their interactions with the substrate. Using point mutations, for example, the net charge of the subtilisins can be modified in order to influence substrate binding in particular for use in washing and cleaning products. A further, supplementary strategy consists of increasing the stability of the relevant proteases and thus increasing their effectiveness. Stabilization via coupling to a polymer is described for proteases used in cosmetics, for example, in U.S. Pat. No. 5,230,891 as they are associated with better skin compatibility. For washing and cleaning products in particular, stabilization by way of point mutation introduction is more common.

One modern trend in enzyme development is to combine elements from known related proteins, using statistical methods, to yield new enzymes having properties not hitherto achieved. Such methods are also grouped under the general term "directed evolution." These include, for example, the following methods: the StEP method (Zhao et al. (1998), *Nat. Biotechnol.*, Vol. 16, pp. 258-261); random priming recombination (Shao et al., (1998), *Nucleic Acids Res.*, Vol. 26, pp. 681-683); DNA shuffling (Stemmer, W. P. C. (1994), *Nature*, Vol. 370, pp. 389-391); or RACHITT (Coco, W. M. et al. (2001), *Nat. Biotechnol.*, Vol. 19, pp. 354-359). A further shuffling method referred to as a "recombining ligation reaction" (RLR) is described in WO 00/09679 A1.

An overview of the industrially most important alkaline proteases of the subtilisin type will be provided below. Subtilisin BPN', which derives from *Bacillus amyloliquefaciens* or *B. subtilis*, is known from the work of Vasantha et al. (1984) in *J. Bacteriol.*, Volume 159, pp. 811-819, and of J. A. Wells et al. (1983) in *Nucleic Acids Research*, Volume 11, pp. 7911-7925. Subtilisin BPN' serves as a reference enzyme for the subtilisins, especially in terms of position numbering.

For example, the position of point mutations in subtilisin described in Application EP 251446 A1, are indicated using the numbering of BPN' as a reference. Procter & Gamble Corp., of Cincinnati, Ohio, USA, refer to this material as "Protease B." The BPN' variants of Application EP 199404 A1 are referred to by Procter & Gamble Corp. as "Protease A." "A Protease C" is in turn characterized, according to Application WO 91/06637 A1, by further point mutations of BPN'. "Protease D" refers, according to WO 95/10591 A1, to variants of the protease from *Bacillus lentus*.

The protease subtilisin Carlsberg is described in the publications of E. L. Smith et al. (1968) in *J. Biol. Chem.*, Volume 243, pp. 2184-2191, and of Jacobs et al. (1985) in *Nucl. Acids Res.*, Volume 13, pp. 8913-8926. It is formed naturally by *Bacillus licheniformis*, and was and is obtainable under the trade name Maxatase® from Genencor International Inc., Rochester, N.Y., USA, and under the trade name Alcalase® from Novozymes A/S, Bagsvaerd, Denmark.

Protease PB92 is produced naturally by the alkalophilic bacterium *Bacillus* nov. spec. 92 and is obtainable under the trade name Maxacal® from the Gist-Brocades company, Delft, Netherlands. It is described in: its original sequence in Patent Application EP 283075 A2.

Subtilisins 147 and 309 are marketed under the trade names Esperase® and Savinase®, respectively, by Novozymes. They were originally obtained from *Bacillus* strains that are disclosed by Application GB 1243784 A.

Subtilisin DY was originally described by Nedkov et al. 1985 in *Biol. Chem Hoppe-Seyler*, Volume 366, pp. 421-430.

The alkaline protease from *B. lentus* is an alkaline protease from *Bacillus* species and is described in Application WO 91/02792 A1. It natively possesses comparatively good stability with respect to oxidation and the action of detergents. Application WO 91/02792 A1 and Patents EP 493398 B1 and U.S. Pat. No. 5,352,604 describe its heterologous expression in the host *B. licheniformis* ATCC 53926. The claims of the aforesaid US Patent refer to positions 208, 210, 212, 213, and 268 as characteristic of the *B. lentus* alkaline protease; they correspond, in the numbering of the mature protein, to positions 97, 99, 101, 102, and 157. However this enzyme differs from the mature subtilisin 309 (Savinase®). The three-dimensional structure of this enzyme is described in the publication of Goddette et al. (1992) in *J. Mol. Biol., Volume* 228, pp. 580-595: "The crystal structure of the *Bacillus lentus* alkaline protease, Subtilisin BL, at 1.4 Å resolution." Industrially important variants of this enzyme that are stabilized by point mutagenesis and are suitable in particular for use in washing and cleaning products are disclosed, inter alia, in Applications WO 92/21760 A1, WO 95/23221 A1, WO 02/088340 A2, and WO 03/038082 A2.

Application DE 19857543 A1, for example, discloses liquid to gelled washing and cleaning products having proteases such as those disclosed in WO 95/23221 A1.

The enzyme thermitase, formed naturally by *Thermoactinomyces vulgaris*, was originally described by Meloun et al. (*FEBS Lett.* 1983, pp. 195-200). This is a molecule that as a whole exhibits substantial sequence discrepancies compared with the other subtilisins. The homology between the mature thermitase and the alkaline protease proteins from *B. lentus* DSM 5483 (see below) is not very high, (e.g., 45% identity; 62% similar amino acids).

Proteinase K is also a protease that exhibits comparatively low homology with the alkaline protease from *B. lentus*: only 33% identity (46% similar amino acids) at the level of the mature proteins. Proteinase K derives originally from the microorganism *Tritirachium album* Limber, and has been described by K.-D. Jany and B. Mayer (1985) in *Biol. Chem. Hoppe-Seyler*, Vol. 366, pp. 485-492.

WO 88/07581 A1 discloses proteases TW3 and TW7, which are very similar to one another, for use inter alia in washing and cleaning products.

Bacillopeptidase F from *Bacillus subtilis* possesses only 30% identity to the *B. lentus* alkaline protease at the amino-acid level. This enzyme is discussed in the aforementioned work by Siezen et al., but has not hitherto been described or claimed for use in washing and cleaning products.

Application WO 01/68821 A2 describes new subtilisins having good performance with respect to egg stains.

Further alkaline proteases that are formed from microorganisms that can be isolated from natural habitats are described in Applications WO 03/054185 A1 (from *Bacillus gibsonii* (DSM 14391)), WO 03/056017 A2 (from *Bacillus* sp. (DSM 14390)), WO 03/055974 A2 (from *Bacillus* sp. (DSM 14392)), and WO 03/054184 A1 (from *Bacillus gibsonii* (DSM 14393)). All these Applications also disclose corresponding washing and cleaning products containing these novel alkaline proteases.

Application WO 2004/085639 A1 discloses a serine protease having maximum activity at a pH of 10, from the microorganism *Nesterenkonia* sp. nov. strain (DSM 15380), together with the gene that codes for it.

A further group of industrially important proteases is represented by the metalloproteases, which require a metal cation as a cofactor. Representatives thereof may also be allocated to the family of the subtilases. Application US 2003/0113895 A1, for example, describes metalloproteases from Gram-positive microorganisms such as *B. subtilis*, but also from *S. cerevisiae, S. pombe, E. coli*, and *H. influenzae*. Washing and cleaning products having metalloproteases are disclosed, for example, by Applications WO 00/60042 A1 and WO 02/36727 A1. In the latter, a specific calcium concentration must be maintained in order to guarantee its activity in the products. Lastly, Application EP 1288282 A1 discloses a mixture of a serine protease and a metalloprotease in dishwashing products.

Further known proteases are the enzymes obtainable under the trade names Durazym®, Relase®, Everlase®, Nafizym, Natalase®, and Kannase® from Novozymes, under the trade names Maxapem®, Purafect®, Purafect OxP®, and Properase® from Genencor, under the trade name Protosol® from Advanced Biochemicals Ltd., Thane, India, and under the trade name Wuxi® from Wuxi Snyder Bioproducts Ltd., China.

As demonstrated by all these efforts performed over a long period of time, a great demand exists for industrially usable proteases that differ—in some cases drastically, in others only at a few positions—from previously known proteases. Such proteases cover a broad spectrum of performance differences, relevant to their use in washing and cleaning products, which in turn represents a large application sector. A suitable protease for washing or cleaning products is thus preferably distinguished by a certain insensitivity to the corresponding conditions (such as the presence of inherently denaturing surfactants, bleaches, high temperatures, etc.), and by good performance with respect to corresponding substrates such as, for example, the proteins present in food residues.

It is equally evident that there still exists an undiminished demand for novel alkaline proteases that are immediately usable per se and that can be further specifically optimized by way of site directed mutagenesis. Such novel proteases are of particular interest in light of the shuffling technologies that have very recently been established. Nucleotide sequences (even if the relevant enzyme itself happens to afford comparatively modest performance) can be shuffled to produce new variants and thus in turn provide entirely new artificial enzymes for use in a variety of industrial applications.

SUMMARY OF THE INVENTION

In accordance with the present invention, novel alkaline proteases are provided which naturally bring about an improvement in the performance of washing or cleaning products.

Also included in the scope of the invention are methods for isolating such proteases. Further objects include provision of nucleic acids that encode such proteases and isolated proteases produced by expression of the same. Yet another object entails genetic-engineering such nucleic acids to develop improved proteases (e.g., by a shuffling procedure). The proteases obtained by the expression of the engineered nucleic acids also comprise an aspect of the invention. Such proteases may be used to advantage in washing and cleaning products, corresponding washing and cleaning methods, and corresponding methods and application capabilities for such proteases. The proteases described herein may also be employed in industrial applications.

BRIEF DESCRIPTION OF THE DRAWINGS

FIG. 1: Alignment of the alkaline protease according to the present invention (SEQ ID NO. 4) with the alkaline proteases of the existing art (SEQ ID NO. 6 and 8), calculated using the program Vector NTI Suite ver. 7 (InforMax, Inc. Bethesda, Md., USA) under standard parameters. HP23: Alkaline protease according to the present invention, in accordance with SEQ ID NO. 4; BLAP: Alkaline protease from *Bacillus lentus* DSM 5483 (WO 92/21760 A1) in accordance with SEO ID NO. 6; SB2: Glutamate-specific endopeptidase of the S2B family, from *B. licheniformis* (GenBank access no. P80057) in accordance with SEQ ID NO. 8.

FIG. 2: Alignment of the alkaline protease according to the present invention (SEQ ID NO. 4) with the alkaline proteases of the existing art (SEQ ID NO. 6, 8 and 10). HP23: Alkaline protease according to the present invention, in accordance with SEQ ID NO. 4; Nest.: Alkaline protease from *Nesterenkonia* sp. Nov. (WO 2004/085639 A1) in accordance with SEQ ID NO. 10; SB2: Glutamate-specific endopeptidase of the S2B family, from *B. licheniformis* (GenBank access no. P80057) in accordance with SEQ ID NO. 8; BLAP: Alkaline protease from *Bacillus lentus* DSM 5483 (WO 92/21760 A1) in accordance with SEQ ID NO. 6. This alignment was calculated using the same program as that of FIG. 1, under the same standard parameters. Inclusion of the additional sequence (Nest.) results in certain discrepancies in the allocation of homologous positions. The two solutions must be regarded as equivalent.

FIG. 3: Alignment of the gene of the alkaline protease according to the present invention (SEQ ID NO. 3) with those of alkaline proteases of the existing art (SEQ ID NO. 5 and 7), calculated using the program Vector NTI Suite ver. 7 (InforMax, Inc. Bethesda, Md., USA) under standard parameters. HP23: Gene of the alkaline protease according to the present invention, in accordance with SEQ ID NO. 3; BLAP: Gene of the alkaline protease from *Bacillus lentus* DSM 5483 (WO 92/21760 A1) in accordance with SEQ ID NO. 5; SB2: Gene of the glutamate-specific endopeptidase of the S2B family, from *B. licheniformis* (GenBank access no. D10060) in accordance with SEQ ID NO. 7.

FIG. 4: Alignment of the gene of the alkaline protease according to the present invention (SEQ ID NO. 3) with those of alkaline proteases of the existing art (SEQ ID NO. 5, 7 and 9). HP23: Alkaline protease according to the present invention, in accordance with SEQ ID NO. 3; Nest.: Alkaline protease from *Nesterenkonia* sp. Nov. (WO 2004/085639 A1) in accordance with SEQ ID NO. 9; SB2: Gene of the glutamate-specific endopeptidase of the S2B family, from *B. licheniformis* (GenBank access no. D10060) in accordance with SEQ ID NO. 7; BLAP: Gene of the alkaline protease from *Bacillus lentus* DSM 5483 (WO 92/21760 A1) in accordance with SEQ ID NO. 5. This alignment was calculated using the same program as that of FIG. 3, under the same standard parameters. Inclusion of the additional sequence (Nest.) results in certain discrepancies in the allocation of homologous positions. The two solutions must be regarded as equivalent.

Figure 5:
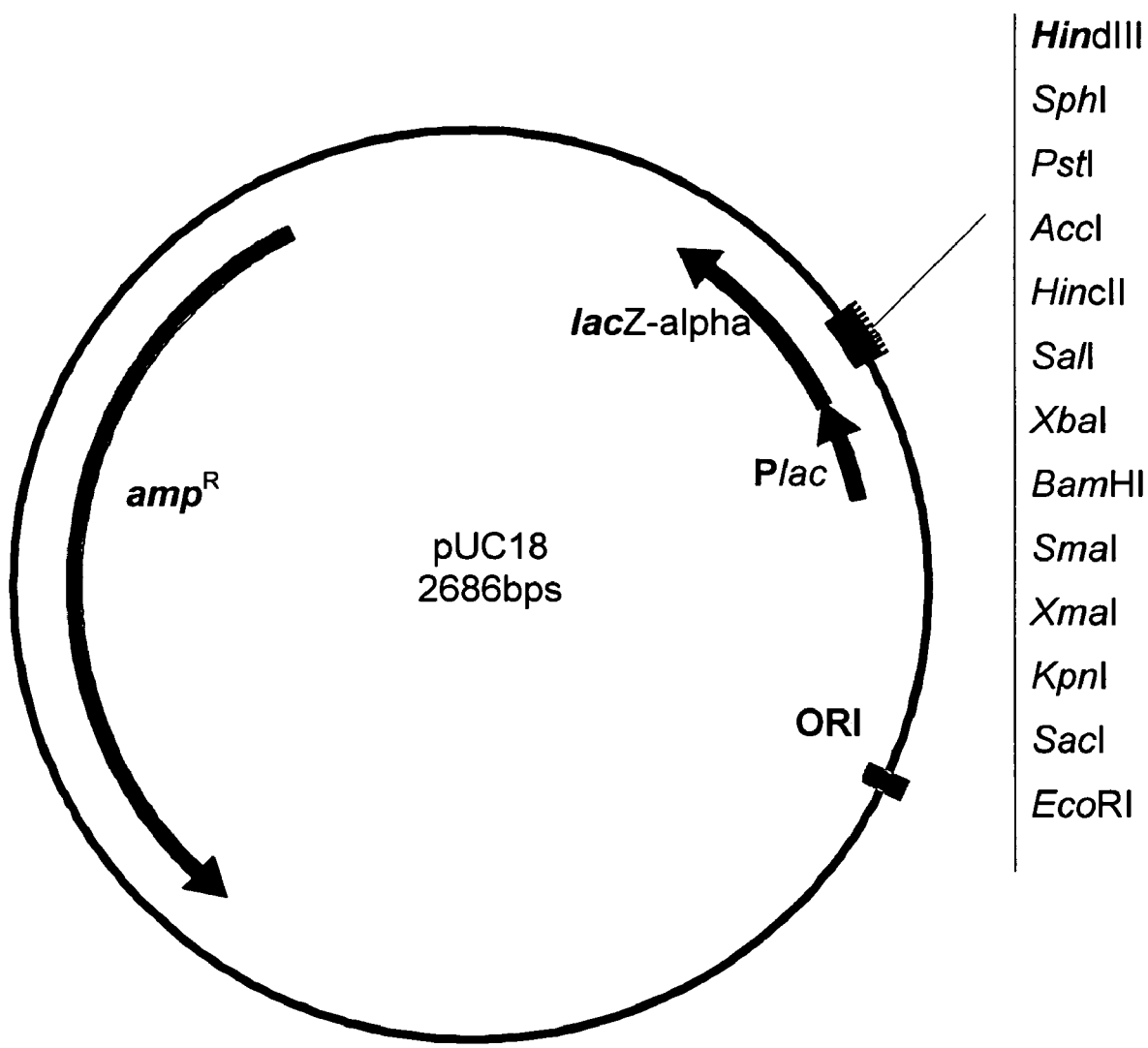
FIG. 5: Schematic depiction of the plasmid vector pUC18 used to set up an expression gene back in accordance with Example 2. The vector was linearized with Sma I for reception of the metagenomic DNA, digested with Alu I, in the indicated cloning location.

ORI: Replication origin; Plac: Promoter of the lactose operon from *E. coli*, lacZ-alpha: lacZ gene of the lactose operon from *E. coli* (coding for the alpha peptide of β-galactosidase); and ampR: Beta-lactamase transmitting ampicillin resistance.

DETAILED DESCRIPTION OF THE INVENTION

A novel approach which avoided conventional enrichment cultures for alkalophilic microorganisms was employed. A pool of protease encoding nucleic acids was isolated directly (i.e. without detouring through the isolation of strains) from soil samples. Because the relevant nucleic acids cannot be allocated as to a strain of origin, i.e. a specific genome, this approach is referred to as metagenomic DNA isolation.

Using this approach, alkaline proteases having an amino-acid sequence that is at least 40% identical to the amino-acid sequence indicated in SEQ ID NO. 4 have been obtained.

Associated therewith as further objects of the invention are the pertinent nucleic acids, corresponding natural cells, suitable methods for their identification, in particular molecular-biological methods and method elements based on the nucleic acids, as well as products, washing and cleaning products, washing and cleaning methods, and application capabilities characterized by way of the relevant proteases.

As the Examples demonstrate, the enzyme encoded by SEQ ID NO. 4 exhibits proteolytic activity that is suitable for use in washing and cleaning products. This is unexpected for a metalloprotease, since cations, which are required as cofactors, can be complexed by typical washing-product ingredients (e.g., builders) and thus become unavailable to the enzyme. Based on the DNA made available, an additional optimization of this enzyme is possible by way of, for example, further point mutations. This DNA can moreover be subjected to shuffling protocols and thereby used to generate completely novel proteases.

DEFINITIONS

For purposes of the present Application, a protein is to be understood as a polymer that is assembled from the natural amino acids, has a largely linear structure, and usually assumes a three-dimensional structure in order to perform its function. In the present Application, the 19 naturally occurring proteinogenic L-amino acids are designated using the internationally accepted one- and three-letter codes. A combination of one of these designations with a number indicates, for the respective protein, which amino-acid radical it carries in the respective position. Analogous designations have been established for point mutations. Unless otherwise stipulated, point indications refer to the respective mature forms of the relevant proteins, i.e. without the signal peptides (see below).

An enzyme is to be understood for purposes of the present Application as a protein that performs a specific biochemical function. Proteolytic enzymes or enzymes having a proteolytic function, for example, are to be understood generally as those that hydrolyze the acid-amide bonds of proteins.

Numerous proteins are formed as so-called preproteins, i.e. together with a signal peptide. The latter is then to be understood as the N-terminal portion of the protein, whose function usually consists in ensuring transfer of the protein, once formed, out of the producing cell into the periplasma or the surrounding medium, and/or correct folding thereof. Under natural conditions, the signal peptide is then cleaved off from the rest of the protein by a signal peptidase, so that the protein exerts its actual catalytic activity without the N-terminal amino acids that were initially present.

For industrial applications, the mature peptides (i.e. the enzymes processed after their production) are preferred, because of their enzymatic activity, over the preproteins.

Proproteins are inactive precursors of proteins. Their parents having a signal sequence are referred to as preproproteins.

Nucleic acids are to be understood, for purposes of the present Application, as the molecules, constructed naturally from nucleotides and serving as information carriers, that code for the linear amino-acid sequence in proteins or enzymes. They can be present as a single strand, as a single strand complementary to the latter single strand, or as a double strand. The nucleic acid DNA, constituting the naturally more durable information carrier, is preferred for molecular-biological work. For implementation of the invention in a natural environment, however, such as e.g. in an expressing cell, an RNA is formed; RNA molecules that are essential to the invention therefore also represent embodiments of the present invention. From them in turn, cDNA molecules can be derived by, for example, reverse transcription.

The nucleic-acid information unit corresponding to a protein is also referred to, for purposes of the present Application, as a gene. In DNA, the sequences of both complementary strands are to be taken into account in all three possible reading patterns in each case. Consideration is also to be given to the fact that different codon triplets can code for the same amino acids, so that a specific amino-acid sequence can be derived from multiple different nucleotide sequence that possibly exhibit little identity (genetic code degeneracy). In addition, various organisms exhibit differences in how these codons are used. For these reasons, both amino-acid sequences and nucleotide sequences must be included in consideration of the range of protection, and the nucleotide sequences that are indicated must be regarded in each case as only an exemplifying coding for a specific amino-acid sequence.

It is possible for one skilled in the art, by way of methods commonly known nowadays such as, for example, chemical synthesis or the polymerase chain reaction (PCR), in combination with standard methods of molecular biology and/or protein chemistry, to produce complete genes on the basis of known DNA sequences and/or amino-acid sequences. Such methods are known, for example, from the "Lexikon der Biochemie" [Lexicon of biochemistry], Spektrum Akademischer Verlag, Berlin, 1999, Volume 1, pp. 267-271 and Volume 2, pp. 227-229. This is possible in particular when access to a strain deposited in a strain collection is available. From such strains it is possible, for example, using PCR primers that are synthesizable on the basis of a known sequence, and/or via isolated mRNA molecules, to synthesize, clone, and, if desired, further process (e.g. mutagenize) the relevant genes.

Modifications to the nucleotide sequence, such as those that can be brought about, for example, using molecular-biological methods known per se, are referred to as mutations. Known types are, for example, depending on the nature of the change, deletion, insertion, or substitution mutations, or those in which different genes or portions of genes are fused with one another (shuffling); these are gene mutations. The associated organisms are referred to as mutants. The proteins derived from mutated nucleic acids are referred to as variants. For example, fusions and deletion, insertion, or substitution mutations result in fusion genes or deletion-, insertion-, or substitution-mutated genes and, on the protein level, in corresponding fusion proteins or deletion, insertion, or substitution variants, respectively For the description of point mutations that involve exactly one amino-acid position (amino-acid exchanges), the following convention is used: first the naturally present amino acid is designated in the form of the internationally accepted one-letter code, followed by the relevant sequence position, and lastly the inserted amino acid. Multiple exchanges within the same polypeptide chain are separated from one another by slashes.

For purposes of the present invention, vectors are understood as elements, made up of nucleic acids, that contain a gene of interest as a characterizing nucleic-acid region. They enable the gene to be established in a species or a cell line over multiple generations or cell divisions, as a stable genetic element replicating independently of the rest of the genome. Vectors conventionally used in bacteria are referred to as plasmids, i.e. circular genetic elements. A distinction is made in genetic engineering on the one hand between those vectors (so-called cloning vectors) that serve for storage and thus also to a certain extent for genetic-engineering work, and on the other hand those that used for expressing the gene of interest in the host cell, i.e. enabling expression of the relevant protein. These vectors are referred to as expression vectors.

Both bacterial cells and eukaryotic cells that contain said vectors are referred to generally, regardless of their differences, as cells. Cells that contain a vector, in particular an expression vector, and can thus be stimulated to express a transgene, are referred to as host cells, since they play host to the relevant genetic system.

Nucleic-acid or amino-acid sequences are often subjected to homology comparisons with known genes or proteins. It is performed, for example, by way of an alignment. The measure of homology is a percentage identity, as can be measured, for example, according to the method described by D. J. Lipman and W. R. Pearson in *Science* 227 (1985), pp. 1435-1441. This is preferably done using algorithms that are now applied by commercially obtainable computer programs. These include, for example, the program, Vector NTI® Suite 7.0, obtainable from InforMax, Inc., Bethesda, USA, preferably using the predefined default (i.e. standard) parameters. The homology indication can refer to the entire protein or to particular regions within the protein. An additionally defined homology term, similarity, also takes into consideration conserved variations, i.e. amino acids having similar chemical activity, since they usually perform similar chemical activities within the protein. Only the identity percentage is used in the context of nucleic acids.

Homology comparisons make it possible to deduce, from the amino-acid or nucleotide sequence, the functions of individual sequence regions as well as the enzymatic activity of the entire coding region being considered. Homologous regions of different proteins are those having comparable functions, which can be recognized by way of identity or conserved exchanges in the primary amino-acid sequence. They range from individual amino acids to very small regions (so-called domains) that are a few amino acids long, to long regions in the primary amino-acid sequence. Also to be understood as functions of the homologous regions are therefore very small sub-functions of the function performed by the entire protein, for example the formation of individual hydrogen bridge bonds in order to complex a substrate or a transition complex. Other regions of the protein that are not participants in the actual enzymatic reaction can modify the reaction qualitatively or quantitatively. This applies in particular to enzyme stability, activity, reaction conditions, or substrate specificity.

The term "proteolytic enzyme" or protease is therefore understood to embrace not only the functions of the few amino-acid radicals of the catalytically active center, but additionally all functions that result from the action of the entire remainder of the protein, or of a part or several parts of the remainder of the protein, on the actual catalytically active regions. It is furthermore possible for the activities of other proteases also to be qualitatively or quantitatively modified by one or more parts, for example, of the protein according to the present invention. This influence on other factors is likewise regarded as proteolytic activity. Proteolytically active enzymes are also those proteases whose activity is blocked at a given point in time, e.g. by an inhibitor. What is critical is their suitability in principle for the corresponding proteolysis reaction.

Fragments are understood to be all proteins or peptides that are smaller than natural proteins or those that correspond to completely translated genes, and can also, for example, be obtained synthetically. They can be associated with the relevant complete proteins on the basis of their amino-acid sequences. They can, for example, assume similar structures or exert proteolytic activities or sub-activities. Fragments and deletion variants of starting proteins are similar in principle, but whereas fragments tend to represent smaller pieces, deletion mutants tend only to lack short regions, and therefore only individual sub-functions.

Chimeric or hybrid proteins are to be understood, for purposes of the present Application, as those proteins assembled from elements that derive naturally from different polypeptide chains from the same organism or from different organisms. This procedure is also called shuffling or fusion mutagenesis. The purpose of such a fusion is, for example, to bring about or modify an enzymatic function with the aid of the fused-on protein portion.

Proteins obtained by insertion mutation are understood to be those variants that have been obtained, by way of methods known per se, by inserting a nucleic-acid or protein fragment into the starting sequence. They may be classified as chimeric proteins because of their similarity in principle, differing from them only in terms of the relationship between the size of the unmodified protein portion and the size of the entire protein. The proportion of foreign protein in such insertion-mutated proteins is smaller than it is in chimeric proteins.

Inversion mutagenesis, i.e. a partial sequence inversion, can be regarded as a special instance of both deletion and insertion. The same applies to a regrouping, deviating from the original amino-acid sequence, of different molecule parts. Such a regrouping can be regarded as a deletion variant, as an insertion variant, and as a shuffling variant of the original protein.

Derivatives are understood, for purposes of the present invention, as those proteins whose pure amino-acid chain has been chemically modified. Such derivatization operations can be performed, for example, biologically by the host organism in conjunction with protein biosynthesis. Molecular-biological methods can be used for this purpose, for example cotransformation using genes that perform the relevant modification. Derivatization can also, however, be carried out chemically, e.g. by chemical conversion of a side chain of an amino acid, or by covalent bonding of a different compound to the protein. Such a compound can also, for example, involve other proteins, which are bound, for example, via bifunctional chemical compounds to proteins according to the present invention. Modifications of this kind influence, for example, the substrate specificity or intensity of binding to the substrate, or bring about a temporary blockage of enzymatic activity if the coupled-on substance is an inhibitor. This is useful, for example, for the period of storage. "Derivatization" is also to be understood as covalent bonding to a macromolecular carrier.

For purposes of the present invention, all enzymes, proteins, fragments, fusion proteins, and derivatives, unless they need to be discussed explicitly as such, are grouped together under the general term "proteins."

The performance of an enzyme is understood as its effectiveness in the particular industrial sector being considered, preferably in the context of a correspondingly directed product. This performance is based on the actual enzymatic activity, but depends furthermore on additional factors relevant to the respective process. These include, for example, stability, substrate binding, interaction with the material carrying the substrate, or interactions with other ingredients, in particular synergies.

The washing performance or cleaning performance of a washing or cleaning product is to be understood, for purposes of the present Application, as the effect exerted by the product in question on the soiled article, for example textiles or hard-surfaced objects. Individual components of such products, for example individual enzymes, are evaluated in terms of their contribution to the washing or cleaning performance of the entire washing or cleaning product, since the enzymatic properties of an enzyme may not readily allow conclusions as to its contribution to the washing performance of a product. Other factors playing a role here are, for example, stability, substrate binding, binding to the items being cleaned, or interactions with other ingredients of the washing or cleaning product, in particular synergies in the context of stain removal.

The amino-acid sequence indicated in SEQ ID NO. 4 has been derived, as described in the Examples hereinbelow, from a nucleic acid that was isolated from a soil sample. The latter's sequence is indicated under SEQ ID NO. 3. The derived protein is referred to herein as "protease HP23."

As presented in Example 3, a homology comparison with previously known proteases was performed for protease HP23 in the "non-redundant gene bank" (Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs," *Nucleic Acids Res.*, 25, pp. 3389-3402). The predominantly putative amino-acid sequences indicated in Table 1 were found in this context. The isolated DNA, on the other hand, coded for a functional protein, as demonstrated by the activity test in the Examples.

A previously described enzyme found to be most similar thereto was a glutamate-specific endopeptidase of the S2B family from *Bacillus licheniformis*, bearing access number P80057 (SEQ ID NO. 8) in the GenBank (National Center for Biotechnology Information, NCBI, National Institutes of Health, Bethesda, Md., USA). The identity at the amino-acid level, determined (like all homology values hereinafter) by way of the computer program Vector NTI® Suite 7.0, obtainable from InforMax, Inc., Bethesda, Md., USA, using the predefined default parameters, is 21.9% (cf. FIG. 1). Of the aforementioned putative proteases, the hypothetical protein from *Oceanobacillus iheyensis* HTE831 having the access number NP_693914 (SEQ ID NO. 11) still possesses the highest homology, namely 30.3% identity. The discovered protease is therefore a novel enzyme whose closest relatives exhibit only a very low degree of homology. With respect to the established *B. lentus* alkaline protease (WO 97/21760 A1), a homology of 14.4% identity exists at the amino-acid level over the entire length of this alkaline protease.

The fact that a V8 protease (or S8 subtilase) was found to be the most similar enzyme must be regarded as an indication that what is involved here is a subtilase but not a subtilisin; the latter is a subgroup of the subtilases that are particularly rich in washing-product proteases. At the same time, because of its relationship to the V8 proteases, HP23 can be assigned to the family of the metalloproteases.

All alkaline proteases that are at least 40% identical to HP23 are encompassed within the present invention.

Preferred among alkaline proteases are subtilases which possess functional regions similar to the alkaline protease of SEQ ID NO. 4.

Also preferred are functional alkaline proteases, i.e. not defective or merely putative enzymes, but rather those that can actually be used for an industrial application on the basis of that enzymatic activity.

Increasingly preferred are all alkaline proteases of this kind that are at least 50%, 55%, 60%, 65%, 70%, 75%, 80%, 82.5%, 85%, 87.5%, 90%, 92.5%, 95%, 96%, 97%, 98%, 99%, and very particularly preferably 100% identical to the indicated amino-acid sequence.

The associated vector described in Examples 2 to 4, which derives from the vector depicted in FIG. 5, received the designation 23-pUC(LP10/03). It was deposited under that name on Nov. 10, 2003 at the German Microorganism and Cell Culture Collection [Deutsche Sammlung von Mikroorganismen and Zellkulturen GmbH, DSMZ], Mascheroder Weg 1b, 38124, Braunschweig, where it bears the deposit number DSM 16017. Viability was confirmed by the DSMZ on Nov. 11, 2003. The protease encoded by this vector is most preferred and is referred to as HP23.

Additionally preferred are those alkaline proteases according to the present invention in which the homology values respectively apply to the region corresponding to amino-acid positions 32 to 327 according to SEQ ID NO. 4.

These are the amino acid residue positions present in the active, mature protein, since it performs the industrially relevant function. As explained in Example 3, at the present time it is not yet possible to state unequivocally which amino acids represent the N terminus of the mature protein. A beginning at one of positions 32 or 35, most probably position 32, according to SEQ ID NO. 4, seems plausible at the moment. If it should be found at a later time that a different amino acid represents the N terminus, such sequences are encompassed by the present invention. The same is true of the C terminus. Position 327 appears plausible at the moment, since nucleotide positions 982-984 according to SEQ ID NO. 3 represent a stop codon. If it should be found at a later time, however, that because of processing, a different amino acid represents the C terminus, such processing variants are also within the scope of the invention. The same applies, in principle, to the case in which internal fragments may possibly be cut out upon maturation of the protein. The amino-acid sequence of the mature protein is particularly preferred in each case.

Further preferred is each of the hitherto described alkaline proteases that is coded by a nucleotide sequence that is at least 50%, and increasingly preferably 55%, 60%, 65%, 70%, 75%, 77.5%, 80%, 82.5%, 85%, 87.5%, 90%, 92.5%, 95%, 96%, 97%, 98%, 99%, and very particularly preferably 100% identical to the nucleotide sequence indicated in SEQ ID NO. 3, in particular for the region that corresponds to nucleotide positions 94 to 984 according to SEQ ID NO:3.

As is evident from what was stated above and in particular from the Examples, the particularly preferred protease has not been detected per se or via a corresponding microorganism, but rather is coded by a nucleic acid discovered in conjunction with the present invention.

As explained in FIG. 3, the enzymes employed for comparison, namely the glutamate-specific endopeptidase from *B. licheniformis* (GenBank DNA access number: D10060 (SEQ ID NO. 7)) and the *B. lentus* alkaline protease (SEQ ID NO. 5), are coded naturally by nucleic acids that possess an identity of 45.9% and 46.2%, respectively, to the regions in SEQ ID NO. 3 in positions 254 to 1311 according to FIG. 2, i.e., to the regions coding for the entire protein.

The protease HP23 that is coded by the nucleic acid depicted in SEQ ID NO. 3, and, corresponding to the statements about the mature protein, very particularly the associated proteases that derive from nucleotide positions 94 to 984 according to SEQ ID NO. 3, are particularly preferred.

A further embodiment of the present invention is an alkaline protease having an amino-acid sequence that is at least 60% identical to the amino-acid sequence indicated in SEQ ID NO. 4 in the region of amino-acid positions 108 to 325.

The reason is that, as explained, a certain doubt still exists as to which regions of the amino-acid sequence indicated in SEQ ID NO. 4 actually represent the mature protein. Leaving aside the considerations presented above with respect to the signal peptide, conclusions in this regard can be drawn from a comparison with the protease from the microorganism *Nesterenkonia* sp. nov. strain (DSM 15380) which, as explained earlier, is disclosed in Application WO 2004/085639 A1. It may be inferred from the alignment of FIG. 2 that this protease is very much smaller than protease HP23, and exhibits homology to amino-acid positions 110 to 325. Its first two amino acids (QN) are associated there with amino acids AS (positions 110 and 111); they could likewise also have been associated with positions 108 and 109 (AN), which (without resorting to a mathematical investigation) appears plausible because N and N, i.e. two identical amino-acid radicals, then correspond to one another.

For this reason, it appears probable that positions 108 to 325 represent a proteolytically active fragment of protease HP23. A fragment of this kind can exhibit advantages with respect to the complete enzyme, not least as regards the success of biotechnological production and the manufacturing costs associated therewith.

Because the protease from *Nesterenkonia* sp. Nov. strain (DSM 15380) (SEQ ID NO. 9), exhibits 52.3% identity over this region, thereby representing the most similar protease, the present invention encompasses partial sequences alkaline proteases that are at least 60% identical. This definite distinction over the existing art takes account of certain fluctuations in terms of homology calculation if certain manual reallocations were to be performed, for convincing reasons, for positions 108 to 111.

In accordance with the above, increasingly preferred are those alkaline proteases that are at least 65%, 70%, 75%, 80%, 85%, 90%, 92.5%, 95%, 97.5%, 98%, 99%, and very particularly 100% identical to the indicated amino-acid sequence region (positions 108 to 325 of SEQ ID NO. 4).

Furthermore preferred are those alkaline proteases that are encoded by a nucleotide sequence that is at least 70% and, increasingly preferably, 75%, 80%, 85%, 90%, 92.5%, 95%, 97.5%, 98%, 99%, and very particularly preferably 100% identical to the nucleotide sequence indicated in SEQ ID NO. 3 in the region of nucleotide positions 322 to 975.

Similar considerations regarding the amino-acid sequences can be applied to the nucleic-acid sequences. The alignment in FIG. 4 shows that the DNA sequence of the protease from *Nesterenkonia* sp. nov. strain (DSM 15380) (SEQ ID NO. 9) possesses 63.9% identity to the region of the nucleotide positions that code for amino-acid positions 108 to 325 of HP23, i.e., the region from 322 to 975. It thus represents the most similar protease-coding DNA sequence over this region.

Notably each of the hitherto described alkaline proteases are obtainable from a natural habitat or derived from a nucleic acid isolatable from a natural habitat.

The DNA isolated using the method described in the Examples was formed by a natural organism, and also codes in vivo for a functional protein. It must therefore be possible, via analogous methods, to find the associated enzymes themselves, in particularly if proteins are actually produced and the DNA does not correspond to a pseudogene. Isolation of the nucleic acids, in contrast, leads directly to a gene that can be introduced into molecular-biological characterizations and produced. In addition, it cannot always be expected that the relevant genes will be expressed under all conditions, so that even genes not translated at the moment are accessible via nucleic acid isolation.

Thus alkaline proteases or the nucleic acids encoded the same obtainable from an organism that is isolatable from a natural habitat are encompassed by the present invention.

This embodiment is particularly advantageous because the associated organism itself can then be cultured. From its cell extracts or culture residues, the proteases according to the present invention can then, advantageously, be isolated and produced.

Preferred are those alkaline proteases isolated from microorganisms, preferably a fungus, a Gram-negative or Gram-positive bacterium, and particularly preferably from the genus *Bacillus*.

Culturing methods are known and established in the existing art in for these organisms. This applies in particular to Bacilli, which play a prominent role in industrial enzyme manufacture.

Also preferred are alkaline proteases or proteins, derived from one of the hitherto described alkaline proteases by fragmentation or deletion mutagenesis, having at least 100 and, increasingly preferably, at least 150, 200, 250, and very particularly preferably at least 300, amino acids already continuously connected in the starting molecule.

For example, it is possible to delete individual amino acids from the termini or loops of the enzyme without losing proteolytic activity. Such mutations are taught, for example, in WO 99/49057 A1. WO 01/07575 A2 teaches that by way of such deletions, the allergenicity of relevant proteases can be decreased, and their overall usability thereby improved. Fragmentation is of benefit for the aspect, discussed later, of insertion or substitution mutagenesis and/or fusion with other enzymes. With regard to the intended use of those enzymes, it is particularly preferred if they possess a proteolytic activity even after fragmentation or deletion mutagenesis.

Also preferred are alkaline proteases according to the present invention that are derived from one of the hitherto described alkaline proteases by insertion mutagenesis, by substitution mutagenesis, and/or by fusion with at least one other protein.

Numerous prior art documents disclose advantageous effects of insertions and substitutions in subtilases, among them are the aforementioned publications WO 99/49057 A1 and WO 01/07575 A2. Included in principle are individual exchanges of amino acids, but multiple continuously: connected amino acids can also be exchanged with each other. Also included are new combinations of larger enzyme portions, e.g. the aforementioned fragments, with other proteases or proteins having a different function. It is possible, for example, on the basis of WO 99/57254 A1, to equip a protein according to the present invention (or parts thereof), via peptide linkers or directly as a fusion protein, with binding domains from other proteins, e.g. the cellulose binding domain, and thereby to make hydrolysis of the substrate more effective. Proteins according to the present invention can likewise, for example, also be linked to amylases or cellulases in order to perform a double function.

Also preferred are the alkaline proteases or proteins having one or more amino-acid exchanges in positions 3, 4, 36, 42, 47, 56, 61, 69, 87, 96, 99, 101, 102, 104, 114, 118, 120, 130, 139, 141, 142, 154, 157, 188, 193, 199, 205, 211, 224, 229, 236, 237, 242, 243, 255, and 268 in the numbering of the alkaline protease *Bacillus lentus* (SEQ ID NO. 6); these positions corresponding to the alignments shown in FIG. 1 or 2.

As explained above and in the description of the Figures, the alignments of both FIGS. 1 and 2 were calculated using the same computer program under the same standard parameters. Because the protease from *Neisterenkonia* sp. involves the introduction of a very much smaller protease, exhibiting a rather moderate degree of relationship, into the alignment of FIG. 2, the two alignments differ in certain positions. Which of the two allocations is "right" or "wrong" cannot be stated, however, so that both must be regarded as fundamentally relevant.

A final decision regarding the association of homologous positions can ultimately be arrived at only by way of comparative experiments in which the two positions associated with one another, on the basis of one of these alignments, in two proteases being compared with one another are point-mutated in the same fashion, and an observation is made as to whether enzymatic activity is modified in both in the same way. For example, if an amino-acid exchange at a specific position of the *B. lentus* alkaline protease (BLAP in both alignments) is associated with an elevation in $K_M$ or in another enzymatic parameter, and if a tendency is observed toward the same shift in the $K_M$ value in an HP23 variant whose individual amino-acid exchange can be correspondingly associated, via one of the alignments in FIGS. 1 or 2, by way of the same introduced amino acid, this is then to be seen as confirmation of this aspect of the invention.

The following amino-acid radicals are located in said positions in the wild-type molecule of the *B. lentus* alkaline protease (SEQ ID NO. 6): S3, V4, S36, N42, A47, T56, G61, T69, E87, A96, R99, A101, I102, S104, N114, H118, A120, S130, S139, T141, 5142, S154, S157, A188, V193, V199, G205, L211, A224, K229, S236, N237, N242, H243, N255, and T268.

Because the *B. lentus* alkaline protease (SEQ ID NO. 6) represents, along with the alkaline protease from *Bacillus licheniformis* (SEQ ID NO. 8), an important reference molecule for describing new proteases and point mutations, and because the new protease described here, and therefore also its sequence, are hitherto unknown, it appears advantageous to refer to this numbering in the allocation of point mutations.

On the other hand, the numbering is generally directed toward the mature protein; and as stated above, the amino acid with which the mature protein begins is not yet certain at the present time. In the count of SEQ ID NO. 4 (HP23), these positions, as may be gathered from FIG. 1, correspond to the following position numbers: 6, 7, 37, 43, 48, 56, 61, 69, 86, 95, 98, 100, 101, 103, 113, 117, 119, 136, 145, 147, 148, 159, 162, 193, 198, 204, 210, 216, 229, 234, 241, 242, 247, 248, 260, and 280.

Application WO 92/21760 A1, for example, discloses single and multiple variants of the subtilisin from *Bacillus lentus* DSM 5483 in the following positions: 3, 4, 36, 42, 47, 56, 69, 87, 96, 101, 102, 104, 114, 118, 120, 130, 139, 141, 142, 157, 188, 193, 199, 205, 224, 229, 236, 237, 242, 243, 255, and 268. Application WO 95/23221 A1 additionally discloses exchanges on this molecule in positions 99, 154, and 211, in particular R99G, R99A, R99S, S154D, S154E, L211D, and L211E. Such variants are also particularly suitable, according to Application WO 95/07770 A1, for use in cosmetics. In addition to other exchanges, Application WO 02/088340 A2 also describes the L211G exchange, and WO 03/038082 A2 the G61A exchange.

Preferred accordingly, are those in which the further amino-acid exchanges are present in one or more of position 3, 4, 61, 188, 193, 199, and 211.

Preferred in turn, in accordance with what was said above, are those involving one or more of the amino-acid exchanges 3T, 4I, 61A, 188P, 193M, 199I, and 211D or 211G, provided the correspondingly homologous positions are not already naturally occupied by one of these preferred amino acids.

As explained in particular in WO 02/088340 A2, the exchanges S3T and V4I result, presumably by way of a stabilizing effect on the molecule, in an improvement in the latter's contribution to the washing performance of a washing or cleaning product. A variant having a double exchange of this kind was also introduced into Examples 7 and 8 of the present Application. The reason is that the exchanges S3T, V4I, A188P, V193M, V199I, and L211D characterize the protease referred to according to WO 95/23221 A1 as F49, which has been employed in Example 7 and 8 of the present Application as a high-performance comparison enzyme that is established in the existing art. In contrast thereto, protease HP23 is still an unmodified wild-type molecule whose activity, in particular whose contribution to washing performance, might obviously be improved by these very same exchanges.

Also preferred is a previously described alkaline protease that is additionally stabilized, in particular by coupling to a polymer.

An increase in stability during storage and/or during use, for example in the washing process, preserves enzymatic activity and thus provides an enhanced effect. Suitable stabilization approaches include any appropriate strategies described in the existing art, for example covalent coupling to a polymer in accordance with U.S. Pat. No. 5,230,891.

Also suitable, as an alternative thereto, are those stabilization approaches that include point mutagenesis of the molecule itself (and that, because of the sequence differences, already fall under the embodiments described above). Such stabilization approaches require no further working steps subsequent to protein recovery. Some point mutations suitable for this are known from the existing art: according to U.S. Pat. No. 6,087,315 and U.S. Pat. No. 6,110,884, for example, proteases can be stabilized by exchanging certain tyrosine radicals for others.

Further possibilities for stabilization are, for example: modifying the binding of metal ions, in particular the calcium binding sites, for example according to the teaching of Applications WO 88/08028 A1 and WO 88/08033 A1. According to the teaching of the former of these documents, one or more of the amino-acid radicals participating in calcium binding can be exchanged for negatively charged amino acids. According to the teaching of Application WO 88/08033, for stabilization via the calcium bond, point mutations can be introduced simultaneously in at least one of the sequences of the two radicals arginine or glycine;

according to U.S. Pat. No. 5,453,372, proteins can be protected from the influence of denaturing agents, such as surfactants, by way of specific mutations on the surface.

Another possibility for stabilization with respect to elevated temperature and the action of surfactants is described in WO 92/21760 A1, WO 02/088340 A2, and WO 03/038082 A2. These references describe stabilization which is achieved by exchanging amino acids located near the N terminus for ones that come into contact (presumably via non-covalent interactions) with the remainder of the molecule, thereby enhancing maintenance of globular structure.

Preferred embodiments are those in which the molecule is stabilized in multiple ways, for example according to WO 89/09819 A1, wherein multiple stabilizing mutations are believed to act additively.

Also preferred is a previously described alkaline protease that is additionally derivatized.

"Derivatives" are understood to be those proteins that are derived from the embodied proteins via an additional modification. Such modifications can influence, for example, the stability, substrate specificity or intensity of binding to the substrate, or enzymatic activity. They can also serve to decrease the allergenicity and/or immunogenicity of the protein, and thereby, for example, enhance its skin compatibility.

Such derivatizations can be accomplished, for example, biologically, e.g. in conjunction with protein biosynthesis by the producing host organism. Couplings of low-molecular-weight compounds, such as lipids or oligosaccharides, are particularly to be emphasized here.

Derivatizations can also, however, be carried out chemically, e.g. by chemical conversion of a side chain or by covalent bonding of a different, e.g. macromolecular, compound to the protein. A chemical modification is described, for example, in Application DE 4013142 A1. The coupling of amines to carboxyl groups of an enzyme in order to modify the isoelectric point is evident, for example, from WO 95/26398 A1. Macromolecules such as proteins can, for example, be bound to proteins according to the present invention, e.g. via bifunctional chemical bonds. Applying the teaching of WO 99/57154 A1, for example, it is possible also to add a specific binding domain via a non-protein linker to a protein according to the present invention. Such derivatives are suitable in particular for use in washing or cleaning products. By analogy with WO 00/01831 A2, protease inhibitors can also be bound via linkers, in particular amino-acid linkers, to the proteins according to the present invention. Couplings with other macromolecular compounds, such as e.g. polyethylene glycol, improve the molecule in terms of further properties such as stability or skin compatibility; this has already been explained.

Derivatives of proteins according to the present invention can also be understood, in the broadest sense, as preparations of these enzymes. Depending on recovery, processing, or preparation, a protein can be brought into association with a variety of other substances, for example deriving from culture of the producing microorganisms. A protein can also, for example in order to enhance its storage stability, have had specific other substances deliberately added to it. All such preparations of a protein fall within the scope of the present invention. This is also irrespective of whether or not it actually displays that enzymatic activity in a specific preparation. The reason is that it may be desirable for the protein to possess little or no activity during storage, and to perform its proteolytic function only at the time of use. This can be controlled, for example, via corresponding accompanying substances. The preparation of proteases together with protease inhibitors is particularly advantageous, and is known from the existing art (WO 00/01826 A2).

Also preferred is a previously described alkaline protease, or a protein of that kind, which has at least one antigenic determinant in common with one of the previously characterized alkaline proteases or proteins, in particular by way of at least one of the epitope regions within which positions 3, 4, 36, 42, 47, 56, 61, 69, 87, 96, 99, 101, 102, 104, 114, 118, 120, 130, 139, 141, 142, 154, 157, 188, 193, 199, 205, 211, 224, 229, 236, 237, 242, 243, 255, and 268 in the numbering of the alkaline protease from Bacillus lentus are located, to be associated by way of one of the alignments in FIG. 1 or 2.

This applies in particular to the above-described variants in these positions, since they are preferred per se, and also can be distinguished, via antibodies that have been formed specifically against these regions, from the proteases that correspond in these positions to the wild-type molecule.

Nucleic acids that are at least 50% identical to the nucleotide sequence provided in SEQ ID NO. 3 also form an aspect of the invention.

The detection of the protease described in the Examples is based on isolation of the pertinent DNA. However, it is appreciated that the nucleic acids can be directly cloned and subjected to genetic-engineering procedures for production of the enzymes described herein.

Increasingly preferred are sequences that are at least 55%, 60%, 65%, 70%, 75%, 77.5%, 80%, 82.5%, 85%, 87.5%, 90%, 92.5%, 95%, 96%, 97%, 98%, 99%, and very particularly preferably 100% identical to the indicated nucleotide sequence.

This is because in accordance with the statements above, and as described in the Examples, only nucleotide sequences having 45.9% and 46.2% identity to SEQ ID NO: 3 have been previously described.

Also preferred are those nucleic acids in which the homology values apply respectively to the region corresponding to nucleotide positions 94 to 984 according to SEQ ID NO. 3.

Thus, the sequences of the invention comprise the region that codes for the mature (i.e. active) protein. The stop codon is also included, since its existence prevents the formation of a larger, undesired fusion protein that might no longer be functional. Care must therefore be taken, in the context of cloning, that a stop codon is also present at this point, if there is no intention to bring about a deliberate protein fusion via the C terminus. If it should later be found that the mature protein is formed by only a portion of this sequence, the range of protection applies correspondingly to that portion.

A further subject of the invention is represented by nucleic acids having a nucleotide sequence that is at least 70% identical to the nucleotide sequence indicated in SEQ ID NO. 3 in the region corresponding to nucleotide positions 322 to 975 according to SEQ ID NO. 3.

As explained above, this region codes for amino-acid positions 108 to 325 in SEQ ID NO. 4, which positions can be associated, via the alignment in FIG. 4 (for the DNA) and FIG. 2 (for the proteins), with the corresponding positions of the protease from Nesterenkonia sp. nov. strain (DSM 15380). This region possess 63.9% identity at the DNA level.

Increasingly preferred accordingly, are those nucleic acids that are 75%, 80%, 85%, 90%, 92.5%, 95%, 97.5%, 98%, 99%, and very particularly 100% identical to the indicated nucleotide sequence region.

Also preferred, and in accordance with what has been discussed above, are those nucleic acids that code for an alkaline protease or a protein of the invention.

Nucleic acids that code only for inactive proteins do not represent are not intended to be encompassed by the invention. Those nucleic acids that code for mature proteins, increasingly particularly those that code for increasingly more active variants, are preferred.

Also preferred are those nucleic acids, one or preferably multiple codons of which have been replaced by synonymous codons.

This aspect refers to the heterologous expression of the relevant proteases. Each organism, in particular each production strain, possesses a certain codon usage. Bottlenecks in protein biosynthesis can occur in this context if the codons located on the transgenic nucleic acid in the host cell are located opposite a comparatively small number of loaded tRNAs. Synonymous codons, on the other hand, code for the same amino acids and can be better translated as a function of the host. This transcription that may optionally be necessary thus depends on the choice of the expression system. A corresponding adaptation may be necessary especially in the case of samples from unknown organisms that may possibly not be culturable.

In accordance with the statements made above, the cells of an organism that naturally contains a nucleic acid according to the present invention are additionally incorporated into the range of protection.

The reason is that by culturing thereof, the desired enzymes can be directly accessible.

Particularly preferred thereamong are those cells that naturally express, and preferably secrete, a protease of the first subject of the invention.

Potentially suitable proteases can thereby be tested immediately, and possibly be recovered in larger quantities by immediate culturing of this organism.

Preferred, in turn are those cells that are microorganisms, preferably fungi, Gram-negative, or Gram-positive bacteria, and thereamong in particularly preferred fashion those of the genus Bacillus.

These organisms are amenable to molecular-biological techniques and production. On the other hand, they are comparatively similar to the established production systems and thus to their codon usage.

A further independent subject of the invention is represented by methods for identifying an alkaline protease as described herein. Such methods comprising isolation of a nucleic acid from a naturally populated habitat.

However, as demonstrated by the present invention, the identification of new proteases does not absolutely require that the relevant proteases and microorganisms also be isolated from nature. It is possible, in particular via shotgun cloning operations or alternatively via PCR primers to known sequence motifs, to discover the relevant nucleic acids directly.

Preferred therefore, are those methods including the use of oligonucleotides, in particular oligonucleotides which are useful for performance of polymerase chain reaction.

A comparable approach based on PCR using suitable primers is evident, for example, from Application WO 03/002711 A2, using the example of α-amylases.

Preferred in turn is a method such that one, preferably two oligonucleotides directed oppositely to one another are used, which are derived from SEQ ID NO. 3 and, particularly preferably, are identical to DNA regions that encompass the regions of positions 1 or 94 or 322 (as the 5' end) to 984 or 981 or 975 (as the 3' end) in accordance with SEQ ID NO. 3.

With reference to SEQ ID NO. 3 and as discussed above, the positions at the 5' end code for the N terminus of the preprotein (position 1), of the mature protein (94), and of the particularly preferred subsequence starting at amino-acid position 108 (322); and at the 3' end for the C terminus of the protein including the stop codon (984), of the mature protein (981), and of the particularly preferred subsequence (975). The length of the PCR primers hybridizing within these regions depends on the melting temperatures and on the PCR conditions that are selected. The M13f and M13r primers (SEQ ID NO. 1 and 2) selected for sequencing, for example, are respectively 16 and 17 nucleotides long. The outer edges of the amplificates are thus defined by positions 1, 97, 322, and 975 or 984. The pertinent primers can also contain, farther outward, additional bases that enable ligation into a corresponding vector.

Among the aforesaid methods, those in which the isolated nucleic acid is cloned are preferred.

Thus, such nucleic acids can be further modified via molecular-biological and biotechnological operations.

Also preferred are those methods in which the isolated nucleic acid is expressed, and is identified as a protease via the protease activity of the expression product.

A further independent subject of the invention is represented by vectors that contain one of the nucleic acid sequences described above.

In order to deal with the nucleic acids relevant to the invention, and thus to prepare proteins according to the present invention, it is appropriate to ligate such nucleic acids into vectors. Such vectors, as well as the associated working methods, are exhaustively described in the existing art. Vectors are commercially available in large numbers and a wide range of variants, both for cloning and for expression. They include, for example, vectors that are derived from bacterial plasmids, from bacteriophages, or from viruses, or predominantly synthetic vectors. They are further differentiated as to the cell types in which they can become established, for example as vectors for Gram-negative or Gram-positive bacteria, for yeasts, or for higher eukaryotes. They constitute suitable starting points, for example, for molecular-biological and biochemical investigations, and for the expression of the relevant gene or protein.

In an embodiment, vectors according to the present invention are cloning vectors.

Cloning vectors are suitable not only for storage, biological amplification, or selection of the gene of interest, but also for further molecular-biological characterization. At the same time, they represent transportable and storable forms of the claimed nucleic acids, and are also starting points for molecular-biological techniques that do not require the use of whole cells, for example PCR or in vitro mutagenesis methods.

Vectors according to the present invention are preferably expression vectors.

Expression vectors are useful for production of proteins in a biological system. Preferred embodiments of this aspect of the invention are expression vectors that carry the genetic elements necessary for expression, for example the natural promoter originally located in front of that gene, or a promoter from a different organism. These elements can be arranged in the form of a so-called expression cassette. Alternatively, individual regulation elements, or all of them, can also be made available by the respective host cell. Particularly preferably, the expression vectors are matched in terms of further properties, e.g. optimum copy number for the selected expression system and in particular to the host cell (see below).

Also included in the invention are cells that, after genetic-engineering modification, contain one of the previously described nucleic-acid sequences.

Such cells contain the genetic information for synthesis of a protein according to the present invention. In contrast to the natural producers of proteases, these genetically engineered cells have been transformed with the nucleic acids described above. Cells so engineered are easily selected, are cultured comparatively easily, and also provide high product yields.

Amplification of the nucleic acids of the invention can be performed in the cells described above. Additionally, such cells can be subjected to mutagenesis followed by transcription and translation of the relevant proteins. This genetic information either can be present extra-chromosomally as a separate genetic element (i.e., in a plasmid in the case of bacteria) or can be integrated into a chromosome. The selection of a suitable system depends on factors which include, how and for how long the gene or organism will be stored, or the type of mutagenesis or selection employed. The existing art describes, for example, mutagenesis and selection methods utilizing bacteriophage and their specific host cells, for the development of washing product enzymes (WO 97/09446 A1).

The aforesaid nucleic-acid sequence is preferably part of one of the above-designated vectors according to the present invention, in particular of a cloning or expression vector.

Such vectors facilitate the practice of the present invention.

Also preferred are those cells that express, and preferably secrete, an alkaline protease as described herein.

Biotechnological production of the proteins of the invention can involve the generation of host cells which express the protease encoding nucleic acids. All organisms are suitable in principle as host cells for protein expression, i.e. prokaryotes, eukaryotes, or cyanophytes. Those host cells that are genetically easy to handle are preferred, for example single-celled fungi or bacteria; this refers, for example, to transformation with the expression vector, stable establishment thereof, and expression regulation. Preferred host cells are moreover distinguished by good microbiological and biotechnological handling characteristics. This refers, for example, to easy culturing, high growth rates, low demand for fermentation media, and good production and secretion rates for foreign proteins. Laboratory strains that are directed toward expression are preferably selected. These are obtainable commercially or via generally accessible strain collections. Each protein according to the present invention can theoretically be obtained in this fashion from a plurality of host organisms. From the large number of different systems available according to the existing art, the optimum expression systems for the individual case must be ascertained experimentally.

Host cells that are themselves protease-negative, and thus do not break down proteins that have formed, are particularly advantageous.

Preferred embodiments include those host cells whose activity can be regulated on the basis of corresponding genetic elements, for example by controlled addition of chemical compounds, by a modification of culture conditions, or as a function of the respective cell density. This controllable expression enables very economical production of the proteins of interest. It can be implemented, for example, by way of a corresponding element on the relevant vector. It is appropriate that the gene, expression vector, and host cell be matched to one another; this relates, for example, to the genetic elements necessary for expression (ribosome binding sites, promoters, terminators) or to codon usage.

Preferred are those expression hosts that secrete the protein, once formed, into the surrounding medium, since as a result it can be processed relatively easily.

Also preferred are host cells that are bacteria.

Bacteria are characterized by short generation times and low demands in terms of culture conditions. As a result cost-effective methods can be established. In addition, a great deal of experience exists with bacteria in terms of fermentation technology. For a specific type of production, Gram-negative or Gram-positive bacteria may be suitable, for a wide variety of reasons (to be ascertained experimentally in the individual case) such as nutrient sources, product formation rate, time requirement, etc.

In a preferred embodiment, the bacterium is Gram-negative, in particular one of the species *Escherichia coli* or *Klebsiella*, in particular strains of *E. coli* K12, *E. coli* B, or *Klebsiella planticola*, and very particularly derivatives of the strains *Escherichia coli* BL21 (DE3), *E. coli* RV308, *E. coli* DH5α, *E. coli* JM109, *E. coli* XL-1, or *Klebsiella planticola* (Rf).

Gram-negative bacteria e.g., *E. coli*, secrete a number of proteins into the periplasmatic space. This can be advantageous for specific applications. Application WO 01/81597 A1 discloses a method comprising the use of secretory Gram-negative bacteria. Such a system is also suitable for the production of proteins according to the present invention. The Gram-negative bacteria cited as preferred are generally easily accessible, i.e. commercially available or available via public strain collections and, in interaction with other components (likewise available in large numbers) such as vectors, are optimizable for specific manufacturing conditions.

In an alternative, no less preferred embodiment, the bacterium is a Gram-positive one, in particular one of the genera *Bacillus*, *Staphylococcus*, or *Corynebacterium*, very particularly of the species *Bacillus lentus*, *B. licheniformis*, *B. amyloliquefaciens*, *B. subtilis*, *B. globigii*, or *B. alcalophilus*, *Staphylococcus carnosus*, or *Corynebacterium glutamicum*.

Gram-positive bacteria possess, with respect to Gram-negative ones, the basic distinction of immediately discharging secreted proteins into the nutrient medium surrounding the cells, from which medium, if desired, the expressed proteins according to the present invention can be directly purified. In addition, they are related or identical to most originating organisms for industrially important subtilisins, and in most cases themselves form comparable subtilisins, so that they utilize similar codons and their protein synthesis apparatus is naturally similar. A further advantage may be the fact that with this method, a mixture of proteins according to the present invention with the subtilisins formed endogenously by the host cells can be obtained. A coexpression approach of this kind is described in Application WO 91/02792. If expression of a plurality of proteases is not desirable, the protease genes naturally present in the host cell can be permanently or temporarily inactivated.

Also preferred are host cells that are eukaryotic cells, preferably of the genus *Saccharomyces*.

Examples include fungi such as actinomycetes and yeasts such as *Saccharomyces* or *Kluyveromyces*. Thermophilic fungal expression systems are described in WO 96/02653 A1. Such systems are suitable in particular for the expression of temperature-resistant variants. Included among the modifications that eukaryotic systems carry out, in particular, in combination with protein synthesis are, for example, the binding of low-molecular-weight compounds such as membrane anchors or oligosaccharides. Such oligosaccharide modifications can be desirable, for example, in order to decrease allergenicity. Coexpression with the enzymes formed naturally by such cells, for example cellulases, can also be advantageous.

Another aspect of the invention entails methods for producing the alkaline proteases described herein.

These include any method for production of an above-described protein according to the present invention, for example chemical synthesis.

Preferred in contrast thereto, however, are all molecular-biological, microbiological, or biotechnological production methods, established in the existing art and already addressed above in individual aspects, that build on the nucleic acids according to the present invention designated above. It is possible to resort for this purpose, in accordance with what has been stated above, e.g. to the nucleic acids indicated in the sequence listing under SEQ ID NO. 3 or to mutants correspondingly derived therefrom, or subsequences thereof.

Thus, such methods involve the use of host cells expressing the vectors comprising the novel protease encoding sequences described herein Such vectors can be advantageously further modified by genetic engineering.

The nucleic acids of the invention may also be expressed in cell-free systems in which protein biosynthesis is completed in vitro. Any of the genetic components discussed above can be combined in methods for the production of the proteases described herein. A plurality of possible combinations of method steps is conceivable in this context for each protein according to the present invention, thus optimal methods depend on the type of protease being produced.

Corresponding to what has been stated above, among the aforesaid methods those in which the nucleotide sequence has been adapted in one codon, preferably multiple codons, to the codon usage of the host strain are preferred.

Another embodiment of the invention includes products containing the above-described alkaline proteases.

All types of products, in particular mixtures, formulations, solutions, etc, whose usability is improved by the addition of an above-described protein, are within the scope of the invention. These can be, for example, depending on the area of application, solid mixtures, e.g., powders having freeze-dried or encapsulated proteins, or gelled or liquid products. Preferred formulations include, without limitation, buffer substances, stabilizers, reaction partners, and/or cofactors of the proteases, and/or other ingredients synergistic with the proteases. Further areas of application are evident from the existing art and are presented, for example, in the manual "Industrial enzymes and their applications" by H. Uhlig, Wiley, N.Y., 1998.

Washing and cleaning products form a particularly preferred aspect of the invention.

Surprisingly, it has been discovered that washing and cleaning products comprising a protease of the invention exhibit greater performance when compared with protease-free products.

All conceivable cleaning products, both concentrates and products to be used undiluted, for use on a commercial scale, in a washing machine or for hand washing or cleaning are included in the invention. These include, for example, washing products for textiles, carpets, or natural fibers, for which the designation washing product is used in accordance with the present invention. These also include, for example, dishwashing products for automatic dishwashers or manual dishwashing, or cleaners for hard surfaces such as metal, glass, porcelain, ceramic, tiles, stone, painted surfaces, plastics, wood, or leather. For these, the designation cleaning product is used in accordance with the present invention.

The present invention encompasses all forms of administration of the washing or cleaning products that are established in the art and/or are appropriate. These include, without limitation, solid, powdered, liquid, gelled, or pasty products, optionally also made up of multiple phases, compressed or uncompressed; e.g., extrudates, granulated materials, tablets, or pouches, both in large containers and in individual portions.

In a preferred embodiment, the washing or cleaning products contain the above-described subtilisin-type alkaline proteases in a quantity from 2 μg to 20 mg, preferably from 5 μg to 17.5 mg, particularly preferably from 20 μg to 15 mg, very particularly preferably from 50 μg to 10 mg, per gram of the product. All integral and non-integral values located respectively between these numbers are included.

The protease activity in such products can be ascertained using the method described in *Tenside*, Volume 7 (1970), pp. 125-132 and is indicated in PU (protease units).

When comparing the performance of two washing-product enzymes, as demonstrated in the Examples of the present Application, a distinction must be made between a protein-equalized and activity-equalized approach. The protein-equalized approach is applied especially in the context of preparations obtained by genetic engineering, which are largely free of secondary activity. Thus, a conclusion can thereby be drawn as to whether the same protein quantities—as a measure of the fermentational production yield—lead to comparable results. If the respective ratios of active substance to total protein (specific activity values) diverge, an activity-equalized comparison is recommended, since in this fashion the respective enzymatic activities can be compared. It is true in general that a low specific activity can be compensated for by adding a larger quantity of protein. The consideration here is ultimately an economic one.

In addition to an alkaline protease according to the present invention of the subtilisin type, a washing or cleaning product can also contain further ingredients such as additional enzymes, enzyme stabilizers, surfactants, e.g. nonionic, anionic, and/or amphoteric surfactants, and/or bleaching agents, and/or builders, as well as, if applicable, further types of ingredients that are discussed below.

The nonionic surfactants used are preferably alkoxylated, advantageously ethoxylated, in particular primary alcohols having preferably 8 to 18 C atoms and an average of 1 to 12 mol ethylene oxide (EO) per mol of alcohol, in which the alcohol radical can be linear or preferably methyl-branched in the 2-position, or can contain mixed linear and methyl-branched radicals, such as those that are usually present in oxo alcohol radicals. Particularly preferred, however, are alcohol ethoxylates having linear radicals made up of alcohols of natural origin having 12 to 18 carbon atoms, e.g. from coconut, palm, tallow, or oleyl alcohol, and an average of 2 to 8 EO per mol of alcohol. The preferred ethyoxylated alcohols include, for example, $C_{12-14}$ alcohols with 3 EO or 4 EO, $C_{9-11}$ alcohol with 7 EO, $C_{13-15}$ alcohols with 3 EO, 5 EO, 7 EO, or 8 EO, $C_{12-18}$ alcohols with 3 EO, 5 EO, or 7 EO, and mixtures thereof, such as mixtures of $C_{12-14}$ alcohol with 3 EO and $C_{12-18}$ alcohol with 5 EO. The degrees of ethoxylation indicated represent statistical averages, which can be an integral or fractional number for a specific product. Preferred alcohol ethoxylates exhibit a narrow distribution of homologs (narrow range ethoxylates, NRE). In addition to these nonionic surfactants, fatty alcohols with more than 12 EO can also be used. Examples of these are tallow fatty alcohol with 14 EO, 25 EO, 30 EO, or 40 EO.

A further class of nonionic surfactants are used either as a sole nonionic surfactant or in combination with other nonionic surfactants. They can be alkoxylated, preferably ethoxylated or ethoxylated and propoxylated fatty acid alkyl esters, preferably having 1 to 4 carbon atoms in the alkyl chain, in particular fatty acid methyl esters.

A further class of nonionic surfactants that can advantageously be used are the alkylpolyglycosides (APG). Usable alkylpolyglycosides satisfy the general formula $RO(G)_z$, in which R denotes a linear or branched, in particular methyl-branched in the 2-position, saturated or unsaturated aliphatic radical having 8 to 22, preferably 12 to 18 C atoms, and G is the symbol standing for a glycose unit having 5 or 6 C atoms, preferably for glucose. The glycolization number z is between 1.0 and 4.0, preferably between 1.0 and 2.0, and in particular between 1.1 and 1.4. Linear alkypolyglucosides, i.e. alkylpolyglycosides in which the polyglycosyl radical is a glucose radical and the alkyl radical is an n-alkyl radical, are used by preference.

Nonionic surfactants of the aminoxide type, for example N-cocalkyl-N,N-dimethylaminoxide and N-tallowalkyl-N, N-dihydroxy-ethylaminoxide, and the fatty acid alkanolamides, can also be suitable. The proportion of these nonionic surfactants is preferably no more than that of the ethoxylated fatty alcohols, in particular no more than half thereof.

Further suitable surfactants are polyhydroxy fatty acid amides of formula (II)

in which RCO denotes an aliphatic acyl radical having 6 to 22 carbon atoms; $R^1$ denotes hydrogen, an alkyl or hydroxyalkyl radical having 1 to 4 carbon atoms; and [Z] denotes a linear or branched polyhydroxyalkyl radical having 3 to 10 carbon atoms and 3 to 10 hydroxyl groups. The polyhydroxy fatty acid amides are known substances that can usually be obtained by reductive amination of a reducing sugar with ammonia, an alkylamine, or an alkanolamine, and subsequent acylation with a fatty acid, a fatty acid alkyl ester, or a fatty acid chloride.

Also belonging to the group of the polyhydroxy fatty acid amides are compounds of formula (III)

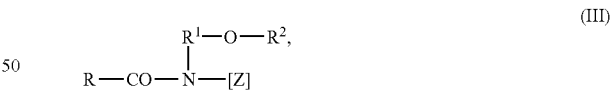

in which R denotes a linear or branched alkyl or alkenyl radical having 7 to 12 carbon atoms; $R^1$ denotes a linear, branched, or cyclic alkyl radical or an aryl radical having 2 to 8 carbon atoms; and $R^2$ denotes a linear, branched, or cyclic alkyl radical or an aryl radical or an oxyalkyl radical having 1 to 8 carbon atoms, $C_{1-4}$ alkyl or phenyl radicals being preferred; and [Z] denotes a linear polyhydroxyalkyl radical whose alkyl chain is substituted with at least two hydroxyl groups, or alkoxylated, preferably ethoxylated or propoxylated, derivatives of that radical.

[Z] is preferably obtained by reductive amination of a reducing sugar, for example glucose, fructose, maltose, lactose, galactose, mannose, or xylose. The N-alkoxy- or N-aryloxy-substituted compounds can be converted into the desired polyhydroxy fatty acid amides, for example, by reaction with fatty acid methyl esters in the presence of an alkoxide as catalyst.

The anionic surfactants can include, for example, those of the sulfonate and sulfate types. Possibilities as surfactants of the sulfonate type are, preferably, $C_{9-13}$ alkylbenzenesulfonates, olefinsulfonates, i.e. mixtures of alkene- and hydroxyalkanesulfonates, and disulfonates, for example such as those obtained from $C_{12-18}$ monoolefins having an end-located or internal double bond, by sulfonation with gaseous sulfur trioxide and subsequent alkaline or acid hydrolysis of the sulfonation products. Also suitable are alkanesulfonates that are obtained from $C_{12-18}$ alkanes, for example by sulfochlorination or sulfoxidation with subsequent hydrolysis and neutralization. The esters of α-sulfo fatty acids (estersulfonates), e.g. the α-sulfonated methyl esters of hydrogenated coconut, palm kernel, or tallow fatty acids, are likewise suitable.

Further suitable anionic surfactants are sulfonated fatty acid glycerol esters. "Fatty acid glycerol esters" are understood to include the mono-, di- and triesters, and mixtures thereof, that are obtained upon production by esterification of a monoglycerol with 1 to 3 mol fatty acid, or upon transesterification of triglycerides with 0.3 to 2 mol glycerol. Preferred sulfonated fatty acid glycerol esters are the sulfonation products of saturated fatty acids having 6 to 22 carbon atoms, for example hexanoic acid, octanoic acid, decanoic acid, myristic acid, lauric acid, palmitic acid, stearic acid, or behenic acid.

Preferred alk(en)yl sulfates are the alkali, and in particular sodium, salts of the sulfuric acid semi-esters of the $C_{12}$-$C_{18}$ fatty alcohols, for example from coconut fatty alcohol, tallow alcohol, lauryl, myristyl, cetyl, or stearyl alcohol, or the $C_{10}$-$C_{20}$ oxo alcohols and those semi-esters of secondary alcohols of those chain lengths. Also preferred are alk(en)yl sulfates of the aforesaid chain length that contain a synthetic straight-chain alkyl radical produced on a petrochemical basis, which possess a breakdown behavior analogous to those appropriate compounds based on fat-chemistry raw materials. For purposes of washing technology, the $C_{12}$-$C_{16}$ alkyl sulfates and $C_{12}$-$C_{15}$ alkyl sulfates, as well as $C_{14}$-$C_{15}$ alkyl sulfates, are preferred. 2,3-alkyl sulfates are also suitable anionic surfactants.

The sulfuric acid monoesters of straight-chain or branched $C_{7-21}$ alcohols ethoxylated with 1 to 6 mol ethylene oxide, such as 2-methyl-branched $C_{9-11}$ alcohols with an average of 3.5 mol ethylene oxide (EO) or $C_{12-18}$ fatty alcohols with 1 to 4 EO, are also suitable. Because of their high foaming characteristics they are used in cleaning products only in relatively small amounts, for example in amounts of up to 5 wt %, usually from 1 to 5 wt %.

Other suitable anionic surfactants are also the salts of alkylsulfosuccinic acid, which are also referred to as sulfosuccinates or as sulfosuccinic acid esters, and which represent the monoesters and/or diesters of sulfosuccinic acid with alcohols, preferably fatty alcohols, and in particular ethyoxylated fatty alcohols. Preferred sulfosuccinates contain $C_{8-18}$ fatty alcohol radicals or mixtures thereof. Particularly preferred are sulfosuccinates containing a fatty alcohol radical that is derived from ethoxylated fatty alcohols which, considered per se, represent nonionic surfactants (see above for description). Sulfosuccinates whose fatty alcohol radicals derive from ethoxylated fatty alcohols with a restricted homolog distribution are, in turn, particularly preferred. It is likewise possible to use alk(en)ylsuccinic acid having preferably 8 to 18 carbon atoms in the alk(en)yl chain, or salts thereof. Further appropriate anionic surfactants are, in particular, soaps. Saturated fatty acid soaps, such as the salts of lauric acid, myristic acid, palmitic acid, stearic acid, hydrogenated erucic acid, and behenic acid, are suitable, as are, in particular, soap mixtures derived from natural fatty acids, e.g. coconut, palm kernel, or tallow fatty acids.

The anionic surfactants, including the soaps, can be present in the form of their sodium, potassium, or ammonium salts, and as soluble salts of organic bases, such as mono-, di-, or triethanolamine. The anionic surfactants are preferably present in the form of their sodium or potassium salts, in particular in the form of the sodium salts.

The surfactants can be contained in the cleaning or washing products in a total quantity of preferably 5 wt % to 50 wt %, in particular 8 wt % to 30 wt %, based on the complete product.

Washing or cleaning products according to the present invention can contain bleaching agents. Among the compounds serving as bleaching agents that yield $H_2O_2$ in water, sodium percarbonate, sodium perborate tetrahydrate, and sodium perborate monohydrate are of particular importance. Other usable bleaching agents are, for example, peroxypyrophosphates, citrate perhydrates, and peracid salts or peracids yielding $H_2O_2$, such as persulfates or persulfuric acid. Also usable is the urea peroxohydrate percarbamide, which can be described by the formula $H_nN—CO—NH_2.H_2O_2$. Especially when the products are used to clean hard surfaces, for example in automatic dishwashing, they can also, if desired, contain bleaching agents from the group of the organic bleaching agents, although use thereof is also possible, in principle, in products for textile washing. Typical organic bleaching agents are the diacyl peroxides, for example dibenzoyl peroxide. Further typical organic bleaching agents are the peroxy acids, the alkylperoxy acids and arylperoxy acids being mentioned in particular as examples. Preferred representatives are peroxybenzoic acid and its ring-substituted derivatives, such as alkylperoxybenzoic acids; but peroxy-α-naphthoic acid and magnesium monoperphthalate, the aliphatic or substituted aliphatic peroxy acids, such as peroxylauric acid, peroxystearic acid, ε-phthalimidoperoxycaproic acid [phthaloimidoperoxy-hexanoic acid (PAP)], o-carboxybenzamidoperoxycaproic acid, N-nonenylamidoperadipic acid, and N-nonenylamidopersuccinates, and aliphatic and araliphatic peroxydicarboxylic acids, such as 1,12-diperoxycarboxylic acid, 1,9-diperoxyazelaic acid, diperoxysebacic acid, diperoxybrassylic acid, the diperoxyphthalic acids, 2-decyldiperoxybutane-1,4-dioic acid, N,N-terephthaloyl-di (6-aminopercaproic)acid, can also be used.

The bleaching-product content of the washing or cleaning products can be 1 to 40 wt % and in particular 10 to 20 wt %, perborate monohydrate or percarbonate advantageously being used.

In order to achieve an improved bleaching effect when washing at temperatures of 60° C. and below, and in particular in the context of laundry pretreatment, the products can also contain bleach activators. Compounds that, under perhydrolysis conditions, yield aliphatic peroxycarboxylic acids having preferably 1 to 10 C atoms, in particular 2 to 4 C atoms, and/or optionally substituted perbenzoic acid, can be used as bleach activators. Substances that carry the O- and/or N-acyl groups having the aforesaid number of C atoms, and/or optionally substituted benzoyl groups, are suitable. Multiply acylated alkylenediamines, in particular tetraacetylethylenediamine (TAED), acylated triazine derivatives, in particular 1,5-diacetyl-2,4-dioxyhexahydro-1,3,5-triazine (DADHT), acylated glycolurils, in particular 1,3,4,6-tetraacetyl glycoluril (TAGU), N-acylimides, in particular N-nonanoyl succinimide (NOSI), acylated phenolsulfonates, in particular n-nonanoyl or isononanoyl oxybenzenesulfonate (n- and iso-NOBS), acylated hydroxycarboxylic acids such as triethyl-O-acetyl citrate (TEOC), carboxylic acid anhydrides, in particular phthalic acid anhydride, isatosic acid anhydride, and/or succinic acid anhydride, carboxylic acid amides such as N-methyl diacetamide, glycolides, acylated polyvalent alcohols, in particular triacetin, ethylene glycol diacetate, isopropenyl acetate, 2,5-diacetoxy-2,5-dihydrofuran, and the enol esters known from German Patent Applications DE 196 16 693 and DE 196 16 767, as well as acylated sorbitol and mannitol or their mixtures (SORMAN) described in European Patent Application EP 0 525 239, acylated sugar derivatives, in particular pentaacetylglucose (PAG), pentaacetylfructose, tetraacetylxylose and octaacetyllactose as well as acylated, optionally N-alkylated glucamine und gluconolactone, triazole and triazole derivatives and/or particulate caprolactams and/or caprolactam derivatives, preferably N-acylated lactams, for example N-benzoylcaprolactam and N-acetylcaprolactam, that are known from International Patent Applications WO 94/27970, WO 94/28102, WO 94/28103, WO 95/00626, WO 95/14759, and WO 95/17498, are suitable. The hydrophilically substituted acyl acetates known from German Application DE 196 16 769 and the acyllactams described in German Application DE 196 16 770 and International Application WO 95/14075 are likewise used in preferred fashion. The combinations of conventional bleach activators known from German Application DE 44 43 177 can also be used. Nitrile derivatives such as cyanopyridines, nitrilquats, e.g. N-alkylammoniumacetonitriles, and/or cyanamide derivatives can likewise be used. Preferred bleach activators are sodium 4-(octanoyl oxy)benzensulfonate, n-nonanoyl or isononanoyl oxybenzenesulfonate (n- and iso-NOBS), undecenoyl oxybenzenesulfonate (UDOBS), sodium dodecanoyl oxybenzenesulfonate (DOBS), decanoyl oxybenzoic acid (DOBA, OBC 10), and/or dodecanoyl oxybenzenesulfonate (OBS 12), as well as N-methylmorpholinum acetonitrile (MMA). Such bleach activators can be present in the usual quantity range from 0.01 to 20 wt %, preferably in quantities from 0.1 to 15 wt %, in particular 1 wt % to 10 wt %, based on the entire composition.

In addition to or instead of the conventional bleach activators, so-called bleach catalysts can also be contained. These substances are bleach-enhancing transition metal salts or transition metal complexes such as, for example, Mn, Fe, Co, Ru, or Mo salt complexes or carbonyl complexes. Mn, Fe, Co, Ru, Mo, Ti, V, and Cu complexes having nitrogen-containing tripod ligands, as well as Co, Fe, Cu, and Ru ammine complexes, are also suitable, those compounds described in DE 19709284 A1 being used in preferred fashion.

Washing or cleaning products according to the present invention generally contain one or more builders, in particular zeolites, silicates, carbonates, organic cobuilders, and— where their use is not inadvisable for environmental reasons—also the phosphates. The latter are detergency builders that are to be used in preferred fashion in particular in cleaning products for automatic dishwashing.

Crystalline sheet-form sodium silicates of the general formula NaMSi$_x$O$_{2x+1}$.H$_2$O, where M denotes sodium or hydrogen, x a number from 1.6 to 4, and y is a number from 0 to 20, and preferred values for x are 2, 3, or 4, may be mentioned here. Such crystalline sheet silicates are described, for example, in European Patent Application EP 164514. Preferred crystalline sheet silicates of the formula indicated above are those in which M denotes sodium and x assumes the value 2 or 3. Both β- and δ-sodium disilicates Na$_2$Si$_2$O$_5$.yH$_2$O are particularly preferred. Compounds of this kind are commercialized, for example, under the designation SKS® (Clariant Co.). SKS-6®, for example, is predominantly a δ-sodium disilicate having the formula Na$_2$Si$_2$O$_5$.yH$_2$O, and SKS-7® is predominantly the β-sodium disilicate. Reaction with acids (e.g. citric acid or carbonic acid) produces, from the δ-sodium disilicate, kanemite (NaHSi$_2$O$_5$.yH$_2$O), available commercially under the designations SKS-9® and SKS-10®, respectively. It can also be advantageous to institute chemical modifications of these sheet silicates. For example, the alkalinity of the sheet silicates can be appropriately influenced. Sheet silicates doped with phosphate or carbonate exhibit modified crystal morphologies as compared with δ-sodium disilicate, dissolve more quickly, and display an elevated calcium binding capability as compared with δ-sodium disilicate. Sheet silicates of the general empirical formula x Na$_2$O.y SiO$_2$.z P$_2$O$_5$, in which the ratio of x to y corresponds to a number from 0.35 to 0.6, the ratio of x to z to a number from 1.75 to 1200, and the ratio of y to z to a number from 4 to 2800, are described, for example, in Patent Application DE 196 01 063. The solubility of the sheet silicates can also be increased by utilizing particularly finely particulate sheet silicates. Compounds of the crystalline sheet silicates with other ingredients can also be used. Compounds with cellulose derivatives, which exhibit advantages in terms of disintegrating action, are used in particular, and especially in washing-product tablets, as well as compounds with polycarboxylates, for example citric acid, or polymeric polycarboxylates, for example copolymers of acrylic acid, may be mentioned in particular.

Also usable are amorphous sodium silicates having a Na$_2$O:SiO$_2$ modulus from 1:2 to 1:3.3, preferably from 1:2 to 1:2.8, and in particular from 1:2 to 1:2.6, which are dissolution-delayed and exhibit secondary washing properties. Dissolution delay as compared with conventional amorphous sodium silicates can be brought about in various ways, for example by surface treatment, compounding, compacting/densification, or overdrying. In the context of this invention, the term "amorphous" is also understood to mean "X-amorphous." In other words, in X-ray diffraction experiments the silicates yield not the sharp X-ray reflections that are typical of crystalline substances, but instead at most one or more maxima in the scattered X radiation, having a width of several degree units of the diffraction angle. Particularly good builder properties can, however, very easily result even if the silicate particles yield blurred or even sharp diffraction maxima in electron diffraction experiments. This may be interpreted to mean that the products exhibit microcrystalline regions 10 to several hundred nm in size, values of up to a maximum of 50 nm, and in particular a maximum of 20 nm, being preferred. Densified/compacted amorphous silicates, compounded amorphous silicates, and overdried X-amorphous silicates are particularly preferred.

A finely crystalline synthetic zeolite containing bound water that is likewise usable, if applicable, is preferably zeolite A and/or zeolite P. Zeolite MAP® (commercial product of the Crosfield Co.) is particularly preferred as a zeolite P. Also suitable, however, are zeolite X as well as mixtures of A, X, and/or P. Also commercially available and preferred for use in the context of the present invention is, for example, a cocrystal of zeolite X and zeolite A (approx. 80 wt % zeolite X) that is marketed by CONDEA Augusta S.p.A. under the trade name VEGOBOND AX® and can be described by the formula nNa$_2$O.(1−n)K$_2$O.Al$_2$O$_3$.(2−2.5)SiO$_2$.(3.5−5.5)H$_2$O Suitable zeolites exhibit an average particle size of less than 10 μm (volume distribution; measurement method:

Coulter Counter), and preferably contain 18 to 22 wt %, in particular 20 to 22 wt %, of bound water.

The use of the generally known phosphates as builder substances is also possible, provided such use is not to be avoided for environmental reasons. Among the plurality of commercially available phosphates, the alkali metal phosphates, with particular preference for pentasodium or pentapotassium triphosphate (sodium or potassium tripolyphosphate), have the greatest significance in the washing and cleaning product industry.

"Alkali metal phosphates" is the summary designation for the alkali-metal (in particular sodium and potassium) salts of the various phosphoric acids, in which context a distinction can be made between metaphosphoric acids $(HPO_3)_n$ and orthophosphoric acid $H_3PO_4$, in addition to higher-molecular-weight representatives. The phosphates offer a combination of advantages: they act as alkali carriers, prevent lime deposits on machine parts and lime encrustations in fabrics, and furthermore contribute to cleaning performance.

Sodium dihydrogenphosphate, $NaH_2PO_4$, exists as the dihydrate (density 1.91 gcm$^{-3}$, melting point 60°) and as the monohydrate (density 2.04 gcm$^{-3}$). Both salts are white powders that are very soluble in water and lose their water of crystallization upon heating, and that transition at 200° C. into the weakly acid diphosphate (disodium hydrogendiphosphate, $Na_2H_2P_2O_7$), and at higher temperature into sodium trimetaphosphate $(Na_3P_3O_9)$ and Maddrell salt (see below). $NaH_2PO_4$ reacts in acid fashion; it is created when phosphoric acid is adjusted with sodium hydroxide to a pH of 4.5 and the mash is spray-dried. Potassium dihydrogenphosphate (primary or unibasic potassium phosphate, potassium diphosphate, KDP), $KH_2PO_4$, is a white salt of density 2.33 gcm$^{-3}$, has a melting point of 253° [decomposing to form potassium polyphosphate $(KPO_3)_x$], and is readily soluble in water.

Disodium hydrogenphosphate (secondary sodium phosphate), $Na_2HPO_4$, is a colorless, water-soluble crystalline salt. It exists anyhdrously and with 2 mol (density 2.066 gcm$^{-3}$, water lost at 95°), 7 mol (density 1.68 gcm$^{-3}$, melting point 48° with loss of 5 $H_2O$), and 12 mol of water (density 1.52 gcm$^{-3}$, melting point 35° with loss of 5 $H_2O$); it becomes anhydrous at 100° and when more strongly heated transitions into the diphosphate $Na_4P_2O_7$. Disodium hydrogenphosphate is produced by the neutralization of phosphoric acid with a soda solution using phenolphthalein as indicator. Dipotassium hydrogenphosphate (secondary or dibasic potassium phosphate), $K_2HPO_4$, is an amorphous white salt that is easily soluble in water.

Trisodium phosphate (tertiary sodium phosphate), $Na_3PO_4$, exists as colorless crystals that as the dodecahydrate have a density of 1.62 gcm$^{-3}$ and a melting point of 73-76° C. (decomposition), as the decahydrate (corresponding to 19-20% $P_2O_5$) a melting point of 100° C., and in anhydrous form (corresponding to 39-40% $P_2O_5$) a density of 2.536 gcm$^{-3}$. Trisodium phosphate is easily soluble in water with an alkaline reaction, and is produced by evaporating a solution of exactly 1 mol disodium phosphate and 1 mol NaOH. Tripotassium phosphate (tertiary or tribasic potassium phosphate), $K_3PO_4$, is a white, deliquescent, granular powder with a density of 2.56 gcm$^{-3}$, has a melting point of 1340° C., and is soluble in water with an alkaline reaction. It is produced, for example, upon heating of basic slag with carbon and potassium sulfate. Despite the higher price, the increased solubility and therefore highly active potassium phosphates are greatly preferred over corresponding sodium compounds in the cleaning product industry.

Tetrasodium diphosphate (sodium pyrophosphate), $Na_4P_2O_7$, exists in anhydrous form (density 2.534 gcm$^{-3}$, melting point 988°, also indicated as 880°) and as the decahydrate (density 1.815-1.836 gcm$^{-3}$, melting point 94° with loss of water). Both substances are colorless crystals that are soluble in water with an alkaline reaction. $Na_4P_2O_7$ is created when disodium phosphate is heated to >200°, or by reacting phosphoric acid with soda in the stoichiometric ratio and dewatering the solution by spraying. The decahydrate complexes heavy-metal salts and hardness constituents, and therefore decreases water hardness. Potassium diphosphate (potassium pyrophosphate), $K_4P_2O_7$, exists in the form of the trihydrate and represents a colorless, hygroscopic powder with a density of 2.33 gcm$^{-3}$ that is soluble in water, the pH of a 1% solution being 10.4 at 25°.

Condensation of $NaH_2PO_4$ or $KH_2PO_4$ yields higher-molecular-weight sodium and potassium phosphates, within which a distinction can be made between cyclic representatives (the sodium and potassium metaphosphates) and chain types (the sodium and potassium polyphosphates). For the latter in particular, a number of designations are in use: fused or thermal phosphates, Graham salt, Kurrol's salt, and Maddrell salt. All the higher sodium and potassium phosphates are together referred to as "condensed" phosphates.

The industrially important pentasodium triphosphate $Na_5P_3O_{10}$ (sodium tripolyphosphate) is a white, water-soluble, non-hygroscopic salt, crystallizing anhydrously or with 6 $H_2O$, of the general formula NaO—[P(O)(ONa)—O]$_n$—Na, where n=3. Approximately 17 g of the salt containing no water of crystallization dissolves in 100 g of water at room temperature, approx. 20 g at 60° C., and approx. 32 g at 100°; after the solution is heated to 100° for two hours, approx. 8% orthophosphate and 15% disphosphate are produced by hydrolysis. In the production of pentasodium triphosphate, phosphoric acid is reacted with a soda solution or sodium hydroxide in the stoichiometric ratio, and the solution is dewatered by spraying. Like Graham salt and sodium diphosphate, pentasodium triphosphate dissolves many insoluble metal compounds (including lime soaps, etc.). Pentapotassium triphosphate $K_5P_3O_{10}$ (potassium tripolyphosphate) is marketed, for example, in the form of a 50-wt % solution (>23% $P_2O_5$, 25% $K_2O$). The potassium polyphosphates are widely used in the washing and cleaning product industry. Sodium potassium tripolyphosphates also exist, and are likewise usable in the context of the present invention. They are produced, for example, when sodium trimetaphosphate is hydrolyzed with KOH:

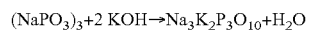

$(NaPO_3)_3 + 2\ KOH \rightarrow Na_3K_2P_3O_{10} + H_2O$

These are usable according to the present invention in just the same way as sodium tripolyphosphate, potassium tripolyphosphate, or mixtures of the two; mixtures of sodium tripolyphosphate and sodium potassium tripolyphosphate, or mixtures of potassium tripolyphosphate and sodium potassium tripolyphosphate, or mixtures of sodium tripolyphosphate and potassium tripolyphosphate and sodium potassium tripolyphosphate, are also usable according to the present invention.

Polycarboxylates or polycarboxylic acids, in particular, polymeric polycarboxylates, polyaspartic acid, polyacetals, dextrins (optionally oxidized), further organic cobuilders (see below), and phosphonates can be used, as organic cobuilders in the washing and cleaning products according to the present invention. These substance classes are described below.

Usable organic builder substances are, for example, the polycarboxylic acids usable in the form of their sodium salts. "Polycarboxylic acids" being understood as those carboxylic acids that carry more than one acid function. These are, for example, citric acid, adipic acid, succinic acid, glutaric acid, malic acid, tartaric acid, maleic acid, fumaric acid, sugar acids, aminocarboxylic acids, nitrilotriacetic acid (NTA), provided such use is not to be avoided for environmental reasons, as well as mixtures thereof. Preferred salts are the salts of the polycarboxylic acids such as citric acid, adipic acid, succinic acid, glutaric acid, tartaric acid, sugar acids, and mixtures thereof.

The acids per se can also be used. The acids typically also possess, in addition to their builder effect, the property of an acidifying component, and thus serve also to adjust the pH to a lower and milder level in cases where the pH resulting from mixture of the other components is not desired. To be mentioned in particular in this context are system-compatible and environmentally compatible acids such as citric acid, acetic acid, tartaric acid, malic acid, lactic acid, glycolic acid, succinic acid, glutaric acid, adipic acid, gluconic acid, and any mixtures thereof. Mineral acids, however, in particular sulfuric acid, or bases, in particular ammonium or alkaline hydroxides, can also serve as pH regulators. Such regulators are contained in the products according to the present invention in quantities preferably not exceeding 20 wt %, in particular from 1.2 wt % to 17 wt %.

Polymeric polycarboxylates are additionally suitable as builders; these are, for example, the alkali metal salts of polyacrylic acid or polymethacrylic acid, for example those having a relative molecular weight of 500 to 70,000 g/mol.

The molar weights indicated for polymeric polycarboxylates are, for purposes of this document, weight-averaged molar weights $M_w$ of the respective acid form, which were determined in principle by means of gel permeation chromatography (GPC), a UV detector having been used. The measurement was performed against an external polyacrylic acid standard that, because it is structurally related to the polymers being investigated, yielded realistic molecular weight values. These indications deviate considerably from the molecular weight indications in which polystyrenesulfonic acids are used as the standard. The molar weights measured against polystyrenesulfonic acids are usually much higher than the molar weights indicated in this document.

Suitable polymers are, in particular, polyacrylates that preferably have a molecular weight from 2000 to 20,000 g/mol. Because of their superior solubility, of this group the short-chain polyacrylates that have molar weights from 2000 to 10,000 g/mi, and particularly preferably from 3000 to 5000 g/mol, may in turn be preferred.

Copolymeric polycarboxylates, in particular those of acrylic acid with methacrylic acid and of acrylic acid or methacrylic acid with maleic acid, are also suitable. Copolymers of acrylic acid with maleic acid that contain 50 to 90 wt % acrylic acid and 50 to 10 wt % maleic acid have proven particularly suitable. Their relative molecular weight, based on free acids, is generally 2000 to 70,000 g/mol, preferably 20,000 to 50,000 g/mol, and in particular 30,000 to 40,000 g/mol. The (co)polymeric polycarboxylates can be used either as powders or as an aqueous solution. The (co)polymeric polycarboxylate content of the products can be from 0.5 to 20 wt %, in particular 1 to 10 wt %.

To improve water solubility, the polymers can also contain allylsulfonic acids, for example allyloxybenzenesulfonic acid and methallylsulfonic acid, as monomers.

Also particularly preferred are biodegradable polymers made up of more than two different monomer units, for example those that contain salts of acrylic acid and of maleic acid, as well as vinyl alcohol or vinyl alcohol derivatives, as monomers, or that contain salts of acrylic acid and of 2-alkylallylsulfonic acid, as well as sugar derivatives, as monomers.

Further preferred copolymers are those that comprise preferably acrolein and acrylic acid/acrylic acid salts, or acrolein and vinyl acetate, as monomers.

Likewise to be mentioned as additional preferred builder substances are polymeric aminodicarboxylic acids, their salts, or their precursor substances. Polyaspartic acid and its salts and derivatives are particularly preferred.

Other suitable builder substances are polyacetals, which can be obtained by reacting dialdehydes with polyol carboxylic acids that have 5 to 7 carbon atoms and at least 3 hydroxyl groups. Preferred polyacetals are obtained from dialdehydes such as glyoxal, glutaraldehyde, terephthalaldehyde, and mixtures thereof, and from polyol carboxylic acids such as gluconic acid and/or glucoheptonic acid.

Other suitable organic builder substances are dextrins, for example oligomers or polymers of carbohydrates, which can be obtained by partial hydrolysis of starches. The hydrolysis can be performed in accordance with usual, e.g. acid- or enzyme-catalyzed, methods. Preferably these are hydrolysis products having average molar weights in the range from 400 to 500,000 g/mol. A polysaccharide having a dextrose equivalent (DE) in the range from 0.5 to 40, in particular from 2 to 30, is preferred, DE being a common measure of the reducing effect of a polysaccharide as compared with dextrose, which possesses a DE of 100. Also usable are maltodextrins having a DE between 3 and 20, and dry glucose syrups having a DE between 20 and 37, as well as so-called yellow dextrins and white dextrins having higher molar weights in the range from 2000 to 30,000 g/mol.

The oxidized derivatives of such dextrins are their reaction products with oxidizing agents that are capable of oxidizing at least one alcohol function of the saccharide ring to the carboxylic acid function. Particularly preferred organic builders for products according to the present invention are oxidized starches, or their derivatives, from Applications EP 472042, WO 97/25399, and EP 755944.

Oxydisuccinates and other derivatives of disuccinates, preferably ethylenediamine disuccinate, are also additional suitable cobuilders. Ethylenediamine N,N'-disuccinate (EDDS) is used here, preferably in the form of its sodium or magnesium salts. Also preferred in this context are glycerol disuccinates and glycerol trisuccinates. Suitable utilization amounts in zeolite-, carbonate-, and/or silicate-containing formulations are 3 to 15 wt %.

Other usable organic cobuilders are, for example, acetylated hydroxycarboxylic acids and their salts, which can optionally also be present in lactone form and which contain at least 4 carbon atoms and at least one hydroxy group, as well as a maximum of two acid groups.

A further substance class having cobuilder properties is represented by the phosphonates. These are, in particular, hydroxyalkane- and aminoalkanephosphonates. Among the hydroxyalkanephosphonates, 1-hydroxyethane-1,1-diphosphonate (HEDP) is particularly important as a cobuilder. It is preferably used as a sodium salt; the disodium salt reacts neutrally, and the tetrasodium salt in alkaline fashion (pH 9). Suitable aminoalkanephosphonates are preferably ethylenediaminetetra-methylenephosphonate (EDTMP), diethylenetriaminepentamethylene-phosphonate (DTPMP), and their higher homologs. They are preferably used in the form of the neutrally reacting sodium salts, e.g. as the hexasodium salt of EDTMP or as the hepta- and octasodium salt of DTPMP. Of the class of the phosphonates, HEDP is preferably used as a builder. The amino-alkanephosphonates furthermore possess a pronounced heavy-metal binding capability. It may accordingly be preferred, especially when the products also contain bleaches, to use aminoalkanephosphonates, in particular DTPMP, or mixtures of the aforesaid phosphonates.

All compounds that are capable of forming complexes with alkaline-earth ions can also be used as cobuilders.

Builder substances can be contained in the washing or cleaning products according to the present invention, if applicable, in quantities of up to 90 wt %. They are preferably contained in quantities of up to 75 wt %. Washing products according to the present invention have builder contents of, in particular, 5 wt % to 50 wt %. In products according to the present invention for cleaning hard surfaces, in particular for automatic cleaning of dishes, the content of builder substances is, in particular, 5 wt % to 88 wt %, no water-insoluble builder substances preferably being used in such products. In a preferred embodiment of products according to the present invention for, in particular, automatic cleaning of dishes, 20 wt % to 40 wt % of water-soluble builders, in particular alkaline citrate, 5 wt % to 15 wt % alkaline carbonate, and 20 wt % to 40 wt % alkaline disilicate, are contained.

Solvents that can be used in the liquid to gelled compositions of washing and cleaning products derive preferably from the group of the univalent or polyvalent alcohols, alkanolamines, or glycol ethers, provided they are miscible with water in the indicated concentration range. The solvents are preferably selected from ethanol, n- or i-propanol, butanols, ethylene glycol methyl ether, ethylene glycol ethyl ether, ethylene glycol propyl ether, ethylene glycol mono-n-butyl ether, diethylene glycol methyl ether, diethylene glycol ethyl ether, propylene glycol methyl, ethyl, or propyl ether, dipropylene glycol monomethyl or ethyl ether, diisopropylene glycol monomethyl or ethyl ether, methoxy-, ethoxy-, or butoxytriglycol, 1-butoxyethoxy-2-propanol, 3-methyl-3-methoxybutanol, propylene glycol-t-butyl ether, and mixtures of these solvents. Solvents can be used in the liquid to gelled washing and cleaning products according to the present invention in quantities between 0.1 and 20 wt %, but preferably less than 15 wt %, and in particular less than 10 wt %.

In order to adjust viscosity, one or more thickeners or thickening systems can be added to the composition according to the present invention. These high-molecular-weight substances, also called swelling agents, usually soak up the liquids and thereby swell up, ultimately transitioning into viscous true or colloidal solutions.

Suitable thickeners are inorganic or polymeric organic compounds. The inorganic thickeners include, for example, polysilicic acids, clay minerals such as montmorillonites, zeolites, silicic acids, and bentonites. The organic thickeners derive from the group of the natural polymers, the modified natural polymers, and the entirely synthetic polymers. Such polymers deriving from nature are, for example, agar-agar, carrageenan, tragacanth, gum arabic, alginates, pectins, polyoses, guar flour, locust bean flour, starches, dextrins, gelatins, and casein. Modified natural substances that are used as thickeners derive principally from the group of the modified starches and celluloses. Examples that may be mentioned here are carboxymethyl cellulose and other cellulose ethers, hydroxyethyl and propyl cellulose, and grain meal ethers. Entirely synthetic thickeners are polymers such as polyacrylate and polymethacrylate compounds, vinyl polymers, polycarboxylic acids, polyethers, polyimines, polyamides, and polyurethanes.

The thickeners can be contained in a quantity of up to 5 wt %, preferably 0.05 to 2 wt %, and particularly preferably 0.1 to 1.5 wt %, based on the final composition.

The washing and cleaning product according to the present invention can contain, if applicable, as further usual ingredients, sequestration agents, electrolytes, and further adjuvants such as optical brighteners, graying inhibitors, silver corrosion inhibitors, color transfer inhibitors, foam inhibitors, abrasives, dyes and/or fragrances, as well as microbial active substances, UV absorbers, and/or enzyme stabilizers.

Textile washing products according to the present invention can contain, as optical brighteners, derivatives of diaminostilbenedisulfonic acid or of its alkali-metal salts. Suitable, for example, are salts of 4,4'-bis(2-anilino-4-morpholino-1,3,5-triazinyl-6-amino)stilbene-2,2'-disulfonic acid, or similarly constructed compounds that carry, instead of the morpholino group, a diethanolamino group, a methylamino group, an anilino group, or a 2-methoxyethylamino group. Brighteners of the substituted diphenyistyryl type can furthermore be present, for example the alkali salts of 4,4'-bis (2-sulfostyryl)diphenyl, 4,4'-bis(4-chloro-3-sulfostyryl) diphenyl, or 4-(4-chloro-styryl)-4'-(2-sulfostyryl)diphenyl. Mixtures of the aforesaid optical brighteners can also be used.

The purpose of graying inhibitors is to keep dirt released from the fibers suspended in the bath. Water-soluble colloids, usually organic in nature, are suitable for this, for example starch, size, gelatins, salts of ethercarboxylic acids or ethersulfonic acids of starch or cellulose, or salts of acid sulfuric-acid esters of cellulose or starch. Water-soluble polyamides containing acid groups are also suitable for this purpose. Starch derivatives other than those mentioned above can also be used, for example aldehyde starches, etc. It is preferred to use cellulose ethers such as carboxymethyl cellulose (Na salt), methyl cellulose, hydroxyalkyl cellulose, and mixed ethers such as methyl-hydroxyethyl cellulose, methylhydroxypropyl cellulose, methylcarboxylmethyl cellulose, and mixtures thereof, for example in quantities from 0.1 to 5 wt % based on the product.

In order to effect silver corrosion protection, silver corrosion inhibitors can be used in cleaning products according to the present invention for dishes. Such inhibitors are known from the existing art, for example benzotriazole, iron(III) chloride, or $CoSO_4$. As is known e.g. from European Patent EP 0 736 084 B1, manganese, titanium, zirconium, hafnium, vanadium, cobalt, or cerium salts or complexes, in which said metals are present in one of the oxidation states II, III, IV, V, or V, are silver corrosion inhibitors that are particularly suitable for use together with enzymes. Examples of such compounds are $MnSO_4$, $V_2O_5$, $V_2O_4$, $VO_2$, $TiOSO_4$, $K_2TiF_6$, $K_2ZrF_6$, $Co(NO_3)_2$, $Co(NO_3)_3$, and mixtures thereof.

"Soil release" active substances, or "soil repellents," are in most cases polymers that, when used in a washing product, impart dirt-repelling properties to the laundry fibers and/or assist the dirt dissolution capability of the other washing-product constituents. A comparable effect can also be observed when they are used in cleaning products for hard surfaces.

Soil release ingredients that are particularly effective and have been known or some time are copolyesters having dicarboxylic acid, alkylene glycol, and polyalkylene glycol units. Examples thereof are copolymers or mixed polymers made up of polyethylene terephthalate and polyoxyethylene glycol (DT 16 17 141 and DT 22 00 911, respectively). German Unexamined Application DT 22 53 063 recites acid products that contain, inter alia, a copolymer of a dibasic carboxylic acid and an alkylene or cycloalkylene polyglycol. Polymers of ethylene terephthalate and polyethylene oxide terephthalate, and their use in washing products, are described in the German documents DE 28 57 292 and DE 33 24 258, and in European Patent EP 0 253 567. European Patent EP 066 944 relates to products containing a copolyester of ethylene glycol, polyethylene glycol, aromatic dicarboxylic acid, and sulfonated aromatic dicarboxylic acid in specific molar ratios. Polyesters end-capped with methyl or ethyl groups and having ethylene and/or propylene terephthalate and polyethylene oxide terephthalate units, and washing products that contain such soil release polymers, are known from European Patent EP 0 185 427. European Patent EP 0 241 984 relates to a polyester that contains not only oxyethylene groups and terephthalic acid units, but also substituted ethylene units as well as glycerol units. European Patent EP 0 241 985 discloses polyesters that contain not only oxyethylene groups and terephthalic acid units, but also 1,2-propylene, 1,2-butylene, and/or 3-methoxy-1,2-propylene groups as well as glycerol units, and are end-capped with $C_1$ to $C_4$ alkyl groups. European Patent Application EP 0 272 033 discloses polyesters that are end-capped at least in part with $C_{1-4}$ alkyl or acyl radicals, and that have polypropylene terephthalate and polyoxyethylene terephthalate units. European Patent EP 0 274 907 describes terephthalate-containing soil-release polyesters end-capped with sulfoethyl groups. According to European Patent Application EP 0 357 280, soil-release polyesters having terephthalate, alkylene glycol, and poly-$C_{2-4}$ glycol units are produced by sulfonation of unsaturated end groups. International Patent Application WO 95/32232 relates to acid, aromatic, dirt-release-promoting polyesters. International Patent Application WO 97/31085 discloses non-polymeric soil-repellent ingredients for materials made from cotton, having multiple functional units: a first unit, which can e.g. be cationic, is capable of adsorption onto the cotton surface by electrostatic interaction, and a second unit, which is configured to be hydrophobic, is responsible for retention of the active substance at the water/cotton interface.

Color transfer inhibitors suitable for use in textile washing products according to the present invention include, in particular, polyvinylpyrrolidones, polyvinylimidazoles, polymeric N-oxides such as poly(vinylpyridine-N-oxide), and copolymers of vinylpyrrolidone with vinylimidazole.

For use in automatic cleaning methods, it can be advantageous to add foam inhibitors to the relevant products. Suitable as foam inhibitors are, for example, soaps of natural or synthetic origin that have a high concentration of $C_{18}$-$C_{24}$ fatty acids. Suitable non-surfactant-like foam inhibitors are, for example, organopolysiloxanes and mixtures thereof with microfine, optionally silanated silicic acid, as well as paraffins, waxes, microcrystalline waxes, and mixtures thereof with silanated silicic acid or bistearylethylenediamide. It is also advantageous to use mixtures of different foam inhibitors, for example those made of silicones, paraffins, or waxes. The foam inhibitors, in particular silicone- and/or paraffin-containing foam inhibitors, are preferably bound to a granular, water-soluble or -dispersible carrier substance. Mixtures of paraffins and bistearylethylendiamides are particularly preferred in this context.

A cleaning product according to the present invention for hard surfaces can moreover contain abrasively acting constituents, in particular from the group encompassing quartz flours, wood flours, plastic flours, chalks, and glass microspheres, as well as mixtures thereof. Abrasives are contained in the cleaning products according to the present invention preferably at no more than 20 wt %, in particular from 5 wt % to 15 wt %.

Dyes and fragrances are added to washing and cleaning products in order to improve the aesthetic impression of the products and make available to the consumer not only washing and cleaning performance but also a visually and sensorially "typical and unmistakable" product. Individual aroma compounds, e.g. the synthetic products of the ester, ether, aldehyde, ketone, alcohol, and hydrocarbon types, can be used as perfume oils or fragrances. Aroma compounds of the ester type are, for example, benzyl acetate, phenoxyethyl isobutyrate, p-tert.butylcyclohexyl acetate, linalyl acetate, dimethylbenzylcarbinyl acetate, phenylethyl acetate, linalyl benzoate, benzyl formate, ethylmethylphenyl glycinate, allylcyclohexyl propionate, styrallyl propionate, and benzyl salicylate. The ethers include, for example, benzylethyl ether; the aldehydes, for example, the linear alkanals having 8-18 carbon atoms, citral, citronellal, citronellyloxyacetaldehyde, cyclamenaldehyde, hydroxycitronellal, lilial und bourgeonal; the ketones, for example, the ionones, α-isomethylionone und methylcedryl ketone; the alcohols, anethol, citronellol, eugenol, geraniol, linalool, phenylethyl alcohol and terpineol; and the hydrocarbons include principally the terpenes such as limonene and pinene. Preferably, however, mixtures of different aromas that together produce an appealing fragrance note are used. Such perfume oils can also contain natural aroma mixtures such as those accessible from plant sources, for example pine, citrus, jasmine, patchouli, rose, or ylang-ylang oil. Also suitable are muscatel, salvia oil, chamomile oil, clove oil, lemon balm oil, mint oil, cinnamon leaf oil, linden blossom oil, juniper berry oil, vetiver oil, olibanum oil, galbanum oil, and labdanum oil, as well as orange blossom oil, neroli oil, orange peel oil, and sandalwood oil. The dye content of washing and cleaning products is usually less than 0.01 wt %, while fragrances can constitute up to 2 wt % of the entire formulation.

The fragrances can be incorporated directly into the washing or cleaning products, but it can also be advantageous to apply the fragrances onto carriers that enhance adhesion of the perfume to the material being cleaned, and ensure a slower fragrance release for longer-lasting fragrance, in particular of treated textiles. Cyclodextrins, for example, have proven successful as carrier materials of this kind; the cyclodextrin-perfume complexes can additionally be coated with further adjuvants. A further preferred carrier for fragrances is the above-described zeolite X, which can also receive fragrances instead of, or in a mixture with, surfactants. Washing and cleaning products that contain the above-described zeolite X and fragrances that preferably are absorbed at least in part onto the zeolite are therefore preferred.

Preferred dyes, the selection of which will present absolutely no difficulty to one skilled in the art, possess excellent shelf stability and insensitivity to the other ingredients of the products and to light, and no pronounced substantivity with respect to textile fibers, in order not to color them.

To counteract microorganisms, washing or cleaning products can contain antimicrobial active substances. A distinction is made here, in terms of the antimicrobial spectrum and mechanism of action, between bacteriostatics and bactericides, fungistatics and fungicides, etc. Important substances from these groups are, for example, benzalkonium chloride, alkylarylsulfonates, halogen phenols, and phenol mercuric acetate. The terms "antimicrobial action" and "antimicrobial active substance" have, in the context of the teaching of the present invention, the meaning usual among those skilled in the art, as reproduced e.g. by K. H. Wallhäußer in "Praxis der Sterilisation, Desinfektion—Konservierung: Keimidentifizierung—Betriebshygiene" [Practical sterilization, disinfection, conservation, germ identification, and industrial hygiene] (5th ed.—Stuttgart; New York: Thieme, 1995), in which context all substances described therein having an antimicrobial action can be used. Suitable antimicrobial active substances are preferably selected from the groups of the alcohols, amines, aldehydes, antimicrobial acids and their salts, carboxylic acid esters, acid amides, phenols, phenol derivatives, diphenyls, diphenylalkanes, urea derivatives, oxygen and nitrogen acetals and formals, benzamidines, isothiazolines, phthalimide derivatives, pyridine derivatives, antimicrobial surface-active compounds, guanidines, antimicrobial amphoteric compounds, quinolines, 1,2-dibromo-2,4-dicyanobutane, iodo-2-propylbutyl carbamate, iodine, iodophores, peroxo compounds, halogen compounds, and any mixtures of the above.

The antimicrobial active substance can be selected from ethanol, n-propanol, i-propanol, 1,3-butanediol, phenoxyethanol, 1,2-propylene glycol, glycerol, undecylenic acid, benzoic acid, salicylic acid, dihydracetic acid, o-phenylphenol, N-methylmorpholineacetonitrile (MMA), 2-benzyl-4-chlorophenol, 2,2'-methylene-bis-(6-bromo-4-chlorophenol), 4,4'-dichloro-2'-hydroxydiphenyl ether (Diclosan), 2,4,4'-trichloro-2'-hydroxydiphenyl ether (Triclosan), chlorhexidine, N-(4-chlorophenyl)-N-(3,4-dichlorophenyl) urea, N,N'-(1,10-decanediyldi-1-pyridinyl-4-ylidene)-bis-(1-octanamine)dihydrochloride, N,N'-bis-(4-chlorophenyl)-3,12-diimino-2,4,11,13-tetraazatetradecanediimideamide, glucoprotamines, antimicrobial surface-active quaternary compounds, guanidines including the bi- and polyguanidines such as, for example, 1,6-bis-(2-ethylhexylbiguanidohexane) dihydrochloride, 1,6-di-($N_1,N_1$'-phenyldiguanido-$N_5,N_5$') hexane tetrahydrochloride, 1,6-di-($N_1,N_1$'-phenyl-$N_1,N_1$'-methyldiguanido-$N_5,N_5$')hexane dihydrochloride, 1,6-di-($N_1,N_1$'-o-chlorophenyldiguanido-$N_5,N_5$')hexane dihydrochloride, 1,6-Di-($N_1,N_1$'-2,6-dichlorophenyldiguanido-$N_5,N_5$')hexane dihydrochloride, 1,6-Di-[$N_1,N_1$'-beta-(p-methoxyphenyl)diguanido-$N_5,N_5$']hexane dihydrochloride, 1,6-Di-($N_1,N_1$'-alpha-methyl-β-phenyldiguanido-$N_5,N_5$')hexane dihydrochloride, 1,6-bi-($N_1,N_1$'-p-nitrophenyldiguanido-$N_5,N_5$')hexane dihydrochloride, ω:ω-di-($N_1,N_1$'-phenyldiguanido-$N_5,N_5$')-di-n-propyl ether dihydrochloride, ω:ω'-di-($N_1,N_1$'-p-chlorophenyldiguanido-$N_5,N_5$')-di-n-propyl ether tetrahydrochloride, 1,6-di-($N_1,N_1$'-2,4-dichlorophenyldiguanido-$N_5,N_5$')hexane tetrahydrochloride, 1,6-di-($N_1,N_1$'-p-methylphenyldiguanido-$N_5,N_5$') hexane dihydrochloride, 1,6-di-($N_1,N_1$'-2,4,5-trichlorophenyldiguanido-$N_5,N_5$')hexane tetrahydrochloride, 1,6-di-[$N_1,N_1$'-alpha-(p-chlorophenyl) ethyldiguanido-$N_5,N_5$']hexane dihydrochloride, ω:ω-di-($N_1,N_1$'-p-chlorophenyldiguanido-$N_5,N_5$')m-xylene dihydrochloride, 1,12-di-($N_1,N_1$'-p-chlorophenyldiguanido-$N_5,N_5$') dodecane dihydrochloride, 1,10-di-($N_1,N_1$'-phenyldiguanido-$N_5,N_5$')decane tetrahydrochloride, 1,12-di-($N_1,N_1$'-phenyldiguanido-$N_5,N_5$')dodecane tetrahydrochloride, 1,6-di-($N_1,N_1$'-o-chlorophenyldiguanido-$N_5,N_5$')hexane dihydrochloride, 1,6-di-($N_1,N_1$'-o-chlorophenyldiguanido-$N_5,N_5$')hexane tetrahydrochloride, ethylene-bis-(1-tolylbiguanide), ethylene-bis-(p-tolylbiguanide), ethylene-bis-(3,5-dimethylphenylbiguanide), ethylene-bis-(p-tert-amylphenylbiguanide), ethylene-bis-(nonylphenylbiguanide), ethylene-bis-(phenylbiguanide), ethylene-bis-(N-butylphenylbiguanide), ethylene-bis-(2,5-diethoxyphenylbiguanide), ethylene-bis-(2,4-dimethylphenylbiguanide), ethylene-bis-(o-diphenylbiguanide), ethylene-bis-(mixed amylnaphthylbiguanide), N-butylethylene-bis-(phenylbiguanide), trimethylene-bis-(o-tolylbiguanide), N-butyltrimethylene-bis-(phenyl biguanide), and the corresponding salts such as acetates, gluconates, hydrochlorides, hydrobromides, citrates, bisulfites, fluorides, polymaleates, n-cocosalkylsarcosinates, phosphites, hypophosphites, perfluorooctanoates, silicates, sorbates, salicylates, maleates, tartrates, fumarates, ethylenediamintetraacetates, iminodiacetates, cinnamates, thiocyanates, arginates, pyromellitates, tetracarboxybutyrates, benzoates, glutarates, monofluorphosphates, perfluorpropionates, and any mixtures thereof.

Also suitable are halogenated xylene and cresol derivatives such as p-chlorometacresol or p-chlorometaxylene, as well as natural antimicrobial active substances of vegetable origin (e.g. from roots or herbs), or animal or microbial origin. Antimicrobially acting surface-active quaternary compounds, a natural antimicrobial active substance of vegetable origin, and/or a natural antimicrobial active substance of animal origin, extremely preferably at least one natural antimicrobial active substance of vegetable origin from the group encompassing caffeine, theobromine, and theophylline, as well as essential oils such as eugenol, thymol, and geraniol, and/or at least one natural antimicrobial active substance of animal origin from the group encompassing enzymes such as milk protein, lysozyme, and lactoperoxidase, and/or at least one antimicrobially active surface-active quaternary compound having an ammonium, sulfonium, phosphonium, iodonium, or arsonium group, peroxo compounds, and chloro compounds can preferably be used. Substances of microbial origin (so-called bacteriozines) can also be used.

The quaternary ammonium compounds (QACs) suitable as antimicrobial active substances exhibit the general formula $(R^1)(R^2)(R^3)(R^4)N^+X^-$, in which $R^1$ to $R^4$ represent identical or different $C_1$-$C_{22}$ alkyl radicals, $C_7$-$C_{28}$ aralkyl radicals, or heterocyclic radicals, such that two (or even, in the case of aromatic bonding such as in pyridine, three) radicals form the heterocycle together with the nitrogen atom, for example a pyridinium or imidazolinium compound, and $X^-$ are halide ions, sulfate ions, hydroxide ions, or similar anions. For an optimum antimicrobial action, at least one of the radicals preferably has a chain length of 8 to 18, in particular 12 to 16, C atoms.

QACs can be produced by the reaction of tertiary amines with alkylating agents such as, for example, methyl chloride, benzyl chloride, dimethyl sulfate, dodecyl bromide, but also ethylene oxide. The alkylation of tertiary amines having a long alkyl radical and two methyl groups proceeds particularly easily; the quaternization of tertiary amines having two long radicals and one methyl group can also be carried out under mild conditions using methyl chloride. Amines that possess three long alkyl radicals or hydroxy-substituted alkyl radicals are less reactive, and are preferably quaternized with dimethyl sulfate.

Suitable QACs are, for example, benzalkonium chloride (N-alkyl-N,N-dimethylbenzylammonium chloride, CAS No. 8001-54-5), Benzalkon B (m,p-dichlorobenzyldimethyl-C12-alkylammonium chloride, CAS No. 58390-78-6), benzoxonium chloride (benzyldodecyl-bis-(2-hydroxyethyl)ammonium chloride), cetrimonium bromide (N-hexadecyl-N, N-trimethylammonium bromide, CAS No. 57-09-0), benzetonium chloride (N,N-dimethyl-N-[2-[2-[p-(1,1,3,3-tetramethylbutyl)phenoxy]ethoxy]ethyl]benzylammonium chloride, CAS No. 121-54-0), dialkyldimethylammonium chlorides such as di-n-decyldimethylammonium chloride (CAS No. 7173-51-5-5), didecyldimethylammonium bromide (CAS No. 2390-68-3), dioctyldimethylammonium chloride, 1-cetylpyridinium chloride (CAS No. 123-03-5), and thiazoline iodide (CAS No. 15764-48-1), as well as mixtures thereof. Particularly preferred QACS are benzalkonium chlorides having $C_8$-$C_{18}$ alkyl radicals, in particular $C_{12}$-$C_{14}$ alkylbenzyldimethylammonium chloride.

Benzalkonium halides and/or substituted benzalkonium halides are commercially obtainable, for example, as Barquat® from Lonza, Marquat® from Mason, Variquat® from Witco/Sherex, and Hyamine® from Lonza, as well as Bardac® from Lonza. Further commercially obtainable antimicrobial active substances are N-(3-chlorallyl)hexaminium chloride such as Dowicide® and Dowicil® from Dow, benzethonium chloride such as Hyamine® 1622 from Rohm & Haas, methylbenzethonium chloride such Hyamin® 10× from Rohm & Haas, cetylpyridinium chloride such Cepacol Chloride from Merrell Labs.

The antimicrobial active substances are used in quantities from 0.0001 wt % to 1 wt %, preferably from 0.001 wt % to 0.8 wt %, particularly preferably from 0.005 wt % to 0.3 wt %, and in particular from 0.01 to 0.2 wt %.

The washing or cleaning products according to the present invention can contain UV absorbers that are absorbed onto the treated textiles and improve the light-fastness of the fibers and/or the light-fastness of other formulation constituents. "UV absorbers" are understood as organic substances (light protection filters) that are capable of absorbing ultraviolet radiation and re-emitting the absorbed energy in the form of longer-wave radiation, e.g. heat.

Compounds that exhibit these desired properties are, for example, the compounds and derivatives of benzophenone, having substituents in the 2- and/or 4-position, that become effective by radiationless deactivation. Also suitable are substituted benzotriazoles, acrylates phenyl-substituted in the 3-position (cinnamic acid derivatives, optionally with cyano groups in the 2-position), salicylates, organic Ni complexes, and natural substances such as umbelliferon and body-derived urocanic acid. Particularly important are biphenyl derivatives and especially stilbene derivates, such as those described e.g. in EP 0728749 A and available commercially as Tinosorb® FD or Tinosorb® FR from Ciba. To be mentioned as UV-B absorbers are: 3-benzylidene camphor and 3-benzylidene norcamphor and its derivatives, e.g. 3-(4-methylbenzylidene)camphor, as described in EP 0693471 B1; 4-aminobenzoic acid derivatives, preferably 4-(dimethylamino)benzoic acid 2-ethylhexyl ester, 4-(dimethylamino)benzoic acid 2-octyl ester, and 4-(dimethylamino)benzoic acid amyl ester; esters of cinnamic acid, preferably 4-methoxycinnamic acid 2-ethylhexyl ester, 4-methoxycinnamic acid propyl ester, 4-methoxycinnamic acid isoamyl ester, 2-cyano-3,3-phenylcinnamic acid 2-ethylhexyl ester (octocrylene); esters of salicylic acid, preferably salicylic acid 2-ethylhexyl ester, salicylic acid 4-isopropylbenzyl ester, salicylic acid homomenthyl ester; benzophenone derivatives, preferably 2-hydroxy-4-methoxybenzophenone, 2-hydroxy-4-methoxy-4'-methylbenzophenone, 2,2'-dihydroxy-4-methoxy-benzophenone; esters of benzalmalonic acid, preferably 4-methoxybenzalmalonic acid di-2-ethylhexyl ester; triazine derivatives such as, for example, 2,4,6-trianilino-(p-carbo-2'-ethyl-1'-hexyloxy)-1,3,5-triazine and octyl triazone as described in EP 0818450 A1, or dioctyl butamido triazone (Uvasorb® HEB); propane-1,3-diones such as, for example, 1-(4-tert.butylphenyl)-3-(4'-methoxyphenyl)propane-1,3-dione; ketotricyclo (5.2.1.0)decane derivatives, such as those described in EP 0694521 B1. Also suitable are 2-phenylbenzimidazole-5-sulfonic acid and its alkali, alkaline-earth, ammonium, alkylammonium, alkanolammonium, and glucammonium salts; sulfonic acid derivatives of benzophenones, preferably 2-hydroxy-4-methoxybenzophenone-5-sulfonic acid and its salts; sulfonic acid derivatives of 3-benzylidene camphor, for example 4-(2-oxo-3-bornylidenemethyl)-benzenesulfonic acid and 2-methyl-5-(2-oxo-3-bornylidene)sulfonic acid and its salts.

Typical UV-A filters that are possibilities are, in particular, derivatives of benzoylmethane such as, for example, 1-(4'-tert.butylphenyl)-3-(4'-methoxyphenyl)propane-1,3-dione, 4-tert.butyl-4'-methoxydibenzoyl-methane (Parsol 1789), 1-phenyl-3-(4'-isopropylphenyl)-propane-1,3-dione, and enamine compounds as described in DE 19712033 A1 (BASF). The UV-A and UV-B filters can, of course, also be used in mixtures. In addition to the aforementioned soluble substances, insoluble light-protection pigments, namely finely dispersed, preferably nanoized metal oxides or salts, are also possible for this purpose. Examples of suitable metal oxides are, in particular, zinc oxide and titanium oxide, and also oxides of iron, zirconium, silicon, manganese, aluminum, and cerium, as well as mixtures thereof. Silicates (talc), barium sulfate, or zinc stearate can be used as salts. The oxides and salts are already used in the form of pigments for skin-care and skin-protection emulsions and decorative cosmetics. The particles should have an average diameter of less than 100 nm, preferably between 5 and 50 nm, and in particular between 15 and 30 nm. They can have a spherical shape, but particles of this kind that possess an ellipsoidal shape, or one otherwise deviating from the spherical conformation, can also be used. The pigments can also be present in surface-treated form, i.e. hydrophilized or hydrophobized. Typical examples are coated titanium dioxides such as, for example, titanium dioxide T 805 (Degussa) or Eusolex® T2000 (Merck); suitable as hydrophobic coating agents therefor are preferably silicones and, particularly preferably, trialkoxyoctylsilanes or simethicones. Micronized zinc oxide is preferably used. Further suitable UV light protection filters may be gathered from the overview by P. Finkel in SÖFW-Journal 122 (1996), p. 543.

The UV absorbers are usually used in quantities from 0.01 wt % to 5 wt %, preferably 0.03 wt % to 1 wt %.

Products according to the present invention can contain enzymes in order to enhance washing or cleaning performance, all enzymes established in the existing art for those purposes being usable in principle. These include, in particular, further proteases, amylases, lipases, hemicellulases, cellulases, or oxidoreductases, as well as preferably mixtures thereof. These enzymes are, in principle, of natural origin; proceeding from the natural molecules, improved variants are available for use in washing and cleaning products and are correspondingly preferred for use. Products according to the present invention contain enzymes preferably in total amounts from $1 \times 10^6$ to 5 wt %, based on active protein.

Among the further proteases, those of the subtilisin type are preferred. Examples thereof are the subtilisins BPN' and Carlsberg, protease PB92, subtilisins 147 and 309, the alkaline protease from *Bacillus lentus*, subtilisin DY, and the enzymes (to be classified as subtilases but no longer as subtilisins in the strict sense) thermitase, proteinase K, and proteases TW3 and TW7. Subtilisin Carlsberg is obtainable in further developed form under the trade name Alcalase® from Novozymes A/S, Bagsvaerd, Denmark. Subtilisins 147 and 309 are marketed by Novozymes under the trade names Esperase® and Savinase®, respectively. The variants listed under the designation BLAP®, which are described in particular in WO 92/21760 A1, WO 95/23221 A1, WO 02/088340 A2, and WO 03/038082 A2, are derived from the protease from *Bacillus lentus* DSM 5483 (WO 91/02792 A1). Additional usable proteases from various *Bacillus* sp. and *B. gibsonii* are evident from the Patent Applications WO 03/054185 A1, WO 03/056017 A2, WO 03/055974 A2, and WO 03/054184 A1 already mentioned earlier.

Further usable proteases are, for example, the enzymes obtainable under the trade names Durazym®, Relase®, Everlase®, Nafizym, Natalase®, Kannase®, and Ovozymes® from Novozymes, under the trade names Purafect®, Purafect® OxP and Properase® from Genencor, under the trade name Protosol® from Advanced Biochemicals Ltd., Thane, India, under the trade name Wuxi® from Wuxi Snyder Bioproducts Ltd., China, under the trade names Proleather® and Protease P® from Amano Pharmaceuticals Ltd., Nagoya, Japan, and under the designation Proteinase K-16 from Kao Corp., Tokyo, Japan.

Examples of amylases usable according to the present invention are the α-amylases from *Bacillus licheniformis*, from *B. amyloliquefaciens*, or from *B. stearothermophilus*, and their further developments improved for use in washing and cleaning products. The enzyme from *B. licheniformus* is available from Novozymes under the name Termamyl®, and from Genencor under the name Purastar® ST. Additionally developed products of these α-amylases are available from Novozymes under the trade names Duramyl® and Termamyl® ultra, from Genencor under the name Purastar® OxAm, and from Daiwa Seiko Inc., Tokyo, Japan, as Keistase®. The α-amylase from *B. amyloliquefaciens* is marketed by Novozymes under the name BAN®, and derived variants of the α-amylase from *B. stearothermophilus* are marketed, likewise by Novozymes, under the names BSG® and Novamyl®.

Additionally to be highlighted for this purpose are the α-amylase from *Bacillus* sp. A 7-7 (DSM 12368) disclosed in Application WO 02/10356 A2 and the cyclodextrin-glucanotransferase (CGTase) from *B. agaradherens* (DSM 9948) described in Application WO 02/44350 A2. Also usable are the amylolytic enzymes which are described in Application WO 03/002711 A2, and those described in Application WO 03/054177 A. Fusion products of the aforesaid molecules, for example those from Application DE 10138753 A1, also likewise usable.

The further developments of the α-amylase from *Aspergillus niger* and *A. oryzae*, obtainable from Novozymes under the trade names Fungamyl®, are also suitable. A further commercial product is, for example, Amylase-LT®.

Products according to the present invention can contain lipases or cutinases, in particular because of their triglyceride-cleaving activities but also in order to generate peracids in situ from suitable precursors. These include, for example, the lipases obtainable originally from *Humicola lanuginosa* (*Thermomyces lanuginosus*) or further developed lipases, in particular those having the D96L amino-acid exchange. They are marketed, for example, by Novozymes under the trade names Lipolase®, Lipolase® Ultra, LipoPrime®, Lipozyme®, and Lipex®. The cutinases that were originally isolated from *Fusarium solani* pisi and *Humicola insolens* are also usable. Usable lipases are likewise obtainable from the Amano company under the designations Lipase CE®, Lipase P®, Lipase B®, or Lipase CES®, Lipase AKG®, *Bacillis* sp. Lipase®, Lipase AP®, Lipase M-AP®, and Lipase AML®. The lipases and cutinases from Genencor, whose starting enzymes were originally isolated from *Pseudomonas mendocina* and *Fusarium solanii*, are usable, for example. To be mentioned as further important commercial products are the preparations M1 Lipase® and Lipomax® originally marketed by Gist-Brocades, and the enzymes marketed by Meito Sangyo KK, Japan under the names Lipase MY-30®, Lipase OF®, and Lipase PL®, as well as the Lumafast® product of Genencor.

Products according to the present invention can, especially if they are intended for the treatment of textiles, contain cellulases, depending on the purpose, as pure enzymes, as enzyme preparations, or in the form of mixtures in which the individual components advantageously complement one another in terms of their various performance aspects. These performance aspects include, in particular, contributions to primary washing performance, to the secondary washing performance of the product (anti-redeposition effect or graying inhibition), and brightening (fabric effect), or even exertion of a "stone-washed" effect.

A usable fungus-based cellulase preparation rich in endoglucanase (EG), and its further developments, are offered by Novozymes under the trade name Celluzyme®. The products Endolase® and Carezyme®, likewise obtainable from Novozymes, are based on the 50-kD EG and 43-kD EG, respectively, from *H. insolens* DSM 1800. Additional usable commercial products of this company are Cellusoft® and Renozyme®. The latter is based on Application WO 96/29397 A1. Improved-performance cellulase variants may be gathered, for example, from Application WO 98/12307. Also usable are the cellulases disclosed in Application WO 97/14804 A1, for example the 20-kD EG from *Melanocarpus* that is disclosed therein and is available from AB Enzymes, Finland, under the trade names Ecostone® and Biotouch®. Further commercial products of AB Enzymes are Econase® and Ecopulp®. Other suitable cellulases from *Bacillus* sp. CBS 670.93 and CBS 669.83 are disclosed in WO 96/34092 A2, the one from *Bacillus* sp. CBS 670.93 being obtainable from Genencor under the trade name Puradax®. Further commercial products of Genencor are "Genencor detergent cellulase L" and IndiAge® Neutra.

In particular in order to remove certain problem stains, products according to the present invention can contain further enzymes that are grouped under the term "hemicellulases." These include, for example, mannanases, xanthanylases, pectinlyases (pectinases), pectinesterases, pectatelyases, xyloglucanases (xylanases), pullulanases, and β-glucanases. Suitable mannanases are obtainable, for example, under the names Gamanase® and Pektinex AR® from Novozymes, under the name Rohapec® B1L from AB Enzymes, and under the name Pyrolase® from Diversa Corp., San Diego, Calif., USA. A suitable β-glucanase from a *B. alcalophilus* is evident, for example, from Application O 99/06573 A1. The β-glucanase recovered from *B. subtilis* is available under the name Cereflo® from Novozymes.

To enhance the bleaching effect, washing and cleaning products according to the present invention can contain oxidoreductases, for example oxidases, oxygenases, catalases, peroxidases such as halo-, chloro-, bromo-, lignin, glucose, or manganese peroxidases, dioxygenases, or laccases (phenoloxidases, polyphenoloxidases). Suitable commercial products that may be mentioned are Denilite® 1 and 2 of Novozymes. Advantageously, preferably organic, particularly preferably aromatic compounds that interact with the enzymes are additionally added in order to enhance the activity of the relevant oxidoreductases (enhancers) or, if there is a large difference in redox potentials between the oxidizing enzymes and the stains, to ensure electron flow (mediators).

The enzymes used in the products according to the present invention either derive originally from microorganisms, for example of the genera *Bacillus, Streptomyces, Humicola*, or *Pseudomonas*, and/or are produced, using biotechnological methods known per se, by suitable microorganisms, e.g. by transgenic expression hosts of *Bacillus* or filamentous fungus genera.

Purification of the relevant enzymes is favorably accomplished by way of methods established per se, for example by precipitation, sedimentation, concentration, filtration of the liquid phases, microfiltration, ultrafiltration, the action of chemicals, deodorization, or suitable combinations of these steps.

Products according to the present invention can have the enzymes added to them in any form established according to the existing art. These include, for example, the solid preparations obtained by granulation, extrusion, or lyophilization or, especially in the case of liquid or gelled products, solutions of the enzymes that are advantageously as concentrated as possible, anhydrous, and/or with stabilizers added.

Alternatively, the enzymes can be encapsulated for both the solid and the liquid administration form, for example by spray-drying or extrusion of the enzyme solution together with a preferably natural polymer, or in the form of capsules, for example ones in which the enzymes are enclosed e.g. in a solidified gel, or in those of the core-shell type, in which an enzyme-containing core is covered with a protective layer impermeable to water, air, and/or chemicals. Further active substances, for example stabilizers, emulsifiers, pigments, bleaching agents, or dyes, can additionally be applied in superposed layers. Such capsules are applied in accordance with methods known per se, for example by vibratory or rolling granulation or in fluidized-bed processes. Such granulated materials are advantageously low in dust, e.g. as a result of the application of polymeric film-forming agents, and are stable in storage due to the coating.

It is additionally possible to package two or more enzymes together, so that a single granulated material possesses multiple enzyme activities.

A protein and/or enzyme contained in a product according to the present invention can be protected, especially during storage, against damage such as, for example, inactivation, denaturing, or decomposition, e.g. resulting from physical influences, oxidation, or proteolytic cleavage. An inhibition of proteolysis is particularly preferred in the context of microbial recovery of the proteins and/or enzymes, in particular when the products also contain proteases. Preferred products according to the present invention contain stabilizers for this purpose.

Reversible protease inhibitors are one group of stabilizers. Benzamidine hydrochloride, borax, boric acids, boronic acids, or their salts or esters are often used, among them principally derivatives having aromatic groups, e.g. ortho-, meta-, or para-substituted phenylboronic acids, in particular 4-formylphenylboronic acid, or the salts or esters of the aforesaid compounds. Peptide aldehydes, i.e. oligopeptides having a reduced C terminus, are also used for this purpose, in particular those made up of 2 to 50 monomers. Ovomucoid and leupeptin are among the reversible peptide-type protease inhibitors. Specific reversible peptide inhibitors for the protease subtilisin, as well as fusion proteins of proteases and specific peptide inhibitors, are also suitable for this purpose.

Further enzyme stabilizers are aminoalcohols such as mono-, di-, triethanol- and -propanolamine and mixtures thereof, aliphatic carboxylic acids up to $C_{12}$ such as, for example, succinic acid, other dicarboxylic acids, or salts of the aforesaid acids. End-group-terminated fatty acid amide alkoxylates are also suitable. Certain organic acids used as builders are additionally capable, as disclosed in WO 97/18287, of stabilizing a contained enzyme.

Lower aliphatic alcohols, but principally polyols, for example glycerol, ethylene glycol, propylene glycol, or sorbitol, are other frequently used enzyme stabilizers. Diglycerol phosphate also protects against denaturing due to physical influences. Calcium and/or magnesium salts are likewise used, for example calcium acetate or calcium formate.

Polyamide oligomers or polymeric compounds such as lignin, water-soluble vinyl copolymers, or cellulose ethers, acrylic polymers, and/or polyamides stabilize the enzyme preparation with respect, inter alia, to physical influences or pH fluctuations. Polyamine-N-oxide-containing polymers act simultaneously as enzyme stabilizers and as color transfer inhibitors. Other polymeric stabilizers are linear $C_8$-$C_{18}$ polyoxyalkylenes. Alkylpolyglycosides can also stabilize the enzymatic components of the product according to the present invention, and preferably are capable of additionally improving their performance. Crosslinked nitrogen-containing compounds preferably perform a dual function as soil-release agents and as enzyme stabilizers. Hydrophobic non-ionic polymer stabilizes, in particular, a cellulose that may optionally be contained.

Reducing agents and antioxidants increase the stability of the enzymes with respect to oxidative breakdown; sulfur-containing reducing agents are common, for example, for this purpose. Other examples are sodium sulfite and reducing sugars.

Combinations of stabilizers are particularly preferred for use, for example those made up of polyols, boric acid and/or borax, the combination of boric acid or borate, reducing salts, and succinic acid or other dicarboxylic acids, or the combination of boric acid or borate with polyols or polyamino compounds and with reducing salts. The action of peptide aldehyde stabilizers is favorably increased by the combination with boric acid and/or boric acid derivatives and polyols, and further enhanced by the additional action of divalent cations, for example calcium ions.

Because products according to the present invention can be offered in all conceivable forms, enzymes or proteins according to the present invention in all formulations appropriate for addition to the respective products each represent embodiments of the present invention. These include, for example, liquid formulations, solid granulated materials, or capsules.

The encapsulated form is a good choice in order to protect the enzymes or other ingredients from other constituents, for example bleaches, or in order to enable controlled release. Depending on the size of these capsules, a distinction is made among milli-, micro-, and nanocapsules, microcapsules being particularly preferred for enzymes. Such capsules are disclosed, for example, by Patent Applications WO 97/24177 and DE 19918267. One possible encapsulation method involves encapsulating the proteins, proceeding from a mixture of the protein solution with a solution or suspension of starch or a starch derivative, in that substance. An encapsulation method of this kind is described by Application WO 01/38471.

In the case of solid products, the proteins can be used, for example, in dried, granulated, and/or encapsulated form. They can be added separately, i.e. as a separate phase, or together with other constituents in the same phase, with or without compaction. If microencapsulated, enzymes are processed in solid form, the water is then removed, using methods known from the existing art such as spray drying, centrifuging, or resolubilization, from the aqueous solutions resulting from processing. The particles obtained in this fashion usually have a particle size of between 50 and 200 μm.

Liquid, gelled, or pasty products according to the present invention can have the enzymes, as well as the protein according to the present invention, added to them on the basis of a protein recovery and preparation in concentrated aqueous or nonaqueous solution, suspension, or emulsion performed according to the existing art, but also in gel form or in encapsulated form or as a dried powder. Washing or cleaning products according to the present invention of this kind are generally manufactured by simply mixing the ingredients, which can be introduced into an automatic mixer in bulk or as solutions.

In addition to their primary washing performance, the proteases contained in washing products can further perform the function of activating other enzymatic constituents by proteolytic cleavage, or inactivating them after an appropriate contact time, as has been disclosed, for example, in Applications WO 94/29426 or EP 747471. Comparable regulatory functions are also possible, however, by way of the protein according to the present invention. One embodiment of the present invention is furthermore such products having capsules made of protease-sensitive material, which capsules are hydrolyzed at an intended point in time, for example by proteins according to the present invention, and release their contents. A comparable effect can also be achieved with other multi-phase products.

A further embodiment is represented by products for treating textile raw materials or for textile care, which products contain an alkaline protease according to the present invention.

A further embodiment is represented by products for treating fibers or textiles with natural constituents, in particular those with wool or silk.

Natural fibers in particular, such as, wool or silk, are distinguished by a characteristic microscopic surface structure. Undesired effects such as felting occur in wool for example, as described in R. Breier in *Melliand Textilberichte* of Apr. 1, 2000 (p. 263). To prevent such effects, the natural raw materials are treated with products according to the present invention that contribute, for example, to smoothing of the flaked surface structure resulting from protein structures, and thus counteract felting.

In a preferred embodiment, the product having a protease according to the present invention is conceived in such a way that it can be used regularly as a care product, for example by being added to the washing process, utilized after washing, or applied independently of washing. The desired effect consists in obtaining a smooth surface structure of the textile over a long period of time and/or preventing and/or reducing damage to the fabric.

A separate subject of the invention is represented by methods for automatic cleaning of textiles or of hard surfaces, in which methods an alkaline protease according to the present invention is active in at least one of the method steps.

Preferred are those methods in which the alkaline protease according to the present invention is used in a quantity from 40 µg to 4 g, by preference from 50 µg to 3 g, particularly preferably from 100 µg to 2 g, and very particularly preferably from 200 µg to 1 g per application. All integral and non-integral values lying between these respective numbers are included.

Both manual and automatic methods can be utilized in the present invention, automatic methods being preferred because of their more-precise controllability regarding the quantities used and contact times.

Methods for cleaning textiles are generally characterized in that in multiple method steps, various substances having cleaning activity are applied onto the material being cleaned, and are washed off after the contact time; or that the material being cleaned is treated in another way with a washing product or a solution of that product. The same applies to methods for cleaning all materials other than textiles, which are grouped under the term "hard surfaces." All conceivable washing or cleaning methods can be supplemented in at least one of the method steps to include proteins according to the present invention, and then represent embodiments of the present invention.

Because preferred enzymes according to the present invention already naturally possess a protein-dissolving activity, and also exert it in media that otherwise possess no cleaning power, for example in a pure buffer, a single sub-step of such a method for automatic cleaning of textiles can include, if desired, alongside stabilizing compounds, salts, or buffer substances, an enzyme according to the present invention which is applied as the only component having cleaning activity. This represents a particularly preferred embodiment of the present invention.

In a further preferred embodiment of such methods, the relevant alkaline proteases according to the present invention are made available in the context of one of the formulations discussed above for products according to the present invention, preferably washing or cleaning products according to the present invention.

Preferred embodiments of this aspect of the invention are represented by methods for treating textile raw materials or for textile care, in which methods an alkaline protease according to the present invention becomes active in at least one of the method steps.

Preferred are methods for cleaning textile raw materials, fibers, or textiles with natural constituents, and very particularly for those with wool or silk.

These can involve, for example, methods in which materials for processing into textiles are prepared, e.g. for anti-felting treatment, or, for example, methods that supplement the cleaning of previously worn textiles to include a conditioning component. Because of the above-described action of proteases on natural, protein-containing raw materials, the methods involved are, in preferred embodiments, ones for treating textile raw materials, fibers, or textiles with natural constituents, in particular with wool or silk.

A separate aspect of the invention is represented by the use of an above-described alkaline protease according to the present invention for cleaning textiles or hard surfaces.

The concentration ranges discussed above apply, in correspondingly preferred fashion, to these uses.

Proteases according to the present invention can be used, in particular in accordance with the above-described properties and the above-described methods, in order to eliminate protein-containing contaminants from textiles or from hard surfaces. Embodiments are represented by, for example, hand laundering, manual removal of spots from textiles or hard surfaces, or utilization in conjunction with an automatic method.

In a preferred embodiment of this use, the relevant alkaline proteases according to the present invention are made available in the context of one of the above-discussed formulations for products according to the present invention, preferably washing or cleaning products.

A further embodiment of the invention is represented by the use of an alkaline protease according to the present invention to activate or deactivate ingredients of washing or cleaning products.

Protein constituents of washing or cleaning products can be inactivated by the action of a protease. It is a subject of the present invention to utilize in deliberate fashion this otherwise rather undesirable effect. It is likewise possible, as described above, for a different component to be activated by proteolysis only if, for example, it represents a hybrid protein of the actual enzyme and the inhibitor that matches it, as has been disclosed, for example, in Application WO 00/01831 A2. Another example of such a regulation process is that in which an active component, in order to protect or control its activity, is present in encapsulated fashion in a material that is attacked by proteolysis. Proteins according to the present invention can thus be used for inactivation, activation, or release reactions, in particular in multi-phase products.

In accordance with what has been said above, the following uses also represent embodiments of the present invention:
use of an alkaline protease according to the present invention
    in order to recover or treat raw materials or intermediate products in textile manufacturing, in particular in order to remove protective layers from fabrics;

use of an alkaline protease according to the present invention to treat textile raw materials or for textile care; and, preferred thereamong corresponding use for textile raw materials, fibers, or textiles with natural constituents, and very particular for those with wool or silk.

The present invention is also encompases those products containing an alkaline protease according to the present invention that are cosmetics, including all types of cleaning and conditioning products for human skin or hair, in particular cleaning products.

Proteases also play a critical role in the cell renewal processes in human skin (desquamation) (T. Egelrud et al., *Acta Derm. Venerol.*, Volume 71 (1991), pp. 471-474). Proteases are accordingly also used as bioactive components in skincare products in order to assist the breakdown of the desmosome structures that proliferate in dry skin. The use for cosmetic purposes of subtilisin proteases having amino-acid exchanges in positions R99G/A/S, S154D/E and/or L211D/E is described, for example, in WO 97/07770 A1. Corresponding to what has been said above, proteases according to the present invention can be further developed by way of the corresponding point mutations. Proteases according to the present invention, in particular those whose activity is controlled e.g. on the basis of mutagenesis or by the addition of appropriate substances interacting with them, are therefore also suitable as active components in skin- or hair-cleaning or conditioning products. Particularly preferred are those preparations of these enzymes that, as described above, are stabilized, for example, by coupling to macromolecular carriers (cf. U.S. Pat. No. 5,230,891), and/or are derivatized by point mutations at highly allergenic positions, so that they exhibit greater skin compatibility for humans.

Corresponding cosmetic cleaning and conditioning methods, and the use of such proteolytic enzymes for cosmetic purposes, are accordingly also incorporated into this subject of the invention, in particular into corresponding products such as, for example, shampoos, soaps, or washing lotions, or into conditioning products that are offered, for example, in the form of cremes. Use in a peeling medication or for the manufacture thereof is also included in this embodiment.

In addition to use in washing and cleaning products and cosmetics, numerous possible applications of proteases, in particular subtilases, are established in the existing art. An overview thereof is provided, for example, by the manual "Industrial enzymes and their applications" by H. Uhlig, Wiley, N.Y., 1998. All these technologies can be supplemented to include alkaline proteases according to the present invention. If it should be found that they can be further developed by the use of proteases according to the present invention, such improvements also form an aspect of the invention. Included therein are, in particular, the following areas of application:

use of an alkaline protease according to the present invention for the biochemical analysis or the synthesis of low-molecular-weight compounds or of proteins;

in preferred fashion, use for end-capping-group determination in the context of a peptide sequence analysis;

use of an alkaline protease according to the present invention for the preparation, purification, or synthesis of natural substances or biologically useful substances, preferably in the context of corresponding products or methods;

use of an alkaline protease according to the present invention for the synthesis of proteins or other low-molecular-weight chemical compounds;

use of an alkaline protease according to the present invention for the treatment of natural raw materials, in particular for surface treatment, very particularly in a method for treating leather, preferably in the context of corresponding products or methods;

use of an alkaline protease according to the present invention for the treatment of photographic films, in particular for the removal of gelatin-containing or similar protective layers; and use of an alkaline protease according to the present invention for the manufacture of foods or animal feeds.

The utilization of alkaline proteases in all further technological sectors for which it proves to be suitable is included, in principle, in the present invention.

The Examples below explain the invention further:

EXAMPLES

All the molecular-biological processes employ standard methods, as indicated e.g. in Fritsch, Sambrook and Maniatis, "Molecular cloning: a laboratory manual," *Cold Spring Harbour Laboratory Press*, New York, 1989, or comparable relevant works. The enzymes and kits were used in accordance with the respective manufacturer's instructions.

Example 1

Recovering Cell Material from Soil Habitats

Soil samples were taken from various locations in Germany, placed in water, and allowed to stand for 30 minutes to sediment suspended materials. The supernatant was plated out onto 5% agar plates with HSP10 solid medium (0.1 g yeast extract, Difco, Heidelberg; 0.1 g casein peptone, trypsin-digested, Difco; 0.1 g soluble starch (Merck, order no. 1.01251); 2 g $Na_2CO_3$; distilled water to make 1000 ml; pH 10) and cultured for approx. two weeks at 30° C. The resulting bacterial films were recovered mechanically from the agar surface.

Example 2

Setting up an Expression Gene Bank

The expression system selected was the vector pUC18 (GenBank, National Institutes of Health, Bethesda, Md., USA; access no: L08752; FIG. 5) in *Escherichia coli* DH12S. This vector carries the β-galactosidase promoter, inducible by the addition of IPTG, of the lac operon, thus making possible controlled inducible expression of DNA integrated into the multiple cloning sites. The DH12S strain is suitable for IPTG induction because of its laclq genotype, and is advantageous for protease activity screening because it exhibits sufficiently low endogenous proteolytic activity. Preliminary experiments had shown that *E. coli* JM109 also meets the same criteria.

Processing of the DNA from the sample obtained according to Example 1 was performed in accordance with Zhou et al. (1996), *Appl. Environ. Microbiol.*, Volume 62, pp. 316-322. This purified metagenomic DNA (see below) was subjected to a preparative partial restriction with the restriction enzyme Alu I to present fragment sizes in the range of 5-10 kb.

For this, firstly the optimum restriction incubation duration was determined by recording enzyme kinetics. This was done by incubating 2.8 μg of the DNA preparation in the corresponding reaction buffer offered by the manufacturers of Alu I (New England Biolabs, Schwalbach, Germany; catalog no.

R0137S) at 37° C. The reaction was started in a total volume of 21 µl by adding 0.2 U Alu I per pg of DNA, and at two-minute intervals thereafter a respective 1.5 µl portion was withdrawn from the batch, in which portion the reaction was immediately terminated by adding 10 mM Tris/HCl, pH 7.0; 20% glycerol; and 0.1% SDS, and cooling to 0° C. The optimum restriction time for partial digestion was ascertained by subsequent analysis on a 0.7% agarose gel. For isolation of the DNA isolated according to Example 1, that duration is approx. 6 to 7 min in order to obtain fragments in the size range of 5-10 kb.

Preparative partial digestion was accordingly performed in 15 to 20 parallel batches. After appropriate halting of the reaction, the batch was electrophoretically separated on a preparative 0.7% agarose gel, the gel region having DNA in the 5-10 kb size range was cut out, and the DNA was isolated by electroelution in dialysis tubes at 4° C. The DNA was then precipitated using ⅒ volume 3 M sodium acetate and 2.5 times the volume of ethanol, and resuspended in a suitable volume. Gel electrophoresis, electroporation, and precipitation were repeated for further separation of any smaller DNA fragment that might have been present.

450 ng of the fragmented metagenomic DNA thereby obtained was ligated overnight at 16° C. in a total volume of 15 µl with 100 ng of the pUC18 vector, with the addition of 400 NEB units of T4 DNA ligase in 1× ligase buffer. This vector had previously been linearized with Sma I and dephosphorylated with alkaline phosphatase from calf thymus.

The transformation of competent *E. coli* DH12S cells (Gibco Life Technologies, Karlsruhe, catalog no. 18312017) was accomplished by electrotransformation. For this, 1 µl of ligation mixture and 25 µl of cells were mixed, incubated on ice for 1 min. in an electroporation cuvette, and treated according to the manufacturer's instruction in an electroporator (BTX® ECM630, Genetronics Inc. San Diego, USA). Immediate transfer into 1 ml SOC medium (2% Bacto Tryptone; 0.5% yeast extract; 10 mM NaCl; 2.5 mM KCl; pH 7.0, adjusted with NaOH; autoclaved; supplemented with 10 mM $MgSO_4$ and $MgCl_2$ and with 20 mM D(+) glucose) was followed by a recovery phase of 1 h at 37° C. and plating, as in Example 1, onto agar plates with HSP10 solid medium.

Example 3

Screening for Proteolytic Activity

In order to investigate the quality of the gene bank produced according to Example 2 in *E. coli* DH12S, the total number of primary transformants generated, and the number of insert-carrying clones, were determined via blue/white selection by test plating. For this, 1- and 10-µl portions of the transformation batch were plated onto 5% agar plates with LB medium (10 g tryptone, 5 g yeast extract, 5 g NaCl, 1 ml 1 N NaOH per l), to which 100 µg/ml ampicillin, 0.2 mM (or 4 µg/ml) IPTG, and 0.2 mM (or 1 µg/ml) X-Gal were additionally added, plated out, and incubated overnight at 37° C. The plasmids from 10 white colonies (i.e. transformants) were isolated by mini-preparation (kit from Qiagen, Hilden, Germany), a restriction digestion was performed using restriction enzymes Sac I and Hind III to excise the insert (cf. FIG. 3), and the fragments were separated on a 0.7% agarose gel. All the vectors in fact contained inserts approx. 5 to 10 kb in size.

Screening of the gene bank generated according to Example 2 was accomplished on 14-cm diameter 5% agar plates using LB medium ampicillin/IPTG/X-Gal (see above) and additionally 2% skim milk powder (Difco, order no. 232100). On 10 of these selection agar plates, volumes of the transformation batch of approx. 10,000 cfu, corresponding to the titer of the bank, were evenly plated out using glass spheres (primary plating).

After 16 hours of incubation at 37° C., the plates were incubated for up to two weeks at 28° C. During this time, protease-forming clones became evident as clarification haloes in the turbid substrate. Separate cell lysis in order to detect non-exported proteases was not necessary. Plasmid-mediated protease formation was validated by once again isolating the primary clones and then isolating the relevant insert-containing pUC18 vectors, retransforming, and rescreening (as above; secondary plating). The transformants proceeding from this likewise displayed halo formation on a skim-milk medium, and thus confirmed localization of a protease gene on the respective cloned DNA fragment.

Example 4

Sequence Analysis of a Proteolytically Active Clone

The plasmid DNA from a protease-positive clone obtained according to Example 3 was isolated using standard methods, and the insert was prepared by Sac I/Hind III digestion (see above) and sequenced using standard methods. The primer according to SEQ ID NOS. 1 and 2, flanking the insert, was used first for this, followed by so-called primer walking as known from the existing art (R. J. Kaiser et al. (1989): "Specific primer-directed DNA sequencing using automated fluorescence detection," *Nucl. Acids Res.*, 17 (15), pp. 6087-6102).

Sequencing of this clone yielded a region having an open reading frame (ORF), whose DNA sequence is indicated in SEQ ID NO. 3. The amino-acid sequence derived therefrom is disclosed as SEQ ID NO. 4. The latter probably encompasses the complete preprotein, although it is not unequivocally established where the signal peptide ends; possibly with one of positions 31 or 34.

Using this information, a homology comparison was performed with the heretofore known proteases in the "non-redundant gene bank" (Altschul, Stephan F., Thomas L. Madden, Alejandro A. Schaffer, Jinghui Zhang, Hheng Zhang, Webb Miller, and David J. Lipman (1997): "Gapped BLAST and PSI-BLAST: a new generation of protein database search programs," *Nucleic Acids Res.*, 25, pp. 3389-3402). This analysis yielded, as the most similar described enzyme, a glutamate-specific endopeptidase of the S2B family from *Bacillus licheniformis*. It bears the GenBank access number P80057 (National Center for Biotechnology Information NCBI, National Institutes of Health, Bethesda, Md., USA). The identity at the amino-acid level, ascertained (like all subsequent homology values) with the computer program Vector NTI® Suite 7.0, obtainable from InforMax, Inc., Bethesda, USA, using the predetermined default parameters, was 21.9% (cf. FIG. 1). Further proteins found in this search that still appear most similar at the amino-acid level are summarized in Table 1 below. Except for the last two, however, these are merely database entries of putative enzyme sequences, which have not been detected as active enzymes.

TABLE 1

Putative sequences found to be most similar on the amino-acid level

| Access no. | Description | Identity [%] |
|---|---|---|
| NP_693914 | Hypothetical protein from *Oceanobacillus iheyensis* HTE831 | 30.3 |

TABLE 1-continued

Putative sequences found to be most similar on the amino-acid level

| Access no. | Description | Identity [%] |
|---|---|---|
| NP_642686 | Conserved hypothetical protein from *Xanthomonas axonopodis* pv. *citri* | 28.3 |
| NP_297821 | Hypothetical protein from *Xylella fastidiosa* 9a5c | 26.7 |
| ZP_00059013 | Hypothetical protein from *Thermobifida fusca* | 24.6 |
| P80057 | Glutamyl endopeptidase precursor (glutamate-specific endopeptidase, GSE) | 21.9 |
| NP_388106 | Extracellular metalloprotease from *Bacillus subtilis* | 19.0 |

On the DNA level, an identity of 45.9% is evident in positions 254 to 1311, as shown in FIG. 3, with the gene (SEQ ID NO. 7) of the glutamate-specific endopeptidase from *B. licheniformis* (GeneBank access no. D10060).

The protease that has been discovered is therefore a novel enzyme whose closest relatives exhibit only a very small degree of homology. A homology of 14.4% identity with the established *B. lentus* alkaline protease (SEQ ID NO. 5) (WO 97/21760 A1) is evident on the amino-acid level, over the entire length of this alkaline protease, and an identity of 46.2% on the nucleic-acid level, the latter once again in positions 254 to 1311 as shown in FIG. 3.

The fact that a V8 protease (or an S8 subtilase) was found to be the most similar enzyme must be viewed as an indication that this is a subtilase but not a subtilisin; the latter is a subgroup of the subtilases particularly rich in washing-product proteases. At the same time, because of the relationship with the V8 proteases, it can be allocated to the family of the metalloproteases.

The associated vector, having the designation 23-pUC (LP10/03), was deposited on Nov. 10, 2003 at the German Microorganism and Cell Culture Collection [Deutsche Sammlung von Mikroorganismen and Zellkulturen GmbH, DSMZ], Mascheroder Weg 1b, 38124, Braunschweig, where it bears the deposit number DSM 16017. The protease that is coded thereby is referred to as HP23.

Example 5

Quantitative Recovery of the Protease According to the Present Invention

The expression clone obtained according to Example 3 was placed in 100 ml LB medium (10 g/l tryptone, 5 g/l yeast extract, 10 g/l NaCl) and cultured in 500 ml Erlenmeyer flasks at 37° C. with agitation at 200 rpm.

The protease of interest can be recovered from these cultures by cell disintegration. For this, the cells are harvested by centrifugation (20 min, 5,000 g) and resuspended in 50 mM phosphate buffer, pH 7.8, as a 30% cell suspension. 600 μl of such a suspension has 1 g glass spheres added to it and is vigorously mixed for 1 min. on a vortexer, causing cell disintegration. The disintegrated suspension thereby obtained contains the protease, and is removed and used further.

Example 6

Biochemical Characterization of the Expression Clone According to Example 3

The protease quantitatively obtained according to Example 5 was biochemically characterized. In this context, the proteolytic activity was ascertained via a so-called MTP assay, based on a fluorescence-coupled casein substrate (BODIPY® FL Conjugate, Molecular Probes, Göttingen, Germany; order no. #6638), to which fluorophores (emitters) and quenchers are coupled. In the intact substrate, any fluorescence of the emitter is suppressed by the quencher. Upon hydrolysis of the casein, however, the oligopeptides, along with the groups coupled to them, move away from one another, and appropriate excitation results in fluorescence emission, the intensity of which thus represents a measure of the proteolysis.

For activity determination, 5 μl portions of a protease sample in accordance with Example 5 were each incubated in 100 mM Tris/HCl at the desired pH, and 4.5 μg/ml BODIPY® FL Conjugate, in a total volume of 100 μl for 1 hour at the temperature of interest. All the measurements indicated hereinafter were performed in 96-well microtitration plates (Opaque® Plates, black; Corning BV Life Sciences, Schiphol-Rijk, Netherlands; order no. #3915) using a FLUOstar® fluorescence meter (BMG Lab Technologies, Offenburg, Germany).

Temperature Profile

The measured value at pH 8.6 and 50° C. was set to 100%. With otherwise identical incubation at 37° C., 64% of this value was ascertained. This shows that the protease according to the present invention in accordance with SEQ ID NO. 4 is a protease which is more active at moderate than at low temperatures.

Stability with Respect to pH Fluctuations

To determine the stability with respect to pH fluctuations, samples of the novel protease were incubated at pH 7.6, pH 8.6, and pH 9.0, at 37° and 50° in each case. The results obtained are summarized in Table 2; in this context, the activity at 50° C. and pH 9.0 was set to 100% and the other values were referred thereto.

TABLE 2 pH profile, at low and moderate temperatures, of the protease according to the present invention in accordance with Example 5.

|  | pH 7.6 | pH 8.6 | pH 9.0 |
|---|---|---|---|
| 37° C. | 45% | 58% | 63% |
| 50° C. | 75% | 92% | 100% |

It is evident that this protease exhibits an alkaline pH optimum at both temperatures, and can in that regard be referred to as an alkaline protease.

Influence of Complexing Agents

The influence of complexing agents was investigated by adding 1 mM EDTA at pH 8.6 in the assay described above, specifically at 37° and at 50°. The measured value without the addition of EDTA was set to 100%. In contrast, the relative proteolytic activity at 50° C. was 103%, and at 37° C. in fact 124%. This enzyme therefore appears *a priori* to be well suited for use in washing and cleaning products.

Stability Measurement

To measure stability, the protease sample being used was first pre-incubated for 15 min. at 50° C. in 50 mM NaHCO$_3$ buffer, pH 10.9, and the residual activity was then measured in the aforesaid assay at 37° C. and 50° C., at pH 8.6 in each case. The activity of the same extract, without pre-incubation but with otherwise identical processing, was set in each case to 100%. A residual activity of 46% for 37° C. and 45% for 50° was ascertained in this fashion.

This is therefore a molecule that is relatively stable with respect to high pH values, practically irrespective of temperature.

Example 7

Contribution of Protease HP23 According to the Present Invention to Washing Performance at Low Temperature Textiles stained in standardized fashion, which had been obtained from the Federal Materials Testing and Research Agency [Eidgenössische Material-Prüfungs- und Versuchsanstalt, EMPA], St. Gallen, Switzerland, were used for this Example. The following stains and textiles were utilized: A (blood, milk, ink on cotton), B (blood, milk, ink on a polyester/cotton blend fabric), C (egg, soot on cotton).

Using this test material, a variety of washing product formulations were investigated launderometrically in terms of their washing performance. For this, a bath ratio of 1:12 was established in each case, and washing was performed for 30 min. at a temperature of 40° C. The respective product was dispensed at 5.9 g per liter of washing bath. Water hardness was 16° German hardness.

A baseline washing product formula of the following composition was used as the control washing product (all quantities in wt %): 4% linear alkylbenzenesulfonate (sodium salt), 4% $C_{12}$-$C_{18}$ fatty alcohol sulfate (sodium salt), 5.5% $C_{12}$-$C_{18}$ fatty alcohol with 7 EO, 1% sodium salt, 11% sodium carbonate, 2.5% amorphous sodium disilicate, 20% sodium perborate tetrahydrate, 5.5% TAED, 25% zeolite A, 4.5% polycarboxylate, 0.5% phosphonate, 2.5% granulated foam inhibitor, 5% sodium sulfate, remainder: water, optical brighteners, salts.

The protease according to the present invention and a control protease were added to this in parallel batches, each in activity-equalized fashion. The *B. lentus* alkaline protease F49 (WO 95/23221 A1; manufacturer: Biozym, Kundl, Austria) was used as a control. It possessed a specific activity (determinable according to the method indicated in the Description) of approx. 200,000 PU/g, yielding, at 0.2 wt %, an F49 concentration of approx. 40,000 PU per 100 g of the product and an activity of approx. 2,400 PU per liter of washing bath. Formulations were additionally produced that, omitting a corresponding quantity of salts, each contained 0.5% protease, i.e. two-and-a-half times the protease quantity. The protease according to the present invention was added to the same baseline formulation in the same activity concentrations. The wt % values indicated in the table below are thus correct for F49 and are approximately applicable for HP23.

After washing, the whiteness of the laundered textiles was measured in comparison with that of barium sulfate, which was standardized to 100%. The measurement was performed using a Datacolor SF500-2 spectrophotometer at 460 nm (UV blocking filter 3), 30 mm aperture, no gloss, D65 light type, 10°, d/8°. The results obtained are summarized in Table 3 below as percentage remission, i.e. as percentages compared to barium sulfate, together with the respective initial values. The averages of three measurements are indicated in each case. They allow a direct conclusion to be drawn as to the contribution of the enzyme ingredient to the washing performance of the product being used.

TABLE 3

Contribution of a protease according to the present invention to washing performance at a temperature of 40° C.

| Baseline washing product with | A | B | C |
|---|---|---|---|
| Initial value | 15.2 | 12.1 | 31.9 |
| control (no protease) | 21.8 | 14.4 | 50.4 |
| 0.2% HP23 | 23.8 | 16.6 | 61.7 |
| 0.2% *B. lentus* alkaline protease F49 | 29.3 | 24.2 | 70.3 |
| 0.5% HP23 | 26.6 | 19.2 | 67.9 |
| 0.5% *B. lentus* alkaline protease F49 | 33.9 | 33.0 | 71.4 |
| Standard deviation | 1.4 | 1.5 | 2.3 |

All three measurement series confirm that the protease according to the present invention results in an improvement in washing performance on protein-containing stains as compared with protease-free washing products. In other words, it displays a proteolytic activity even in the presence of denaturing agents such as, for example, surfactants. The values ascertained for the *B. lentus* alkaline protease F49 confirm that the experiments were performed correctly. Its measured values are, as expected, the highest, since this is a molecule optimized via point mutagenesis for this area of application (cf. WO 95/23221 A1).

Example 8

Contribution of Protease HP23 According to the Present Invention to Washing Performance at Higher Temperature For this Example, the batches of the previous Example were repeated, under otherwise identical conditions, at a temperature of 60° C. The results summarized in the table below were obtained:

TABLE 4

Contribution of a protease according to the present invention to washing performance at a temperature of 60° C.

| Baseline washing product with | A | B | C |
|---|---|---|---|
| Initial value | 15.2 | 12.1 | 31.9 |
| control (no protease) | 21.9 | 14.9 | 50.8 |
| 0.2% HP23 | 24.1 | 16.7 | 60.7 |
| 0.2% *B. lentus* alkaline protease F49 | 30.6 | 30.0 | 71.0 |
| 0.5% HP23 | 27.2 | 19.2 | 64.1 |
| 0.5% *B. lentus* alkaline protease F49 | 34.6 | 39.8 | 72.0 |
| Standard deviation | 1.3 | 1.6 | 2.1 |

This result confirms that of the previous experiment. Fortunately, protease HP23 according to the present invention is not appreciably denatured at 60° C., so that it is suitable in particular as a washing-product protease.

The invention claimed is:

1. An isolated alkaline protease that is at least 90% identical to SEQ ID NO: 4 or an isolated alkaline protease that is at least 90% identical to the amino acid sequence indicated in positions 32 to 327 of SEQ ID NO: 4.

2. The alkaline protease of claim 1 which is obtainable from a microorganism that is isolatable from a natural habitat or is encoded by a nucleic acid isolatable from a natural habitat.

3. The alkaline protease according to claim 2, wherein said microorganism is a microorganism producing said protease and selected from the group consisting of a fungus, a Gram-negative bacteria, and a Gram-positive bacterium.

4. The alkaline protease according to claim 1 which is stabilized via covalent coupling to a polymer.

5. The alkaline protease of claim 4 which is derivatized.

6. A product containing the alkaline protease according to claim 1.

7. The product according to claim 6, which is a washing or cleaning product.

8. The product according to claim 7, wherein said protease is present in an amount of about 2 μg to about 20 mg per gram of said product.

9. The product according to claim 8, wherein said protease is present in an amount of about 50 μg to 10 mg per gram of the product.

10. The product according to claim 6, further comprising at least one enzyme selected from the group consisting of proteases, amylases, cellulases, hemicellulases, oxidoreductases, and lipases.

* * * * *

UNITED STATES PATENT AND TRADEMARK OFFICE
CERTIFICATE OF CORRECTION

PATENT NO. : 7,811,076 B2 Page 1 of 1
APPLICATION NO. : 11/473708
DATED : October 12, 2010
INVENTOR(S) : Susanne Wieland et al.

It is certified that error appears in the above-identified patent and that said Letters Patent is hereby corrected as shown below:

In title page, item (73), please delete "Henkel AG & Co. KGaA" and insert -- BRAIN AG -- therefore.

Signed and Sealed this
Seventh Day of June, 2011

David J. Kappos
*Director of the United States Patent and Trademark Office*

SEQUENCE LISTING

<160> NUMBER OF SEQ ID NOS: 11

<210> SEQ ID NO 1
<211> LENGTH: 16

-continued

```
<212> TYPE: DNA
<213> ORGANISM: Artificial
<220> FEATURE:
<223> OTHER INFORMATION: Primer M13f

<400> SEQUENCE: 1
gtaaaacgac ggccag                                                    16

<210> SEQ ID NO 2
<211> LENGTH: 17
<212> TYPE: DNA
<213> ORGANISM: Artificial
<220> FEATURE:
<223> OTHER INFORMATION: Primer M13r

<400> SEQUENCE: 2
caggaaacag ctatgac                                                   17

<210> SEQ ID NO 3
<211> LENGTH: 984
<212> TYPE: DNA
<213> ORGANISM: Unknown
<220> FEATURE:
<223> OTHER INFORMATION: Isolated DNA, comprising a gene which codes for
      an Alkaline Protease
<220> FEATURE:
<221> NAME/KEY: CDS
<222> LOCATION: (1)..(984)
<223> OTHER INFORMATION: Gene coding for an Alkaline Protease

<400> SEQUENCE: 3 atg aca tca acc agg act ctg gcc aca agc ctc atg agc ctc acc acc        48
Met Thr Ser Thr Arg Thr Leu Ala Thr Ser Leu Met Ser Leu Thr Thr
1               5                   10                  15 gca gca ctg ttc gcc ctc tgc tct gcc ggg cag gcg acg gca gcc ccc        96
Ala Ala Leu Phe Ala Leu Cys Ser Ala Gly Gln Ala Thr Ala Ala Pro
            20                  25                  30 gca tcg ccg gac acg aag gac gtt gcc ggc gtc agc agc gcg gcc gtc       144
Ala Ser Pro Asp Thr Lys Asp Val Ala Gly Val Ser Ser Ala Ala Val
        35                  40                  45 acc gac acc agc ggc gcc gac tac tgg acg ccg gaa cgc atg cgt tcg       192
Thr Asp Thr Ser Gly Ala Asp Tyr Trp Thr Pro Glu Arg Met Arg Ser
    50                  55                  60 gcc atc ccg gcg gac gtc ctg gcc aag aag gcc gtg gaa cgg cag aag       240
Ala Ile Pro Ala Asp Val Leu Ala Lys Lys Ala Val Glu Arg Gln Lys
65                  70                  75                  80 tcc aac ccg gca gtc ctc ccg gag cag gcc aag ggc ccg gag acc aaa       288
Ser Asn Pro Ala Val Leu Pro Glu Gln Ala Lys Gly Pro Glu Thr Lys
                85                  90                  95 atc cag ggc tcc gca ccc cag gtc cag gcc aag gcc aac gcc agc gaa       336
Ile Gln Gly Ser Ala Pro Gln Val Gln Ala Lys Ala Asn Ala Ser Glu
            100                 105                 110 acc ccg gtg tcc cac atc ggc aag gtg ttc ttc acc ctc ggc ggc acc       384
Thr Pro Val Ser His Ile Gly Lys Val Phe Phe Thr Leu Gly Gly Thr
        115                 120                 125 aac tac gtc tgc tcg gca aac tcg gtg gtg tcc acc aac cgg aac acc       432
Asn Tyr Val Cys Ser Ala Asn Ser Val Val Ser Thr Asn Arg Asn Thr
    130                 135                 140 gtc tcc acc gcc ggc cac tgc ctc aat gaa ggc ccc gga gcc ttc gcc       480
Val Ser Thr Ala Gly His Cys Leu Asn Glu Gly Pro Gly Ala Phe Ala
145                 150                 155                 160 acc aag ttc acg ttc gtt ccc gcc tac ctg aac ggc tcc gca ccc tac       528
Thr Lys Phe Thr Phe Val Pro Ala Tyr Leu Asn Gly Ser Ala Pro Tyr
                165                 170                 175
```

```
gga aag tgg act gcc aag gcg ctg tac gcc ccc acc cag tgg agc tcg    576
Gly Lys Trp Thr Ala Lys Ala Leu Tyr Ala Pro Thr Gln Trp Ser Ser
            180                 185                 190 tca ggc agc atg gaa tac gac acg ggc ttc gcc gtc atg agc cag ctc    624
Ser Gly Ser Met Glu Tyr Asp Thr Gly Phe Ala Val Met Ser Gln Leu
            195                 200                 205 aac ggc cgc aac ctg gcc gac gtc gtc ggg gcc tcc ggg gtc agc ttc    672
Asn Gly Arg Asn Leu Ala Asp Val Val Gly Ala Ser Gly Val Ser Phe
        210                 215                 220 aac gcc gcc cgc ggc ctg gcc tac aag gcc ttc ggc tac ccg gcc gcc    720
Asn Ala Ala Arg Gly Leu Ala Tyr Lys Ala Phe Gly Tyr Pro Ala Ala
225                 230                 235                 240 tca ccg ttc aac ggc gaa tcg ctg aag agc tgc tcc ggc acc gcc acc    768
Ser Pro Phe Asn Gly Glu Ser Leu Lys Ser Cys Ser Gly Thr Ala Thr
                245                 250                 255 aac gat ccc tac aac ccg cag ttc aac agc caa ggc atc ccc tgc aac    816
Asn Asp Pro Tyr Asn Pro Gln Phe Asn Ser Gln Gly Ile Pro Cys Asn
            260                 265                 270 atg acc ggc ggc tcc tcg ggc gga ccg tgg ttc atc ggc acc agc tcc    864
Met Thr Gly Gly Ser Ser Gly Gly Pro Trp Phe Ile Gly Thr Ser Ser
        275                 280                 285 agc ggt tac cag aac tcg gtc aac agc tac ggc tac ggc agc aag tcc    912
Ser Gly Tyr Gln Asn Ser Val Asn Ser Tyr Gly Tyr Gly Ser Lys Ser
    290                 295                 300 acc aca atg tac ggc ccg tac tgg ggt tca gtg atc cag cag gcg tac    960
Thr Thr Met Tyr Gly Pro Tyr Trp Gly Ser Val Ile Gln Gln Ala Tyr
305                 310                 315                 320 aac acc gca tcc tcg gcc tct tag                                    984
Asn Thr Ala Ser Ser Ala Ser
                325

<210> SEQ ID NO 4
<211> LENGTH: 327
<212> TYPE: PRT
<213> ORGANISM: Unknown
<220> FEATURE:
<223> OTHER INFORMATION: Synthetic Construct

<400> SEQUENCE: 4

Met Thr Ser Thr Arg Thr Leu Ala Thr Ser Leu Met Ser Leu Thr Thr
1               5                   10                  15

Ala Ala Leu Phe Ala Leu Cys Ser Ala Gly Gln Ala Thr Ala Ala Pro
            20                  25                  30

Ala Ser Pro Asp Thr Lys Asp Val Ala Gly Val Ser Ser Ala Ala Val
        35                  40                  45

Thr Asp Thr Ser Gly Ala Asp Tyr Trp Thr Pro Glu Arg Met Arg Ser
    50                  55                  60

Ala Ile Pro Ala Asp Val Leu Ala Lys Lys Ala Val Glu Arg Gln Lys
65                  70                  75                  80

Ser Asn Pro Ala Val Leu Pro Glu Gln Ala Lys Gly Pro Glu Thr Lys
                85                  90                  95

Ile Gln Gly Ser Ala Pro Gln Val Gln Ala Lys Ala Asn Ala Ser Glu
            100                 105                 110

Thr Pro Val Ser His Ile Gly Lys Val Phe Phe Thr Leu Gly Gly Thr
        115                 120                 125

Asn Tyr Val Cys Ser Ala Asn Ser Val Val Ser Thr Asn Arg Asn Thr
    130                 135                 140

Val Ser Thr Ala Gly His Cys Leu Asn Glu Gly Pro Gly Ala Phe Ala
```

-continued

```
                145                 150                 155                 160
Thr Lys Phe Thr Phe Val Pro Ala Tyr Leu Asn Gly Ser Ala Pro Tyr
                    165                 170                 175

Gly Lys Trp Thr Ala Lys Ala Leu Tyr Ala Pro Thr Gln Trp Ser Ser
            180                 185                 190

Ser Gly Ser Met Glu Tyr Asp Thr Gly Phe Ala Val Met Ser Gln Leu
        195                 200                 205

Asn Gly Arg Asn Leu Ala Asp Val Val Gly Ala Ser Gly Val Ser Phe
    210                 215                 220

Asn Ala Arg Gly Leu Ala Tyr Lys Ala Phe Gly Tyr Pro Ala Ala
225                 230                 235                 240

Ser Pro Phe Asn Gly Glu Ser Leu Lys Ser Cys Ser Gly Thr Ala Thr
                245                 250                 255

Asn Asp Pro Tyr Asn Pro Gln Phe Asn Ser Gln Gly Ile Pro Cys Asn
                260                 265                 270

Met Thr Gly Gly Ser Ser Gly Pro Trp Phe Ile Gly Thr Ser Ser
            275                 280                 285

Ser Gly Tyr Gln Asn Ser Val Asn Ser Tyr Gly Ser Lys Ser
        290                 295                 300

Thr Thr Met Tyr Gly Pro Tyr Trp Gly Ser Val Ile Gln Gln Ala Tyr
305                 310                 315                 320

Asn Thr Ala Ser Ser Ala Ser
                325

<210> SEQ ID NO 5
<211> LENGTH: 807
<212> TYPE: DNA
<213> ORGANISM: Bacillus lentus
<220> FEATURE:
<221> NAME/KEY: CDS
<222> LOCATION: (1)..(807)

<400> SEQUENCE: 5 gcg caa tca gtg cca tgg gga att agc cgt gtg caa gcc ccg gct gcc      48
Ala Gln Ser Val Pro Trp Gly Ile Ser Arg Val Gln Ala Pro Ala Ala
1               5                   10                  15 cat aac cgt gga ttg aca ggt tct ggt gta aaa gtt gct gtc ctc gat      96
His Asn Arg Gly Leu Thr Gly Ser Gly Val Lys Val Ala Val Leu Asp
                20                  25                  30 aca ggt att tcc act cat cca gac tta aat att cgt ggt ggc gct agc     144
Thr Gly Ile Ser Thr His Pro Asp Leu Asn Ile Arg Gly Gly Ala Ser
            35                  40                  45 ttt gta cca ggg gaa cca tcc act caa gat ggg aat ggg cat ggc acg     192
Phe Val Pro Gly Glu Pro Ser Thr Gln Asp Gly Asn Gly His Gly Thr
        50                  55                  60 cat gtg gcc ggg acg att gct gct tta aac aat tcg att ggc gtt ctt     240
His Val Ala Gly Thr Ile Ala Ala Leu Asn Asn Ser Ile Gly Val Leu
65                  70                  75                  80 ggc gta gcg cct agt gcg gaa cta tac gct gtt aaa gtt tta gga gcc     288
Gly Val Ala Pro Ser Ala Glu Leu Tyr Ala Val Lys Val Leu Gly Ala
                85                  90                  95 gac ggt aga ggt gca atc agc tcg att gcc caa ggg ttg gaa tgg gca     336
Asp Gly Arg Gly Ala Ile Ser Ser Ile Ala Gln Gly Leu Glu Trp Ala
                100                 105                 110 ggg aac aat ggc atg cac gtt gct aat ttg agt tta gga agc cct tcg     384
Gly Asn Asn Gly Met His Val Ala Asn Leu Ser Leu Gly Ser Pro Ser
            115                 120                 125 cca agt gcc aca ctt gag caa gct gtt aat agc gcg act tct aga ggc     432
```

```
Pro Ser Ala Thr Leu Glu Gln Ala Val Asn Ser Ala Thr Ser Arg Gly
    130                 135                 140 gtt ctt gtt gta gcg gca tct ggg aat tca ggt gca agc tca atc agc       480
Val Leu Val Val Ala Ala Ser Gly Asn Ser Gly Ala Ser Ser Ile Ser
145                 150                 155                 160 tat ccg gcc cgt tat gcg aac gca atg gca gtc gga gct act gac caa       528
Tyr Pro Ala Arg Tyr Ala Asn Ala Met Ala Val Gly Ala Thr Asp Gln
                165                 170                 175 aac aac aac cgc gcc agc ttt tca cag tat ggc gca ggg ctt gac att       576
Asn Asn Asn Arg Ala Ser Phe Ser Gln Tyr Gly Ala Gly Leu Asp Ile
            180                 185                 190 gtc gca cca ggg gta aac gtg cag agc aca tac cca ggt tca acg tat       624
Val Ala Pro Gly Val Asn Val Gln Ser Thr Tyr Pro Gly Ser Thr Tyr
        195                 200                 205 gcc agc tta aac ggt aca tcg atg gct act cct cat gtt gca ggt gca       672
Ala Ser Leu Asn Gly Thr Ser Met Ala Thr Pro His Val Ala Gly Ala
    210                 215                 220 gca gcc ctt gtt aaa caa aag aac cca tct tgg tcc aat gta caa atc       720
Ala Ala Leu Val Lys Gln Lys Asn Pro Ser Trp Ser Asn Val Gln Ile
225                 230                 235                 240 cgc aac cat cta aag aat acg gca acg agc tta gga agc acg aac ttg       768
Arg Asn His Leu Lys Asn Thr Ala Thr Ser Leu Gly Ser Thr Asn Leu
                245                 250                 255 tat gga agc gga ctt gtc aat gca gaa gcg gca aca cgc                   807
Tyr Gly Ser Gly Leu Val Asn Ala Glu Ala Ala Thr Arg
            260                 265

<210> SEQ ID NO 6
<211> LENGTH: 269
<212> TYPE: PRT
<213> ORGANISM: Bacillus lentus

<400> SEQUENCE: 6

Ala Gln Ser Val Pro Trp Gly

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 7
<211> LENGTH: 1448
<212> TYPE: DNA
<213> ORGANISM: Bacillus licheniformis

<400> SEQUENCE: 7

```
tcgacggctt cccgtgcgcc tccgggatcg ctgtgataat tgacaaccac attcatcttt      60
tcttttccaa accgttctgc aaccgccttg cctatacctt tgaagagcc ggtcacaatt     120
gctgttttc cttttaaatc actatacaac ctaaacaccc ctcaatttct tttctccatg     180
tacattaccc ggtatcaata tatgatcaaa caaaatgtta atacacacct ttagtatgat     240
ctttttaaa catatggaaa attcagaatt attttgttaa tatctaactt gtacttacaa     300
caaaataagg aagtgatatg atttggttag taaaagagt gttaaacgag gtttgatcac     360
aggtctcatt ggtatttcta tttattcttt aggtatgcac ccggcccaag ccgcgccatc     420
gcctcatact cctgtttcaa gcgatccttc atacaaagcg gaaacatcgg ttacttatga     480
cccaaacatt aagagcgatc aatacggctt gtattcaaaa gcgtttacag gcaccggcaa     540
agtgaatgaa acaaaggaaa agcggaaaa aaagtcaccc gccaaagctc cttacagcat     600
taaatcggtg attggttctg atgatcggac aagggtcacc aacacaaccg catatccgta     660
cagagcgatc gttcatattt caagcagcat cggttcatgc accggatgga tgatcggtcc     720
gaaaaccgtc gcaacagccg acactgcat ctatgacaca tcaagcggtt catttgccgg     780
tacagccact gtttcgccgg acggaacgg acaagctat ccttacggct cagttaaatc     840
gacgcgctac tttattccgt caggatggag aagcggaaac accaattacg attacggcgc     900
aatcgaacta agcgaaccga tcggcaatac tgtcggatac ttcggatact cgtacactac     960
ttcatcactt gttgggacaa ctgttaccat cagcggctac ccaggcgata aaacagcagg    1020
cacacaatgg cagcattcag gaccgattgc catctccgaa acgtataaat tgcagtacgc    1080
aatggacacg tacggaggac aaagcggttc accggtattc gaacaaagca gctccagaac    1140
gaactgcagc ggtccgtgct cgcttgccgt acacacaaat ggagtatacg gcggctcctc    1200
gtacaacaga ggcacccgga ttacaaaaga ggtgttcgac aatttgacca actggaaaaa    1260
cagcgcacaa taatacacga agacagcccg cttccttttg gaacgggctg tcacatctaa    1320
cggccgtata cttaatttcc tttaagcctg tactttttgc catctattga tatcgtgaaa    1380
tttgaaggac cgctgatcgg caaataatag acaagctgaa actccgcttc ctcaccaggt    1440
ttgaatgg                                                              1448
```

<210> SEQ ID NO 8
<211> LENGTH: 316
<212> TYPE: PRT
<213> ORGANISM: Bacillus licheniformis

<400> SEQUENCE: 8

```
Met Val Ser Lys Lys Ser Val Lys Arg Gly Leu Ile Thr Gly Leu Ile
1               5                   10                  15
Gly Ile Ser Ile Tyr Ser Leu Gly Met His Pro Ala Gln Ala Ala Pro
                20                  25                  30
Ser Pro His Thr Pro Val Ser Ser Asp Pro Ser Tyr Lys Ala Glu Thr
            35                  40                  45
Ser Val Thr Tyr Asp Pro Asn Ile Lys Ser Asp Gln Tyr Gly Leu Tyr
        50                  55                  60
Ser Lys Ala Phe Thr Gly Thr Lys Val Asn Glu Thr Lys Glu Lys
65                  70                  75                  80
Ala Glu Lys Lys Ser Pro Ala Lys Ala Pro Tyr Ser Ile Lys Ser Val
                85                  90                  95
Ile Gly Ser Asp Asp Arg Thr Arg Val Thr Asn Thr Thr Ala Tyr Pro
                100                 105                 110
Tyr Arg Ala Ile Val His Ile Ser Ser Ile Gly Ser Cys Thr Gly
            115                 120                 125
Trp Met Ile Gly Pro Lys Thr Val Ala Thr Ala Gly His Cys Ile Tyr
    130                 135                 140
Asp Thr Ser Ser Gly Ser Phe Ala Gly Thr Ala Thr Val Ser Pro Gly
145                 150                 155                 160
Arg Asn Gly Thr Ser Tyr Pro Tyr Gly Ser Val Lys Ser Thr Arg Tyr
                165                 170                 175
Phe Ile Pro Ser Gly Trp Arg Ser Gly Asn Thr Asn Tyr Asp Tyr Gly
            180                 185                 190
Ala Ile Glu Leu Ser Glu Pro Ile Gly Asn Thr Val Gly Tyr Phe Gly
        195                 200                 205
Tyr Ser Tyr Thr Thr Ser Ser Leu Val Gly Thr Thr Val Thr Ile Ser
    210                 215                 220
Gly Tyr Pro Gly Asp Lys Thr Ala Gly Thr Gln Trp Gln His Ser Gly
225                 230                 235                 240
Pro Ile Ala Ile Ser Glu Thr Tyr Lys Leu Gln Tyr Ala Met Asp Thr
                245                 250                 255
Tyr Gly Gly Gln Ser Gly Ser Pro Val Phe Glu Gln Ser Ser Ser Arg
            260                 265                 270
Thr Asn Cys Ser Gly Pro Cys Ser Leu Ala Val His Thr Asn Gly Val
        275                 280                 285
Tyr Gly Gly Ser Ser Tyr Asn Arg Gly Thr Arg Ile Thr Lys Glu Val
    290                 295                 300
Phe Asp Asn Leu Thr Asn Trp Lys Asn Ser Ala Gln
305                 310                 315
```

<210> SEQ ID NO 9
<211> LENGTH: 648
<212> TYPE: DNA
<213> ORGANISM: Nesterenkonia sp.

<400> SEQUENCE: 9

```
cagaatccgg cggactcccc gcacataggc aaggtcttct tctccaccaa ccagggcgac    60
ttcgtctgct ccgccaacat cgtggcctcg gcgaaccagt ccacggtggc caccgcgggg   120
cactgcctgc acgacggaaa cggcggccag ttcgcacgca acttcgtctt cgcccctgcc   180
tacgactacg gcgagtccga gcacggcgtg tgggccgcag aagagctggt gacctccgcc   240
gagtgggcga accgcggcga cttcgagcat gactacgcct tcgcggtcct cgagaccaag   300
```

```
ggcggcacca ccgtgcagca gcaggtgggg acggcgtcgc cgatcgcctt caaccagccg    360
cgcggccagt actacagcgc ctacggctac ccggccgccg cgcccttcaa cggccaggag    420
ctccacagct gccacggcac cgccacgaac gacccgatgg gcagcagcac tcagggcatc    480
ccgtgcaaca tgaccggcgg ctcctccggc ggcccctggt tcctcggtca ggggaccggc    540
ggtgcccaga actctgtgaa ctcctacggg tacaccttcc tgccggacgt gatgttcggg    600
ccgtacttcg gctccggggc acagcagaac tacaactacg cctccaca               648
```

<210> SEQ ID NO 10
<211> LENGTH: 216
<212> TYPE: PRT
<213> ORGANISM: Nesterenkonia sp.

<400> SEQUENCE: 10

```
Gln Asn Pro Ala Asp Ser Pro His Ile Gly Lys Val Phe Phe Ser Thr
1               5                   10                  15

Asn Gln Gly Asp Phe Val Cys Ser Ala Asn Ile Val Ala Ser Ala Asn
                20                  25                  30

Gln Ser Thr Val Ala Thr Ala Gly His Cys Leu His Asp Gly Asn Gly
            35                  40                  45

Gly Gln Phe Ala Arg Asn Phe Val Phe Ala Pro Ala Tyr Asp Tyr Gly
        50                  55                  60

Glu Ser Glu His Gly Val Trp Ala Ala Glu Glu Leu Val Thr Ser Ala
65                  70                  75                  80

Glu Trp Ala Asn Arg Gly Asp Phe Glu His Asp Tyr Ala Phe Ala Val
                85                  90                  95

Leu Glu Thr Lys Gly Gly Thr Thr Val Gln Gln Val Gly Thr Ala
                100                 105                 110

Ser Pro Ile Ala Phe Asn Gln Pro Arg Gly Gln Tyr Tyr Ser Ala Tyr
            115                 120                 125

Gly Tyr Pro Ala Ala Ala Pro Phe Asn Gly Gln Glu Leu His Ser Cys
        130                 135                 140

His Gly Thr Ala Thr Asn Asp Pro Met Gly Ser Ser Thr Gln Gly Ile
145                 150                 155                 160

Pro Cys Asn Met Thr Gly Gly Ser Ser Gly Gly Pro Trp Phe Leu Gly
                165                 170                 175

Gln Gly Thr Gly Gly Ala Gln Asn Ser Val Asn Ser Tyr Gly Tyr Thr
            180                 185                 190

Phe Leu Pro Asp Val Met Phe Gly Pro Tyr Phe Gly Ser Gly Ala Gln
        195                 200                 205

Gln Asn Tyr Asn Tyr Ala Ser Thr
    210                 215
```

<210> SEQ ID NO 11
<211> LENGTH: 323
<212> TYPE: PRT
<213> ORGANISM: Oceanobacillus iheyensis HTE831

<400> SEQUENCE: 11

```
Met Ser Arg Lys Asn Leu Leu Ser Val Phe Ile Ala Phe Ile Thr Phe
1               5                   10                  15

Leu Ile Ile Thr Pro Ser Val Met Ala Asn Glu Ala Glu Ile Ile Ser
                20                  25                  30

Glu Gln Glu Asp Thr Lys Tyr Gln Met Phe Asp Asn Ser Glu Glu Tyr
            35                  40                  45
```

-continued

```
Trp Thr Lys Glu Lys Met Glu Asn Ala Ile Pro Met Asp Lys His Phe
    50                  55                  60

Asp Ala Thr Glu Ser Lys Ser Leu Thr Asn Ser Glu Glu Ala Asn Lys
65                  70                  75                  80

Ile Gln Thr Ser Glu Lys Ser Tyr Asn Thr Glu Pro Ala Ser Pro Lys
                85                  90                  95

Tyr Asn Asn Ala Leu Asp Phe Ser Pro Asn Ala Val Val Pro Ser Thr
                100                 105                 110

Thr Gly Lys Leu Phe Phe Tyr Asn Pro Asn Asp Gly Asn Asn Tyr Val
            115                 120                 125

Cys Ser Ala Ser Ala Val Asn Asn Pro Asn Lys Asn Leu Val Ser Thr
        130                 135                 140

Ala Gly His Cys Met His Glu Gly Ser Gly Gly Asp Phe Tyr Thr Asn
145                 150                 155                 160

Ile Val Phe Val Pro Ala Tyr Tyr Glu Gly Asn Ala Pro Tyr Gly Arg
                165                 170                 175

Trp Asn Val Asn Trp Lys Val Thr Phe Arg Gly Trp Thr Asp Asn Gly
            180                 185                 190

Asn Tyr Asp Tyr Asp Gln Ala Phe Leu Thr Val Phe Gln Asn Asp Gly
        195                 200                 205

Arg Asn Leu Val Asn Val Val Gly Gly Asn Gly Leu Ser Phe Asn Tyr
    210                 215                 220

Ser Gln Asn Gln Ser Asp Val Arg Val Thr Gly Tyr Pro Ala Ala Asp
225                 230                 235                 240

Pro Tyr Pro Gly Asp Ile Pro Tyr Ser Cys Tyr Gly Asp Thr Ser Lys
                245                 250                 255

Arg Phe Leu Ser Asn Asp Ala Gln Ile Ser Cys Gly Phe Thr Gly Gly
            260                 265                 270

Ala Ser Gly Gly Ala Trp Phe Arg Thr Met Ser Ser Glu Asn Leu Gly
        275                 280                 285

Gln Ile Phe Ala Val Thr Ser Arg Arg Ser Asp Pro Arg Gly Thr Leu
    290                 295                 300

Tyr Ala Arg Pro Phe Thr Ser Asp Tyr Arg Asp Leu Phe Glu Gly Met
305                 310                 315                 320

Glu Asp Arg
```